(12) United States Patent
Maehata et al.

(10) Patent No.: US 9,392,791 B2
(45) Date of Patent: Jul. 19, 2016

(54) AMIDE COMPOUND AND USE THEREOF FOR PEST CONTROL

(71) Applicant: Sumitomo Chemical Company, Tokyo (JP)

(72) Inventors: Ryota Maehata, Takarazuka (JP); Hajime Mizuno, Takarazuka (JP); Chie Shimizu, Takarazuka (JP); Yoshihiko Nokura, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/410,065

(22) PCT Filed: Jun. 5, 2013

(86) PCT No.: PCT/JP2013/066133
§ 371 (c)(1),
(2) Date: Dec. 20, 2014

(87) PCT Pub. No.: WO2014/002754
PCT Pub. Date: Jan. 3, 2014

(65) Prior Publication Data
US 2015/0336895 A1    Nov. 26, 2015

(30) Foreign Application Priority Data
Jun. 26, 2012    (JP) .................. 2012-142765

(51) Int. Cl.
*C07D 213/75*  (2006.01)
*A01N 43/40*   (2006.01)
*A01N 43/54*   (2006.01)
*A01N 43/58*   (2006.01)
*A01N 43/60*   (2006.01)
*A01N 47/02*   (2006.01)

(52) U.S. Cl.
CPC ............... *A01N 43/40* (2013.01); *A01N 43/54* (2013.01); *A01N 43/58* (2013.01); *A01N 43/60* (2013.01); *A01N 47/02* (2013.01); *C07D 213/75* (2013.01)

(58) Field of Classification Search
None
See application file for complete search history.

(56) References Cited

U.S. PATENT DOCUMENTS

| | | |
|---|---|---|
| 2001/0041814 A1 | 11/2001 | Tohnishi et al. |
| 2003/0229050 A1 | 12/2003 | Lahm et al. |
| 2006/0199821 A1 | 9/2006 | Tester et al. |
| 2006/0205748 A1 | 9/2006 | Annis et al. |
| 2010/0305124 A1 | 12/2010 | Fusslein et al. |
| 2014/0018373 A1 | 1/2014 | Takyo et al. |

FOREIGN PATENT DOCUMENTS

| | | |
|---|---|---|
| JP | 2003-034671 A | 2/2003 |
| WO | WO 2005033072 A2 * | 4/2005 |

OTHER PUBLICATIONS

Int'l Search Report issued Sep. 10, 2013 in Int'l Application No. PCT/JP2013/066133.
Chemical compounds appearing in the CAS Registry as RN=1355888-68-4, RN=1090532-18-5, RN=895858-75-0, RN=881790-92-7, RN=663186-73-0; cited in the Int'l Search Report (Dated Sep. 10, 2013).

* cited by examiner

*Primary Examiner* — Zinna Northington Davis
(74) *Attorney, Agent, or Firm* — Panitch Schwarze Belisario & Nadel LLP

(57) ABSTRACT

Amide compounds and methods of using the amide compounds for pest control are provided. In particular, amide compounds of formula (1) below show excellent effects in controlling pests

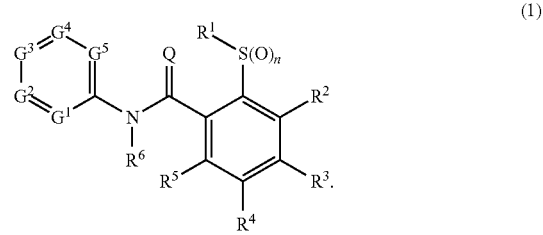

(1)

14 Claims, No Drawings

AMIDE COMPOUND AND USE THEREOF FOR PEST CONTROL

CROSS-REFERENCE TO RELATED APPLICATION

This application is a Section 371 of International Application No. PCT/JP2013/066133, filed Jun. 5, 2013, which was published in the Japanese language on Jan. 3, 2014, under International Publication No. WO 2014/002754 A1, and the disclosure of which is incorporated herein by reference.

TECHNICAL FIELD

The present invention relates to a certain kind of amide compound and a use thereof for pest control.

BACKGROUND ART

So far, for the purpose of pest control, various compounds have been studied and put to practical use.
On the other hand, US2006/0199821 describes an amide compound that can be used as a medicine.

SUMMARY OF THE INVENTION

The present invention provides a compound having an excellent control effect on pests and a method for controlling pests using the compound.
The present invention is as described below.
[1] An amide compound represented by formula (1) or an N-oxide thereof (hereinafter, the amide compound represented by the formula (1) and the N-oxide thereof are referred to as the compound of the present invention):

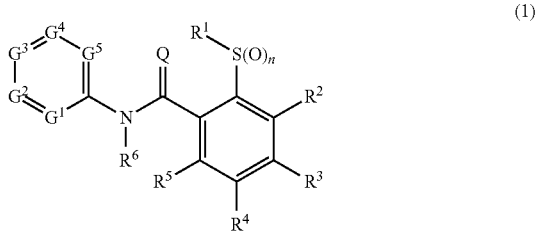

(1)

wherein
$R^1$ represents a C1 to C6 chain hydrocarbon group optionally having one or more atoms or groups selected from group X or a C3 to C6 cycloalkyl group optionally having one or more atoms or groups selected from group Y,
$R^2$, $R^3$, $R^4$ and $R^5$ are the same or different and represent a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-S(O)_2NR^{12}R^{13}$, $-NR^{12}R^{13}$, $-NR^{12}C(O)R^{13}$, $-NR^{12}CO_2R^{13}$, $-NR^{12}S(O)_2R^{14}$, $-C(O)R^{12}$, $-CO_2R^{12}$, $-C(O)NR^{12}R^{13}$, $-SF_5$, a cyano group, a nitro group, a halogen atom, or a hydrogen atom,
$R^6$ represents a C1 to C6 chain hydrocarbon group optionally having one or more atoms or groups selected from group W, a C3 to C6 cycloalkyl group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $-C(O)R^{12}$, $-C(O)OR^{12}$, or $-C(O)NR^{12}R^{13}$,
$G^1$ represents a nitrogen atom or $=CR^7-$,
$G^2$ represents a nitrogen atom or $=CR^8-$,
$G^3$ represents a nitrogen atom or $=CR^9-$,
$G^4$ represents a nitrogen atom or $=CR^{10}-$,
$G^5$ represents a nitrogen atom or $=CR^{11}-$ (wherein at least one of $G^1$, $G^2$, $G^3$, $G^4$ and $G^5$ represents a nitrogen atom, but not all of $G^2$, $G^3$ and $G^4$ represent a nitrogen atom),
$R^7$ and $R^{11}$ are the same or different and represent a C1 to C6 chain hydrocarbon group optionally having one or more atoms or groups selected from group X, a C3 to C6 cycloalkyl group optionally having one or more atoms or groups selected from group Y, $-OR^{15}$, $-S(O)_mR^{15}$, a fluorine atom, or a hydrogen atom,
$R^8$, $R^9$ and $R^{10}$ are the same or different and represent a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-S(O)_2NR^{12}R^{13}$, $-NR^{12}R^{13}$, $-NR^{12}C(O)R^{13}$, $-NR^{12}CO_2R^{13}$, $-NR^{12}S(O)_2R^{14}$, $-C(O)R^{12}$, $-CO_2R^{12}$, $-C(O)NR^{12}R^{13}$, $-SF_5$, a cyano group, a nitro group, a halogen atom, or a hydrogen atom (wherein at least one of $R^8$, $R^9$ and $R^{10}$ represents a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-S(O)_2NR^{12}R^{13}$, $-NR^{12}R^{13}$, $-NR^{12}C(O)R^{13}$, $-NR^{12}CO_2R^{13}$, $-NR^{12}S(O)_2R^{14}$, $-C(O)R^{12}$, $-CO_2R^{12}$, $-C(O)NR^{12}R^{13}$, $-SF_5$, a cyano group, a nitro group, or a halogen atom),
$R^{12}$ and $R^{13}$ are the same or different and represent a C1 to C6 chain hydrocarbon group optionally having one or more halogen atoms, a phenyl group optionally having one or more atoms or groups selected from group Z, a 5- or 6-membered heterocyclic group optionally having one or more atoms or groups selected from group Z, or a hydrogen atom,
$R^{14}$ represents a C1 to C6 chain hydrocarbon group optionally having one or more halogen atoms, a phenyl group optionally having one or more atoms or groups selected from group Z, or a 5- or 6-membered heterocyclic group optionally having one or more atoms or groups selected from group Z,
$R^{15}$ represents a C1 to C6 alkyl group optionally having one or more halogen atoms,
Q represents an oxygen atom or a sulfur atom,
m represents 0, 1 or 2, and
n represents 0, 1 or 2,
wherein, when $R^1$ represents an ethyl group, $R^2$, $R^3$, $R^4$ and $R^5$ represent a hydrogen atom, $G^1$, $G^4$ and $G^5$ represent $=CH-$, and $G^2$ represents an nitrogen atom, $G^3$ does not represent $=C(OCH_3)-$, and
when m is 1 or 2 in $-S(O)_mR^{12}$, $R^{12}$ does not represent a hydrogen atom,
Group X: a group consisting of C3 to C6 cycloalkyl groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms.

Group Y: a group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms.

Group Z: a group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C1 to C6 alkylamino groups optionally having one or more halogen atoms, C2 to C8 dialkylamino groups optionally having one or more halogen atoms, C2 to C6 alkylcarbonyl groups optionally having one or more halogen atoms, C2 to C6 alkoxycarbonyl groups optionally having one or more halogen atoms, hydroxy groups, thiol groups, amino groups, cyano groups, nitro groups, and halogen atoms.

Group W: a group consisting of C3 to C6 cycloalkyl groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkoxycarbonyl groups optionally having one or more halogen atoms, hydroxy groups, nitrile groups, and halogen atoms.

[2] The compound according to [1] or an N-oxide thereof, wherein $R^1$ is a C3 to C6 cycloalkyl group optionally having one or more atoms or groups selected from the group consisting of halogen atoms and C1 to C3 alkyl groups, a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms, $R^2$, $R^4$ and $R^5$ are the same or different and are a C1 to C6 alkyl group optionally having one or more halogen atoms, —$OR^{12}$, —$S(O)_mR^{12}$, a halogen atom, or a hydrogen atom, $R^3$ represents a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, —$OR^{12}$, —$S(O)_mR^{12}$, —$NR^{12}R^{13}$, —$NR^{12}C(O)R^{13}$, —$NR^{12}CO_2R^{13}$, —$NR^{12}S(O)_2R^{12}$, —$C(O)R^{12}$, —$CO_2R^{12}$, —$C(O)NR^{12}R^{13}$, —$SF_5$, a cyano group, a nitro group, a halogen atom, or a hydrogen atom, $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), a (C1 to C6 alkoxy)C1 to C6 alkyl group optionally having one or more halogen atoms, —$C(O)R^{12}$, or —$C(O)OR^{12}$, one or two of $G^1$, $G^2$, $G^3$, $G^4$ and $G^5$ are a nitrogen atom, $R^7$ and $R^{11}$ are the same or different and are a C1 to C6 alkyl group optionally having one or more halogen atoms, —$OR^{15}$, —$S(O)_mR^{15}$, a fluorine atom, or a hydrogen atom, $R^8$, $R^9$ and $R^{10}$ are the same or different and are a C1 to C6 chain hydrocarbon group optionally having one or more atoms or groups selected from group X, —$OR^{12}$, —$S(O)_mR^{12}$, —$SF_5$, a halogen atom, or a hydrogen atom, $R^{12}$ and $R^{13}$ are the same or different and are a C1 to C6 alkyl group optionally having one or more halogen atoms, a phenyl group (wherein the phenyl group optionally has one or more atoms or groups selected from the group consisting of C1 to C3 alkyl groups optionally having one or more halogen atoms and halogen atoms), a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), or a hydrogen atom, $R^{14}$ is a C1 to C6 alkyl group optionally having one or more halogen atoms, a phenyl group (wherein the phenyl group optionally has a C1 to C3 alkyl group optionally having one or more halogen atoms or one or more halogen atoms), or a 5- or 6-membered heterocyclic group (wherein the 5- or 6-membered heterocyclic group optionally has a C1 to C3 alkyl group optionally having one or more halogen atoms or one or more halogen atoms), and Q is an oxygen atom.

[3] The compound according to [1] or an N-oxide thereof, wherein $R^1$ is a C3 to C6 cycloalkyl group optionally having one or more atoms or groups selected from the group consisting of halogen atoms and C1 to C3 alkyl groups, a C2 to C6 alkyl group optionally having one or more halogen atoms, or a (C3 to C6 cycloalkyl)C1 to C3 alkyl group optionally having one or more halogen atoms, $R^2$, $R^4$ and $R^5$ are the same or different and are a halogen atom or a hydrogen atom, $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), —$OR^{12}$, —$S(O)_mR^{12}$, —$NR^{12}R^{13}$, —$NR^{12}C(O)R^{13}$, —$NR^{12}CO_2R^{13}$, —$NR^{12}S(O)_2R^{14}$, —$C(O)R^{12}$, —$CO_2R^{12}$, —$C(O)NR^{12}R^{13}$, a halogen atom, or a hydrogen atom, $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms, or a C2 to C6 alkoxycarbonyl group optionally having one or more halogen atoms, one or two of $G^1$, $G^2$, $G^3$, $G^4$ and $G^5$ are a nitrogen atom, $R^7$ and $R^{11}$ are the same or different and are a fluorine atom or a hydrogen atom, $R^8$, $R^9$ and $R^{10}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, $-OR^{12}$, $-S(O)_m R^{12}$, a halogen atom, or a hydrogen atom, $R^{12}$ and $R^{13}$ are the same or different and are a C1 to C6 alkyl group optionally having one or more halogen atoms or a hydrogen atom, $R^{14}$ is a C1 to C6 alkyl group optionally having one or more halogen atoms, and Q is an oxygen atom.

[4] The compound according to [1] or an N-oxide thereof, wherein $R^1$ is a C2 to C6 alkyl group, a cyclopropyl group or a cyclopropylmethyl group, $R^2$, $R^4$ and $R^5$ are a hydrogen atom, $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or groups selected from the group consisting of C1 to C3 alkyl groups optionally having one or more halogen atoms and halogen atoms), a halogen atom, or a hydrogen atom, $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms, or a C2 to C6 alkoxycarbonyl group optionally having one or more halogen atoms, one or two of $G^1$, $G^2$, $G^3$, $G^4$ and $G^5$ are a nitrogen atom, $R^7$ and $R^{11}$ are the same or different and are a fluorine atom or a hydrogen atom, $R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom, and Q is an oxygen atom.

[5] The compound as defined in any of [1] to [4] described above, wherein two of $G^1$, $G^2$, $G^3$, $G^4$ and $G^5$ are a nitrogen atom.

[6] The compound as defined in any of [1] to [4] described above, wherein one of $G^1$, $G^2$, $G^3$, $G^4$ and $G^5$ is a nitrogen atom.

[7] The compound as defined in any of [1] to [4] described above, wherein $G^1$ is a nitrogen atom or $=CR^7-$, $G^2$ is a nitrogen atom or $=CR^8-$, $G^3$ is $=CR^9-$, $G^4$ is $=CR^{10}-$, $G^5$ is a nitrogen atom or $=CR^{11}-$, and one or two of $G^1$, $G^2$ and $G^5$ are a nitrogen atom.

[8] The compound as defined in any of [1] to [4] described above, wherein $G^1$ is a nitrogen atom, $G^2$ is $=CR^8-$, $G^3$ is $=CR^9-$, $G^4$ is $=CR^{10}-$, and $G^5$ is $=CR^{11}-$.

[9] The compound as defined in any of [1] to [4] described above, wherein $G^1$ is $=CR^7-$, $G^2$ is a nitrogen atom, $G^3$ is $=CR^9-$, $G^4$ is $=CR^{10}-$, and $G^5$ is $=CR^{11}-$.

[10] The compound as defined in any of [1] to [4] described above, wherein $G^1$ is a nitrogen atom or $=CR^7-$, $G^2$ is a nitrogen atom or $=CR^8-$, $G^3$ is $=CR^9-$, $G^4$ is $=CR^{10}-$, $G^5$ is a nitrogen atom or $=CR^{11}-$ (wherein one or two of $G^1$, $G^2$ and $G^5$ represent a nitrogen atom), $R^7$ and $R^{11}$ are the same or different and are a fluorine atom or a hydrogen atom, and $R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom, or a hydrogen atom.

[11] The compound as defined in any of [1] to [4] described above, wherein $G^1$ is a nitrogen atom or $=CH-$, $G^2$ is a nitrogen atom or $=CR^8-$, $G^3$ is $=CR^9-$, $G^4$ is $=CR^{10}-$, $G^5$ is a nitrogen atom or $=CH-$ (wherein one or two of $G^1$, $G^2$ and $G^5$ represent a nitrogen atom), and $R^8$, $R^9$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom, or a hydrogen atom.

[12] A pest control composition comprising the compound as defined in any of [1] to [11] described above, and an inert carrier.

[13] A method for controlling pests comprising applying an effective amount of the compound as defined in any of [1] to [11] described above to a pest or a pest-infested area.

[14] A compound represented by formula (2) or an N-oxide thereof (hereinafter, the compound represented by the formula (2) and the N-oxide thereof are referred to as the present intermediate compound):

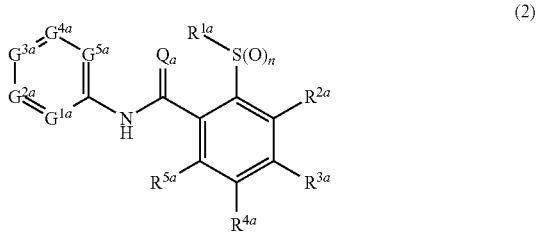

(2)

wherein $R^{1a}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms, or a (C3 to C6 cycloalkylalkyl)C1 to C3 alkyl group optionally having one or more halogen atoms, $R^{2a}$, $R^{4a}$ and $R^{5a}$ are the same or different and represent a halogen atom or a hydrogen atom, $R^{3a}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having a halogen atom, C1 to C3 alkoxy groups optionally having a halogen atom, and halogen atoms), a pyrimidinyl group (wherein the pyrimidinyl group optionally has one or more atoms or groups selected from the group consisting of C1 to C3 alkyl groups optionally having a halogen atom, C1 to C3 alkoxy groups optionally having a halogen atom, and halogen atoms), a halogen atom or a hydrogen atom, $G^{1a}$ represents a nitrogen atom or $=CR^{7a}-$,
$G^{2a}$ represents a nitrogen atom or $=CR^{8a}-$,
$G^{3a}$ represents $=CR^{9a}-$,
$G^{4a}$ represents $=CR^{10a}-$,
$G^{5a}$ represents a nitrogen atom or $=CR^{11a}-$ (wherein one or two of $G^{1a}$, $G^{2a}$ and $G^{5a}$ represent a nitrogen atom), $R^{7a}$ and $R^{11a}$ are the same or different and represent a fluorine atom or a hydrogen atom, and $R^{8a}$, $R^{9a}$ and $R^{10a}$ are the same or different and represent a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8a}$, $R^{9a}$ and $R^{10a}$ do not represent a hydrogen atom at the same time, and at least one of $R^{8a}$, $R^{9a}$ and $R^{10a}$ represents a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group, or a C1 to C6 haloalkylsulfonyl group), $Q^a$ represents an oxygen atom or a sulfur atom, and n represents 0, 1 or 2.

[15] A pest control composition comprising the compound as defined in [14] described above, and an inert carrier.

[16] A method for controlling pests comprising applying an effective amount of the compound as defined in [14] described above to a pest or a pest-infested area.

MODE FOR CARRYING OUT THE INVENTION

In the compound of the present invention and the present intermediate compound, an N-oxide is a compound in which the nitrogen atom constituting the ring on the heterocyclic group is oxidized. Examples of the heterocyclic group that may form the N-oxide include a pyridine ring.

The groups used in the description of the present specification will be described below with examples.

The notation of Ca to Cb chain hydrocarbon group in the present invention represents a straight-chain or branched-chain saturated or unsaturated hydrocarbon group having the number of carbon atoms of a to b.

Examples of the "C1 to C6 chain hydrocarbon group" include C1 to C6 alkyl groups such as a methyl group, an ethyl group, a propyl group, an isopropyl group, a butyl group, an isobutyl group, a sec-butyl group, a tert-butyl group, a pentyl group, a neopentyl group and a hexyl group; C2 to C6 alkenyl groups such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group and a 1-hexenyl group; and C2 to C6 alkynyl groups such as an ethynyl group, a propargyl group, a 2-butynyl group, a 3-butynyl group, a 1-pentynyl group and a 1-hexynyl group.

The notation of Ca to Cb alkyl group in the present invention represents a straight-chain or branched-chain hydrocarbon group having the number of carbon atoms of a to b.

Examples of the "C1 to C6 alkyl group" include C1 to C6 alkyl groups such as a methyl group, an ethyl group, a propyl group, an isopropyl group, a butyl group, an isobutyl group, a sec-butyl group, a tert-butyl group, a pentyl group, a neopentyl group, and a hexyl group.

The notation of Ca to Cb alkenyl group in the present invention represents a straight-chain or branched-chain unsaturated hydrocarbon group having the number of carbon atoms of a to b, and having one or two or more double bonds in the molecule.

Examples of the "C2 to C6 alkenyl group" include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, and a 1-hexenyl group.

The notation of Ca to Cb alkynyl group in the present invention represents a straight-chain or branched-chain unsaturated hydrocarbon group having the number of carbon atoms of a to b, and having one or two or more triple bonds in the molecule.

Examples of the "C2 to C6 alkynyl group" include an ethynyl group, a propargyl group, a 2-butynyl group, a 3-butynyl group, a 1-pentynyl group, and a 1-hexynyl group.

The notation of Ca to Cb cycloalkyl group in the present invention represents a cyclic alkyl group having the number of carbon atoms of a to b.

Examples of the "C3 to C6 cycloalkyl group" include a cyclopropyl group, a cyclobutyl group, a cyclopentyl group, and a cyclohexyl group.

The notation of Ca to Cb alkoxy group in the present invention represents a group represented by a straight-chain or branched-chain alkyl —O— group having the number of carbon atoms of a to b.

Examples of the "C1 to C6 alkoxy group" include a methoxy group, an ethoxy group, a propoxy group, an isopropoxy group, a butoxy group, an isobutoxy group, a sec-butoxy group, a tert-butoxy group, a pentyloxy group, a neopentyloxy group, and a hexyloxy group.

The notation of Ca to Cb alkylsulfanyl group in the present invention represents a straight-chain or branched-chain alkyl —S— group having the number of carbon atoms of a to b.

Examples of the "C1 to C6 alkylsulfanyl group" include a methylsulfanyl group, an ethylsulfanyl group, a propylsulfanyl group, an isopropylsulfanyl group, a butylsulfanyl group, a pentylsulfanyl group, and a hexylsulfanyl group.

The notation of Ca to Cb alkylsulfinyl group in the present invention represents a straight-chain or branched-chain alkyl —S(O)— group having the number of carbon atoms of a to b.

Examples of the "C1 to C6 alkylsulfinyl group" include a methylsulfinyl group, an ethylsulfinyl group, a propylsulfinyl group, an isopropylsulfinyl group, a butylsulfinyl group, a pentylsulfinyl group, and a hexylsulfinyl group.

The notation of Ca to Cb alkylsulfonyl group in the present invention represents a straight-chain or branched-chain alkyl —S(O)$_2$— group having the number of carbon atoms of a to b.

Examples of the "C1 to C6 alkylsulfonyl group" include a methylsulfonyl group, an ethylsulfonyl group, a propylsulfonyl group, an isopropylsulfonyl group, a butylsulfonyl group, a pentylsulfonyl group, and a hexylsulfonyl group.

The notation of Ca to Cb alkylamino group in the present invention represents a straight-chain or branched-chain alkyl —NH— group having the number of carbon atoms of a to b.

Examples of the "C1 to C6 alkylamino group" include a methylamino group, an ethylamino group, a propylamino group, an isopropylamino group, and a butylamino group.

The notation of Ca to Cb dialkylamino group in the present invention represents a straight-chain or branched-chain dialkylamino group having a total number of carbon atoms of each alkyl group of a to b, in which the number of carbon atoms of each alkyl group may be the same or different.

Examples of the "C2 to C8 dialkylamino group" include a dimethylamino group, a diethylamino group, and a dipropylamino group.

The notation of Ca to Cb alkylcarbonyl group in the present invention represents a straight-chain or branched-chain alkyl —C(O)— group having the number of carbon atoms of a to b.

Examples of the "C2 to C6 alkylcarbonyl group" include an acetyl group, a propionyl group, a butyryl group, a pentanoyl group, and a hexanoyl group.

The notation of Ca to Cb alkoxycarbonyl group in the present invention represents a straight-chain or branched-chain alkyl —O—C(O)— group having the number of carbon atoms of a to b.

Examples of the "C2 to C6 alkoxycarbonyl group" include a methoxycarbonyl group, an ethoxycarbonyl group, a propoxycarbonyl group, a butoxycarbonyl group, a pentyloxycarbonyl group, and a tert-butoxycarbonyl group.

The notation of (Ca to Cb alkoxy)Cc to Cd alkyl group in the present invention represents a Cc to Cd alkyl group in which a hydrogen atom bound to the carbon atom of the Cc to Cd alkyl group is substituted by a Ca to Cb alkoxy group. The numbers of carbon atoms of the alkoxy group and the alkyl group are the same or different, and the notation represents a straight-chain or branched-chain alkyl —O— alkyl group.

The "(C1 to C6 alkoxy)C1 to C6 alkyl group" in the present invention is a C1 to C6 alkyl group combining with a C1 to C6 alkoxy group, and the number of carbon atoms of the (C1 to C6 alkoxy)C1 to C6 alkyl group is 2 to 12.

Examples of the "(C1 to C6 alkoxy)C1 to C6 alkyl group" include a methoxymethyl group, an ethoxymethyl group, a 1-(methoxy)ethyl group, a 2-(methoxy)ethyl group, a 1-(ethoxy)ethyl group, and a 2-(ethoxy)ethyl group.

The notation of (Ca to Cb cycloalkyl)Cc to Cd alkyl group in the present invention represents a Cc to Cd alkyl group in which a hydrogen atom bound to the carbon atom of the Cc to Cd alkyl group is substituted by a Ca to Cb cycloalkyl group. The numbers of carbon atoms of the cycloalkyl group and the alkyl group may be the same or different, and the notation represents a cyclic alkyl-alkyl group.

The "(C3 to C6 cycloalkyl)C1 to C3 alkyl group" in the present invention is a C1 to C3 alkyl group combining with a C3 to C6 cycloalkyl group, and the number of carbon atoms of the (C3 to C6 cycloalkyl)C1 to C3 alkyl group is 4 to 9.

Examples of the "(C3 to C6 cycloalkyl)C1 to C3 alkyl group" include a cyclopropylmethyl group, a 2-cyclopropylethyl group, and a 1-cyclopropylethyl group.

The notation of Ca to Cb haloalkyl group in the present invention represents a straight-chain or branched-chain hydrocarbon group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

The notation of Ca to Cb haloalkenyl group in the present specification represents a straight-chain or branched-chain unsaturated hydrocarbon group having the number of carbon atoms of a to b, in which one or more hydrogen atoms bound to the carbon atom are substituted by a halogen atom, and having one or two or more double bonds in the molecule and at that time, when having two or more halogen atoms, those halogen atoms may be the same or different from each other.

Examples of the "C2 to C6 haloalkenyl group" include a 3,3-dichloro-2-propenyl group and a 3,3-dibromo-2-propenyl group.

The notation of Ca to Cb haloalkoxy group in the present specification represents a straight-chain or branched-chain alkyl —O— group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkoxy group" include a trifluoromethoxy group, a 2,2,2-trifluoroethoxy group, a 2,2,2-trichoroethoxy group, a 2,2,3,3-tetrafluoropropoxy group, and a 2,2,3,4,4,4-hexafluorobutoxy group.

The notation of Ca to Cb haloalkylsulfanyl group in the present specification represents a straight-chain or branched-chain alkyl —S— group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkylsulfanyl group" include a trifluoromethylsulfany group, a 2,2,2-trifluoroethylsulfanyl group, a 2,2,2-trichoroethylsulfanyl group, a 2,2,3,3-tetrafluoropropylsulfanyl group, and a 2,2,3,4,4,4-hexafluorobutylsulfanyl group.

The notation of Ca to Cb haloalkylsulfinyl group in the present specification represents a straight-chain or branched-chain alkyl —S(O)— group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkylsulfinyl group" include a trifluoromethylsulfiny group, a 2,2,2-trifluoroethylsulfinyl group, a 2,2,2-trichoroethylsulfinyl group, a 2,2,3,3-tetrafluoropropylsulfinyl group, and a 2,2,3,4,4,4-hexafluorobutylsulfinyl group.

The notation of Ca to Cb haloalkylsulfonyl group in the present specification represents a straight-chain or branched-chain alkyl —S(O)$_2$— group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkylsulfonyl group" include a trifluoromethylsulfony group, a 2,2,2-trifluoroethylsulfonyl group, a 2,2,2-trichoroethylsulfonyl group, a 2,2,3,3-tetrafluoropropylsulfonyl group, and a 2,2,3,4,4,4-hexafluorobutylsulfonyl group.

The notation of Ca to Cb perfluoroalkyl in the present specification represents a straight-chain or branched-chain alkyl group having the number of carbon atoms of a to b, in which all hydrogen atoms bound to the carbon atom are substituted by a fluorine atom.

Examples of the "C1 to C3 perfluoroalkyl group" include a trifluoromethyl group, a pentafluoroethyl group, a heptafluoropropyl group, and a heptafluoroisopropyl group.

The notation of Ca to Cb perfluoroalkoxy in the present specification represents a straight-chain or branched-chain alkyl —O— group having the number of carbon atoms of a to b, in which all hydrogen atoms bound to the carbon atom are substituted by a fluorine atom.

Examples of the "C1 to C3 perfluoroalkoxy group" include a trifluoromethoxy group, a pentafluoroethoxy group, a heptafluoropropoxy group, and a heptafluoroisopropoxy group.

The notation of Ca to Cb perfluoroalkylsulfanyl in the present specification represents a straight-chain or branched-chain alkyl —S— group having the number of carbon atoms of a to b, in which all hydrogen atoms bound to the carbon atom are substituted by a fluorine atom.

Examples of the "C1 to C3 perfluoroalkylsulfanyl group" include a trifluoromethylsulfanyl group, a pentafluoroethylsulfanyl group, a heptafluoropropylsulfanyl group, and a heptafluoroisopropylsulfanyl group.

The notation of Ca to Cb perfluoroalkylsulfinyl in the present specification represents a straight-chain or branched-chain alkyl —S(O)— group having the number of carbon atoms of a to b, in which all hydrogen atoms bound to the carbon atom are substituted by a fluorine atom.

Examples of the "C1 to C3 perfluoroalkylsulfinyl group" include a trifluoromethylsulfinyl group, a pentafluoroethyl-sulfinyl group, a heptafluoropropylsulfinyl group, and a heptafluoroisopropylsulfinyl group.

The notation of Ca to Cb perfluoroalkylsulfonyl in the present specification represents a straight-chain or branched-chain alkyl —S(O)$_2$— group having the number of carbon atoms of a to b, in which all hydrogen atoms bound to the carbon atom are substituted by a fluorine atom.

Examples of the "C1 to C3 perfluoroalkylsulfonyl group" include a trifluoromethylsulfonyl group, a pentafluoroethyl-sulfonyl group, a heptafluoropropylsulfonyl group, and a heptafluoroisopropylsulfonyl group.

In the notation of "optionally having one or more atoms or groups selected from group X" in the present specification, when having two or more atoms or groups selected from group X, the atoms or groups selected from the group X may be the same or different from each other.

In the notation of "optionally having one or more atoms or groups selected from group Y" in the present specification, when having two or more atoms or groups selected from group Y, the atoms or groups selected from the group Y may be the same or different from each other.

In the notation of "optionally having one or more atoms or groups selected from group Z" in the present specification, when having two or more atoms or groups selected from group Z, the atoms or groups selected from the group Z may be the same or different from each other.

In the notation of "optionally having one or more atoms or groups selected from group W" in the present specification, when having two or more atoms or groups selected from group W, the atoms or groups selected from the group W may be the same or different from each other.

In the notation of "optionally having one or more halogen atoms" in the present specification, when having two or more halogen atoms, those halogen atoms may be the same or different from each other.

In the notation of "optionally having one or more atoms or groups selected from halogen atoms and C1 to C3 alkyl groups" in the present specification, when having two or more atoms or groups, the atoms or groups may be the same or different from each other.

The "halogen atom" in the present invention refers to a fluorine atom, a chlorine atom, a bromine atom, and an iodine atom.

The notation of the "C1 to C6 chain hydrocarbon group optionally having one or more atoms or groups selected from group X" in the present invention represents a straight-chain or branched-chain hydrocarbon group comprising a carbon atom number of 1 to 6, in which a hydrogen atom bound to the carbon atom is optionally substituted by an atom or group selected from group X, and at that time, when having two or more atoms or groups selected from group X, the atoms or groups selected from group X may be the same or different from each other.

Examples of the "C1 to C6 chain hydrocarbon group optionally having one or more atoms or groups selected from group X" include C1 to C6 alkyl groups optionally having one or more atoms or groups selected from group X such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2-trifluoroethyl group, a pentafluoroethyl group, a methylsulfanylethyl group, an ethylsulfanylethyl group, a methylsulfinylethyl group, a methylsulfonylethyl group, a cyclopropylmethyl group, a 1-methylcyclopropylmethyl group, and a 2,2-difluorocyclopropylmethyl group; C2 to C6 alkenyl groups optionally having one or more atoms or groups selected from group X such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group X such as an ethynyl group, a propargyl group, a 2-butynyl group, a 3-butynyl group, a 1-pentynyl group, a 1-hexynyl group, a 4,4,4-trifluoro-2-butynyl group, and the C1 to C6 chain hydrocarbon group optionally having one or more atoms or groups selected from group X is selected in the range of each specified number of carbon atoms.

The notation of the "C3 to C6 cycloalkyl group optionally having one or more atoms or groups selected from group Y" in the present invention represents a cyclic alkyl group comprising a carbon atom number of 3 to 6, in which a hydrogen atom bound to the carbon atom is optionally substituted by an atom or group selected from group Y, and at that time, when having two or more atoms or groups selected from group Y, the atoms or groups selected from group Y may be the same or different from each other.

Examples of the "C3 to C6 cycloalkyl group optionally having one or more atoms or groups selected from group Y" include a cyclopropyl group, a cyclobutyl group, a cyclopentyl group, a cyclohexyl group, a 1-methylcyclohexyl group, a 2-methylcyclohexyl group, a 3-methylcyclohexyl group, a 4-methylcyclohexyl group, a 2-methoxylcyclohexyl group, a 3-methoxylcyclohexyl group, a 4-methoxylcyclohexyl group, a 1-fluorocyclohexyl group, a 2-fluorocyclohexyl group, a 3-fluorocyclohexyl group, and a 4-fluorocyclohexyl group.

The notation of the "C1 to C6 chain hydrocarbon group optionally having one or more atoms or groups selected from group W" in the present invention represents a straight-chain or branched-chain hydrocarbon group comprising a carbon atom number of 1 to 6, in which a hydrogen atom bound to the carbon atom is optionally substituted by an atom or group selected from group W, and at that time, when having two or more atoms or groups selected from group W, the atoms or groups selected from group W may be the same or different from each other.

Examples of the "C1 to C6 chain hydrocarbon group optionally having one or more atoms or groups selected from group W" include C1 to C6 alkyl groups optionally having one or more atoms or groups selected from group W such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a methoxymethyl group, an ethoxymethyl group, a propyloxymethyl group, an isopropyloxymethyl group, a butyloxymethyl group, a sec-butyloxymethyl group, an isobutyloxymethyl group, a tert-butyloxymethyl group, a methoxyethyl group, an ethoxyethyl group, a propoxyethyl group, an isopropoxyethyl group, a butoxyethyl group, a sec-butoxyethyl group, an isobutoxyethyl group, a tert-butoxyethyl group, a methylsulfanylethyl group, an ethylsulfanylethyl group, a methylsulfinylethyl group, a methylsulfonylethyl group, a methoxycarbonylmethyl group, a methoxycarbonylethyl group, a 2-cyanoethyl group, a propyl-2-one group, a cyclopropylmethyl group, and a cyclohexylmethyl group; C2 to C6 alkenyl groups optionally having one or more atoms or groups selected from group W such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group W such as an ethynyl group, a propargyl group, a 2-butynyl group, a 3-butynyl group, a 1-pentynyl group, a 1-hexynyl group, and a 4,4,4-trifluoro-2-butynyl group. At that time, when having two or more atoms or groups selected from group W, the atoms or groups selected from group W may be the same or different from each other.

Examples of the "C1 to C6 chain hydrocarbon group optionally having one or more halogen atoms" in the present invention include C1 to C6 alkyl groups optionally having one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group and a heptafluoroisopropyl group; C2 to C6 alkenyl groups optionally having one or more halogen atoms such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more halogen atoms such as an ethynyl group, a propargyl group, a 2-butynyl group, a 3-butynyl group, a 1-pentynyl group, a 1-hexynyl group and a 4,4,4-trifluoro-2-butynyl group.

Examples of the "C1 to C6 alkyl group optionally having one or more halogen atoms" in the present invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the C2 to C6 alkyl group optionally having one or more halogen atoms" in the present invention include an ethyl group, a propyl group, an isopropyl group, a butyl group, an isobutyl group, a sec-butyl group, a tert-butyl group, a pentyl group, a neopentyl group, a hexyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C1 to C3 alkyl groups optionally having one or more halogen atoms" in the present invention include a methyl group, an ethyl group, a propyl group, an isopropyl group, a trifluoromethyl group, a trichloromethyl group, a 2,2-difluoroethyl group, and a 2,2,2-trifluoroethyl group.

Examples of the "C2 to C6 alkenyl group optionally having one or more halogen atoms" in the present invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C2 to C6 alkynyl group optionally having one or more halogen atoms" in the present invention include an ethynyl group, a propargyl group, a 2-butynyl group, a 3-butynyl group, a 1-pentynyl group, a 1-hexynyl group, and a 4,4,4-trifluoro-2-butynyl group.

The notation of the "a (C1 to C6 alkoxy)C1 to C6 alkyl group optionally having one or more halogen atoms" in the present invention represents a C1 to C6 alkyl group having one C1 to C6 alkoxy group optionally having one or more halogen atoms, and when having two or more halogen atoms, those halogen atoms may be the same or different from each other. Examples include a methoxymethyl group, an ethoxymethyl group, a 1-(methoxy)ethyl group, a 2-(methoxy)ethyl group, a 1-(ethoxy)ethyl group, a 2-(ethoxy)ethyl group, and a (2,2,2-trifluoroethoxy)methyl group.

Examples of the "C3 to C6 cycloalkyl groups optionally having one or more atoms or groups selected from the group consisting of halogen atoms and C1 to C3 alkyl groups" in the present invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of the "C1 to C6 alkoxy groups optionally having one or more halogen atoms" in the present invention include a methoxy group, a trifluoromethoxy group, an ethoxy group, a 2,2,2-trifluoroethoxy group, a propoxy group, an isopropoxy group, a butoxy group, an isobutoxy group, a sec-butoxy group, a tert-butoxy group, a pentyloxy group, and a hexyloxy group.

Examples of the "C1 to C3 alkoxy groups optionally having one or more halogen atoms" in the present invention include a methoxy group, a trifluoromethoxy group, an ethoxy group, a 2,2,2-trifluoroethoxy group, a propoxy group, and an isopropoxy group.

Examples of the "C1 to C6 alkylsulfanyl groups optionally having one or more halogen atoms" in the present invention include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

Examples of the "C1 to C3 alkylsulfanyl groups optionally having one or more halogen atoms" in the present invention include a methylsulfanyl group, an ethylsulfanyl group, a propylsulfanyl group, an isopropylsulfanyl group, a trifluoromethylsulfanyl group, and a 2,2,2-trifluoroethylsulfanyl group.

Examples of the "C1 to C6 alkylsulfinyl groups optionally having one or more halogen atoms" in the present invention include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

Examples of the "C1 to C3 alkylsulfinyl groups optionally having one or more halogen atoms" in the present invention include a methylsulfinyl group, an ethylsulfinyl group, a propylsulfinyl group, an isopropylsulfinyl group, a trifluoromethylsulfinyl group, and a 2,2,2-trifluoroethylsulfinyl group.

Examples of the "C1 to C6 alkylsulfonyl groups optionally having one or more halogen atoms" in the present invention include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

Examples of the "C1 to C3 alkylsulfonyl groups optionally having one or more halogen atoms" in the present invention include a methylsulfonyl group, an ethylsulfonyl group, a propylsulfonyl group, an isopropylsulfonyl group, a trifluoromethylsulfonyl group, and a 2,2,2-trifluoroethylsulfonyl group.

Examples of the "C1 to C6 alkylamino groups optionally having one or more halogen atoms" in the present invention include a methylamino group, an ethylamino group, a 2,2,2-trifluoroethylamino group, a propylamino group, an isopropylamino group, and a butylamino group.

Examples of the "C2 to C8 dialkylamino groups optionally having one or more halogen atoms" in the present invention include a dimethylamino group, a diethylamino group, a bis(2,2,2-trifluoroethyl)amino group, and a dipropylamino group.

Examples of the "C2 to C6 alkylcarbonylamino groups optionally having one or more halogen atoms" in the present invention include an acetylamino group, a propionylamino group, a butyrylamino group, a pentanoylamino group, a hexanoylamino group, and a trifluoroacetylamino group.

Examples of the "C2 to C6 alkoxycarbonylamino groups optionally having one or more halogen atoms" in the present invention include a methoxycarbonylamino group, an ethoxycarbonylamino group, a propoxycarbonylamino group, a butoxycarbonylamino group, a pentyloxycarbonylamino group, a tert-butoxycarbonylamino group, and a 2,2,2-trifluoroethyloxycarbonylamino group.

Examples of the "C1 to C3 alkylsulfonylamino groups optionally having one or more halogen atoms" in the present invention include a methylsulfonylamino group, an ethylsulfonylamino group, a propylsulfonylamino group, an isopropylsulfonylamino group, a trifluoromethylsulfonylamino group, and a 2,2,2-trifluoroethylsulfonylamino group.

Examples of the "C2 to C6 alkylcarbonyl groups optionally having one or more halogen atoms" in the present invention include an acetyl group, a propionyl group, a butyryl group, a pentanoyl group, a hexanoyl group, and a trifluoroacetyl group.

Examples of the "C2 to C6 alkoxycarbonyl groups optionally having one or more halogen atoms" in the present invention include a methoxycarbonyl group, an ethoxycarbonyl group, a propoxycarbonyl group, a butoxycarbonyl group, a pentyloxycarbonyl group, a tert-butoxycarbonyl group, and a 2,2,2-trifluoroethyloxycarbonyl group.

Examples of the "C1 to C6 alkylaminocarbonyl groups optionally having one or more halogen atoms" in the present invention include a methylaminocarbonyl group, an ethylaminocarbonyl group, a 2,2,2-trifluoroethylaminocarbonyl group, a propylaminocarbonyl group, an isopropylaminocarbonyl group, and a butylaminocarbonyl group.

Examples of the "C3 to C8 dialkylaminocarbonyl groups optionally having one or more halogen atoms" in the present invention include a dimethylaminocarbonyl group, a diethylaminocarbonyl group, a bis(2,2,2-trifluoroethyl)aminocarbonyl group, and a dipropylaminocarbonyl group.

Examples of the "C1 to C6 alkyl group optionally having one or more atoms or groups selected from the group consisting of halogen atoms and cyclopropyl groups (wherein the cyclopropyl group may have one or more halogen atoms or one or more C1 to C3 alkyl groups)" in the present invention include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2,-trifluoroethyl group, a pentafluoroethyl group, a heptafluoroisopropyl group, a cyclopropylmethyl group, a 2-cyclopropylethyl group, a 1-cyclopropylethyl group, a 1-methylcyclopropylmethyl group, a 2,2-dimethylcyclopropylmethyl group, and a 2,2-difluorocyclopropylmethyl group.

Examples of the "C2 to C6 alkyl group optionally having one or more atoms or groups selected from the group consisting of halogen atoms and cyclopropyl groups (wherein the cyclopropyl group may have one or more halogen atoms or one or more C1 to C3 alkyl groups)" in the present invention include an ethyl group, a propyl group, an isopropyl group, a butyl group, an isobutyl group, a sec-butyl group, a tert-butyl group, a pentyl group, a neopentyl group, a hexyl group, a 2-fluoroethyl group, a 2,2-difluoroethyl group, a 2,2,2,-trifluoroethyl group, a pentafluoroethyl group, a heptafluoroisopropyl group, a 2-cyclopropylethyl group, a 1-cyclopropylethyl group, and a 2-(2,2-difluorocyclopropyl)ethyl group.

Examples of the "(C3 to C6 cycloalkyl)C1 to C3 alkyl groups optionally having one or more halogen atoms" in the present invention include a cyclopropylmethyl group, a 2-cyclopropylethyl group, a 1-cyclopropylethyl group, and a 2,2-difluorocyclopropylmethyl group.

Examples of the "C3 to C6 cycloalkyl group optionally having one or more atoms or groups selected from the group consisting of halogen atoms and C1 to C3 alkyl groups" in the present invention include a cyclopropyl group, a cyclobutyl group, a cyclopentyl group, a cyclohexyl group, a 1-methylcyclohexyl group, a 2-methylcyclohexyl group, a 3-methylcyclohexyl group, a 4-methylcyclohexyl group, a 1-fluorocyclohexyl group, a 2-fluorocyclohexyl group, a 3-fluorocyclohexyl group, and a 4-fluorocyclohexyl group.

The notation of the "phenyl group optionally having one or more atoms or groups selected from group Z" in the present invention represents a phenyl group in which a hydrogen atom bound to the carbon atom is optionally substituted by an atom or group selected from group Z, and at that time, when having two or more atoms or groups selected from group Z, the atoms or groups selected from group Z may be the same or different from each other.

Examples of the "phenyl group optionally having one or more atoms or groups selected from group Z" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

The "heterocyclic group" in the present invention represents a heterocyclic compound residue containing one or more nitrogen atoms, oxygen atoms or sulfur atoms, other than carbon atoms, as ring-constituting atoms, in the ring structure.

In addition, in the present invention, a 5-membered heterocyclic group means a 5-membered aromatic heterocyclic group or a 5-membered nonaromatic heterocyclic group, and a 6-membered heterocyclic group means a 6-membered aromatic heterocyclic group or a 6-membered nonaromatic heterocyclic group.

The "heterocyclic group" in the "5- or 6-membered heterocyclic group optionally having one or more atoms or groups selected from group Z" in the present invention represents a heterocyclic compound residue containing one or more nitrogen atoms, oxygen atoms or sulfur atoms, other than carbon atoms, in the ring structure, and at that time, when having two or more atoms or groups selected from group Z, the atoms or groups selected from group Z may be the same or different from each other.

In addition, in the present invention, a 5- or 6-membered heterocyclic group means a 5- or 6-membered aromatic heterocyclic group or a 5- or 6-membered nonaromatic heterocyclic group.

Examples of the "5- or 6-membered heterocyclic group optionally having one or more atoms or groups selected from group Z" include 5- or 6-membered nonaromatic heterocyclic groups optionally having one or more atoms or groups selected from group Z such as a pyrrolidin-1-yl group, a 3,3,4,4-tetrafluoropyrrolidin-1-yl group, a tetrahydrofuran-2-yl group, a piperidyl group, a morpholinyl group and a thiomorpholinyl group; and 5- or 6-membered aromatic heterocyclic groups optionally having one or more atoms or groups selected from group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

Examples of the "phenyl group (wherein the phenyl group optionally has one or more atoms or groups selected from the group consisting of C1 to C3 alkyl groups optionally having one or more halogen atoms and halogen atoms)" in the present invention include a phenyl group, a 2-fluorophenyl group, a 3-fluorophenyl group, a 4-fluorophenyl group, a 2,3-difluorophenyl group, a 2,4-difluorophenyl group, a 2,5- difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, and a 4-trifluoromethylphenyl group.

Examples of the "5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms)" the present invention include 5- or 6-membered nonaromatic heterocyclic groups such as a pyrrolidin-1-yl group, a 3,3,4,4-tetrafluoropyrrolidin-1-yl group, a tetrahydrofuran-2-yl group, a piperidyl group, a morpholinyl group and a thiomorpholinyl group; and 5- or 6-membered aromatic heterocyclic groups such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 5-bromo-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

Examples of the "C1 to C6 chain hydrocarbon group having one phenyl group (wherein the phenyl group may have one or more atoms or groups selected from group Z)" in the present invention include a phenylmethyl group, a 4-chlorophenylmethyl group, and a 4-trifluoromethylphenylmethyl group. At that time, when having two or more atoms or groups selected from group Z, the atoms or groups selected from group Z may be the same or different from each other.

Examples of the "C1 to C6 alkyl group optionally having one thiazolyl group (wherein the thiazolyl group optionally has one or more atoms or groups selected from the group consisting of C1 to C3 alkyl groups optionally having one or more halogen atoms and halogen atoms)" in the present invention include a (thiazol-5-yl)methyl group, a (2-chlorothiazol-5-yl)methyl group, and a 1-(2-chlorothiazol-5-yl)ethyl group.

Examples of the "C1 to C6 alkyl group optionally having one pyridyl group (wherein the pyridyl group optionally has one or more atoms or groups selected from the group consisting of C1 to C3 alkyl groups optionally having one or more halogen atoms and halogen atoms)" in the present invention include a (pyridin-5-yl)methyl group, a (2-chloropyridin-5-yl)methyl group, a 1-(2-chloropyridin-5-yl)ethyl group, and a (2-trifluoromethylpyridin-5-yl)methyl group.

Examples of the "pyridyl group (wherein the pyridyl group optionally has one or more atoms or groups selected from the group consisting of C1 to C3 alkyl groups optionally having one or more halogen atoms and halogen atoms)" in the present invention include a 2-pyridyl group, a 3-pyridyl group, a 4-pyridyl group, a 5-trifluoromethyl-2-pyridyl group, and a 3-chloro-5-trifluoromethyl-2-pyridyl group.

Examples of the "pyrimidinyl group (wherein the pyrimidinyl group optionally has one or more atoms or groups selected from the group consisting of C1 to C3 alkyl groups optionally having one or more halogen atoms and halogen atoms)" in the present invention include a 2-pyrimidinyl group, a 4-pyrimidinyl group, a 5-pyrimidinyl group, and a 2-chloro-4-pyrimidinyl group.

Examples of the compound of the present invention include the following compounds.

In the formula (1), compounds wherein $R^1$ is a C1 to C6 chain hydrocarbon group optionally having one or more atoms or groups selected from group X.

In the formula (1), compounds wherein $R^1$ is a C3 to C6 cycloalkyl group optionally having one or more atoms or groups selected from group Y.

In the formula (1), compounds wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or C3 to C6 cycloalkyl group optionally having one or more atoms or groups selected from the group consisting of halogen atoms and C1 to C3 alkyl groups.

In the formula (1), compounds wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms.

In the formula (1), compounds wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups).

In the formula (1), compounds wherein $R^1$ is a C3 to C6 cycloalkyl group optionally having one or more atoms or groups selected from the group consisting of halogen atoms and C1 to C3 alkyl groups.

In the formula (1), compounds wherein $R^1$ is a C2 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups) or a C3 to C6 cycloalkyl group optionally having one or more atoms or groups selected from the group consisting of halogen atoms and C1 to C3 alkyl groups.

In the formula (1), compounds wherein $R^1$ is a C3 to C6 cycloalkyl group optionally having one or more atoms or groups selected from the group consisting of halogen atoms and C1 to C3 alkyl groups, a C2 to C6 alkyl group optionally having one or more halogen atoms, or a (C3 to C6 cycloalkylalkyl)C1 to C3 alkyl group optionally having one or more halogen atoms.

In the formula (1), compounds wherein $R^1$ is a C2 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups).

In the formula (1), compounds wherein $R^1$ is a C2 to C6 alkyl group, a C2 to C6 alkenyl group, or a C2 to C6 alkynyl group.

In the formula (1), compounds wherein $R^1$ is a C2 to C6 alkyl group, a cyclopropyl group, or a cyclopropylmethyl group.

In the formula (1), compounds wherein $R^1$ is a methyl group, an ethyl group, a propyl group, an isopropyl group, a butyl group, a propargyl group, a trifluoromethyl group, a 2,2,2-trifluoroethyl group, a cyclopropyl group, a cyclobutyl group, a cyclopropylmethyl group, or a cyclobutylmethyl group.

In the formula (1), compounds wherein $R^1$ is an ethyl group, a cyclopropyl group, or a cyclopropylmethyl group.

In the formula (1), compounds wherein $R^1$ is an ethyl group.

In the formula (1), compounds wherein $R^1$ is a cyclopropyl group.

In the formula (1), compounds wherein $R^1$ is a cyclopropylmethyl group.

In the formula (1), compounds wherein $R^2$, $R^3$, $R^4$ and $R^5$ are the same or different and are a C1 to C6 chain hydrocarbon group optionally having one or more atoms or groups selected from group X, a C3 to C6 cycloalkyl group optionally having one or more atoms or groups selected from group Y, or a hydrogen atom.

In the formula (1), compounds wherein $R^2$, $R^3$, $R^4$ and $R^5$ are the same or different and are a phenyl group optionally having one or more atoms or groups selected from group Z, a 5- or 6-membered heterocyclic group optionally having one or more atoms or groups selected from group Z, or a hydrogen atom.

In the formula (1), compounds wherein $R^2$, $R^3$, $R^4$ and R are the same or different and are $-OR^{12}$, $-S(O)_mR^{12}$, $-S(O)_2NR^{12}R^{13}$, $-NR^{12}R^{13}$, $-NR^{12}C(O)R^{13}$, $-NR^{12}CO_2R^{13}$, $-NR^{12}S(O)_2R^{14}$, $-C(O)R^{12}$, $-CO_2R^{12}$, $-C(O)NR^{12}R^{13}$, $-SF_5$, a cyano group, a nitro group, a halogen atom, or a hydrogen atom.

In the formula (1), compounds wherein $R^2$, $R^4$ and $R^5$ are the same or different and are a C1 to C6 alkyl group optionally having one or more halogen atoms, $-OR^{12}$, $-S(O)_mR^{12}$, a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-NR^{12}R^{13}$, $-NR^{12}C(O)R^{13}$, $-NR^{12}CO_2R^{13}$, $-NR^{12}S(O)_2R^{14}$, $-C(O)R^{12}$, $-CO_2R^{12}$, $-C(O)NR^{12}R^{13}$, $-SF_5$, a cyano group, a nitro group, a halogen atom or a hydrogen atom.

In the formula (1), compounds wherein $R^2$, $R^4$ and $R^5$ are the same or different and are a C1 to C6 alkyl group optionally having one or more halogen atoms, $-OR^{12}$, $-S(O)_mR^{12}$, a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-C(O)R^{12}$, $-CO_2R^{12}$, $-C(O)NR^{12}R^{13}$, $-SF_5$, a cyano group, a nitro group or a halogen atom.

In the formula (1), compounds wherein $R^2$, $R^4$ and $R^5$ are the same or different and are a C1 to C6 alkyl group optionally having one or more halogen atoms, $-OR^{12}$, $-S(O)_mR^{12}$, a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-SF_5$, a cyano group, a nitro group, a halogen atom or a hydrogen atom.

In the formula (1), compounds wherein $R^2$, $R^4$ and $R^5$ are the same or different and are a C1 to C6 alkyl group optionally having one or more halogen atoms, $-OR^{12}$, $-S(O)_mR^{12}$, a halogen atom or a hydrogen atom, and $R^3$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-SF_5$, a cyano group, a nitro group, a halogen atom or a hydrogen atom.

In the formula (1), compounds wherein $R^2$, $R^4$ and $R^5$ are the same or different and are a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-NR^{12}R^{13}$, $-NR^{12}C(O)R^{13}$, $-NR^{12}CO_2R^{13}$, $-NR^{12}S(O)_2R^{14}$, $-C(O)R^{12}$, $-CO_2R^{12}$, $-C(O)NR^{12}R^{13}$, $-SF_5$, a cyano group, a nitro group, a halogen atom or a hydrogen atom.

In the formula (1), compounds wherein $R^2$, $R^4$ and $R^5$ are the same or different and are a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-C(O)R^{12}$, $-CO_2R^{12}$, $-C(O)NR^{12}R^{13}$, $-SF_5$, a cyano group, a nitro group, a halogen atom or a hydrogen atom.

In the formula (1), compounds wherein $R^2$, $R^4$ and $R^5$ are the same or different and are a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, —$OR^{12}$, —$S(O)_mR^{12}$, —$C(O)R^{12}$, —$CO_2R^{12}$, —$C(O)NR^{12}R^{13}$, —$SF_5$, a cyano group, a nitro group or a halogen atom.

In the formula (1), compounds wherein $R^2$, $R^4$ and $R^5$ are the same or different and are a halogen atom or a hydrogen atom, and $R^3$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, —$OR^{12}$, —$S(O)_mR^{12}$, —$SF_5$, a cyano group, a nitro group, a halogen atom or a hydrogen atom.

In the formula (1), compounds wherein $R^2$, $R^4$ and $R^5$ are the same or different and are a halogen atom or a hydrogen atom, and $R^3$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, —$OR^{12}$, —$S(O)_mR^{12}$, —$SF_5$, a cyano group, a nitro group or a halogen atom.

In the formula (1), compounds wherein $R^2$, $R^4$ and $R^5$ are the same or different and are a halogen atom or a hydrogen atom, and $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of halogen atoms and C1 to C3 alkyl groups optionally having one or more halogen atoms), —$OR^{12}$, —$S(O)_mR^{12}$, a halogen atom or a hydrogen atom.

In the formula (1), compounds wherein $R^2$, $R^4$ and $R^5$ are the same or different and are a halogen atom or a hydrogen atom, and $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of halogen atoms and C1 to C3 alkyl groups optionally having one or more halogen atoms), —$OR^{12}$, —$S(O)_mR^{12}$ or a halogen atom.

In the formula (1), compounds wherein $R^2$, $R^4$ and $R^5$ are a hydrogen atom, and $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more halogen atoms or a C1 to C3 alkyl group optionally having one or more halogen atoms), —$OR^{12}$, —$S(O)_mR^{12}$, —$NR^{12}R^{13}$, —$NR^{12}C(O)R^{13}$, —$NR^{12}CO_2R^{13}$, —$NR^{12}S(O)_2R^{14}$, a halogen atom or a hydrogen atom.

In the formula (1), compounds wherein $R^2$, $R^4$ and $R^5$ are a hydrogen atom, and $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of halogen atoms and C1 to C3 alkyl groups optionally having one or more halogen atoms), —$OR^{12}$, —$S(O)_mR^{12}$, a halogen atom or a hydrogen atom.

In the formula (1), compounds wherein $R^2$, $R^4$ and $R^5$ are a hydrogen atom, and $R^3$ is a C1 to C6 alkyl group optionally having one or more halogen atoms, a 5- or 6-membered heterocyclic group (wherein the 5- or 6-membered heterocyclic group optionally has one or more atoms or groups selected from the group consisting of halogen atoms and C1 to C3 alkyl groups optionally having one or more halogen atoms), —$OR^{12}$, —$S(O)_mR^{12}$, a halogen atom or a hydrogen atom.

In the formula (1), compounds wherein $R^2$, $R^4$ and $R^5$ are a hydrogen atom, and $R^3$ is a C1 to C6 alkyl group optionally having one or more halogen atoms, a 5- or 6-membered heterocyclic group (wherein the 5- or 6-membered heterocyclic group optionally has one or more atoms or groups selected from the group consisting of halogen atoms and C1 to C3 alkyl groups optionally having one or more halogen atoms), —$OR^{12}$, —$S(O)_mR^{12}$, a halogen atom or a hydrogen atom.

In the formula (1), compounds wherein $R^2$, $R^4$ and $R^5$ are a hydrogen atom, and $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or substituents selected from the group consisting of halogen atoms and C1 to C3 alkyl groups optionally having one or more halogen atoms), a pyrimidinyl group (wherein the pyrimidinyl group optionally has one or more atoms or substituents selected from the group consisting of halogen atoms and C1 to C3 alkyl groups optionally having one or more halogen atoms) or a halogen atom.

In the formula (1), compounds wherein $R^2$, $R^4$ and $R^5$ are a hydrogen atom, and $R^3$ is a C1 to C3 alkyl group optionally having one or more halogen atoms.

In the formula (1), compounds wherein $R^2$, $R^4$ and $R^5$ are a hydrogen atom, and $R^3$ is a C1 to C3 alkoxy group optionally having one or more halogen atoms.

In the formula (1), compounds wherein $R^2$, $R^4$ and $R^5$ are a hydrogen atom, and $R^3$ is a C1 to C3 alkylsulfanyl group optionally having one or more halogen atoms, a C1 to C3 alkylsulfinyl group optionally having one or more halogen atoms or a C1 to C3 alkylsulfonyl group optionally having one or more halogen atoms.

In the formula (1), compounds wherein $R^2$, $R^4$ and $R^5$ are a hydrogen atom, and $R^3$ is a C1 to C6 alkylamino group optionally having one or more halogen atoms.

In the formula (1), compounds wherein $R^2$, $R^4$ and $R^5$ are a hydrogen atom, and $R^3$ is a C2 to C8 dialkylamino group optionally having one or more halogen atoms.

In the formula (1), compounds wherein $R^2$, $R^4$ and $R^5$ are a hydrogen atom, and $R^3$ is a C2 to C6 alkylcarbonylamino group optionally having one or more halogen atoms.

In the formula (1), compounds wherein $R^2$, $R^4$ and $R^5$ are a hydrogen atom, and $R^3$ is a C2 to C6 alkoxycarbonylamino group optionally having one or more halogen atoms.

In the formula (1), compounds wherein $R^2$, $R^4$ and $R^5$ are a hydrogen atom, and $R^3$ is a C2 to C6 alkylcarbonyl group optionally having one or more halogen atoms.

In the formula (1), compounds wherein $R^2$, $R^4$ and $R^5$ are a hydrogen atom, and $R^3$ is a C2 to C6 alkoxycarbonyl group optionally having one or more halogen atoms.

In the formula (1), compounds wherein $R^2$, $R^4$ and $R^5$ are a hydrogen atom, and $R^3$ is a C1 to C3 alkylsulfonylamino group optionally having one or more halogen atoms.

In the formula (1), compounds wherein $R^2$, $R^4$ and $R^5$ are a hydrogen atom, and $R^3$ is an amino group.

In the formula (1), compounds wherein $R^2$, $R^4$ and $R^5$ are a hydrogen atom, and $R^3$ is a C2 to C6 alkylaminocarbonyl group optionally having one or more halogen atoms.

In the formula (1), compounds wherein $R^2$, $R^4$ and $R^5$ are a hydrogen atom, and $R^3$ is a C3 to C8 dialkylaminocarbonyl group optionally having one or more halogen atoms.

In the formula (1), compounds wherein $R^2$, $R^4$ and $R^5$ are a hydrogen atom, and $R^3$ is an aminocarbonyl group.

In the formula (1), compounds wherein $R^2$, $R^4$ and $R^5$ are a hydrogen atom, and $R^3$ is a pyridyl group (wherein the pyridyl group optionally has one or more atoms or substituents selected from the group consisting of halogen atoms and C1 to C3 alkyl groups optionally having one or more halogen atoms) or a pyrimidinyl group (wherein the pyrimidinyl group optionally has one or more atoms or substituents selected from the group consisting of halogen atoms and C1 to C3 alkyl groups optionally having one or more halogen atoms).

In the formula (1), compounds wherein $R^2$, $R^4$ and $R^5$ are a hydrogen atom, and $R^3$ is a halogen atom.

In the formula (1), compounds wherein $R^2$, $R^4$ and $R^5$ are a hydrogen atom, and $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a 2-pyridyl group, a 2-pyrimidinyl group, a 5-trifluoromethyl-2-pyridyl group, a 3-chloro-5-trifluoromethyl-2-pyridyl group, a fluorine atom, a chlorine atom, a bromine atom or an iodine atom.

In the formula (1), compounds wherein $R^2$, $R^4$ and $R^5$ are a hydrogen atom, and $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, an acetylamino group, a methoxycarbonylamino group, an ethoxycarbonylamino group, a tert-butyloxycarbonylamino group, a methylsulfonylamino group, an amino group, an acetyl group, a methoxycarbonyl group, an ethoxycarbonyl group, a methylaminocarbonyl group, an ethylaminocarbonyl group, a dimethylaminocarbonyl group, a diethylaminocarbonyl group, an aminocarbonyl group, a fluorine atom, a chlorine atom, a bromine atom or an iodine atom.

In the formula (1), compounds wherein $R^2$, $R^4$ and $R^5$ are a hydrogen atom, and $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a fluorine atom, a chlorine atom, a bromine atom or an iodine atom.

In the formula (1), compounds wherein $R^2$, $R^3$, $R^4$ and R are a hydrogen atom.

In the formula (1), compounds wherein $R^2$, $R^4$ and $R^5$ are the same or different and are a C1 to C6 alkyl group optionally having one or more halogen atoms, —$OR^{12}$, —$S(O)_mR^{12}$, a halogen atom, or a hydrogen atom.

In the formula (1), compounds wherein $R^2$, $R^4$ and $R^5$ are the same or different and are a C1 to C6 alkyl group optionally having one or more halogen atoms or a hydrogen atom.

In the formula (1), compounds wherein $R^2$, $R^4$ and $R^5$ are the same or different and are —$OR^{12}$, —$S(O)_mR^{12}$, a halogen atom, or a hydrogen atom.

In the formula (1), compounds wherein $R^2$, $R^4$ and $R^5$ are the same or different and are a halogen atom or a hydrogen atom.

In the formula (1), compounds wherein $R^2$, $R^4$ and $R^5$ are a hydrogen atom.

In the formula (1), compounds wherein $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, —$OR^{12}$, —$S(O)_mR^{12}$, —$C(O)R^{12}$, —$CO_2R^{12}$, —$C(O)NR^{12}R^{13}$, —$SF_5$, a cyano group, a nitro group, a halogen atom, or a hydrogen atom.

In the formula (1), compounds wherein $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, or a 5- or 6-membered heterocyclic group (wherein the 5- or 6-membered heterocyclic group optionally has one or more atoms or groups selected from the group consisting of halogen atoms and C1 to C3 alkyl groups optionally having one or more halogen atoms), —$OR^{12}$, —$S(O)_mR^{12}$, a halogen atom, or a hydrogen atom.

In the formula (1), compounds wherein $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or substituents selected from the group consisting of halogen atoms and C1 to C3 alkyl groups optionally having one or more halogen atoms), a pyrimidinyl group (wherein the pyrimidinyl group optionally has one or more atoms or substituents selected from the group consisting of halogen atoms and C1 to C3 alkyl groups optionally having one or more halogen atoms), a halogen atom, or a hydrogen atom.

In the formula (1), compounds wherein $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or substituents selected from the group consisting of halogen atoms and C1 to C3 alkyl groups optionally having one or more halogen atoms), a pyrimidinyl group (wherein the pyrimidinyl group optionally has one or more atoms or substituents selected from the group consisting of halogen atoms and C1 to C3 alkyl groups optionally having one or more halogen atoms), or a halogen atom.

In the formula (1), compounds wherein $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom), a pyrimidinyl group (wherein the pyrimidinyl group optionally has one or more atoms or substituents selected from the group consisting of halogen atoms, C1 to C3 alkyl groups optionally having a halogen atom, and C1 to C3 alkoxy groups optionally having a halogen atom), a halogen atom, or a hydrogen atom.

In the formula (1), compounds wherein $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom), a pyrimidinyl group (wherein the pyrimidinyl group optionally has one or more atoms or substituents selected from the group consisting of halogen atoms, C1 to C3 alkyl groups optionally having a halogen atom, and C1 to C3 alkoxy groups optionally having a halogen atom), a halogen atom, or a hydrogen atom.

In the formula (1), compounds wherein $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a 2-pyridyl group, a 2-pyrimidinyl group, a 5-trifluoromethyl-2-pyridyl group, a 3-chloro-5-trifluoromethyl-2-pyridyl group, a fluorine atom, a chlorine atom, a bromine atom, or an iodine atom.

In the formula (1), compounds wherein $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, an acetylamino group, a methoxycarbonylamino group, an ethoxycarbonylamino group, a tert-butyloxycarbonylamino group, a methylsulfonylamino group, an amino group, an acetyl group, a methoxycarbonyl group, an ethoxycarbonyl group, a methylaminocarbonyl group, an ethylaminocarbonyl group, a dimethylaminocarbonyl group, a diethylaminocarbonyl group, an aminocarbonyl group, a fluorine atom, a chlorine atom, a bromine atom, or an iodine atom.

In the formula (1), compounds wherein $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a fluorine atom, a chlorine atom, a bromine atom, or an iodine atom.

In the formula (1), compounds wherein $R^6$ is a C1 to C6 chain hydrocarbon group optionally having one or more atoms or groups selected from group W or a C3 to C6 cycloalkyl group optionally having one or more atoms or groups selected from group Y.

In the formula (1), compounds wherein $R^6$ is a C1 to C6 alkyl group having one phenyl group (wherein the phenyl group optionally has one or more atoms or groups selected from group Z) or a C1 to C6 alkyl group having one 5- or 6-membered heterocyclic group (wherein the 5- or 6-membered heterocyclic group optionally has one or more atoms or groups selected from group Z).

In the formula (1), compounds wherein $R^6$ is a —C(O)$R^{12}$, C(O)O$R^{12}$, or —C(O)N$R^{12}R^{13}$.

In the formula (1), compounds wherein $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or substituents selected from the group consisting of C1 to C3 alkyl groups optionally having one or more halogen atoms and halogen atoms), a (C1 to C6 alkoxy)C1 to C6 alkyl group optionally having one or more halogen atoms, —C(O)$R^{12}$, or —C(O)O$R^{12}$.

In the formula (1), compounds wherein $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms.

In the formula (1), compounds wherein $R^6$ is a C1 to C6 alkyl group having one thiazolyl group (wherein the thiazolyl group optionally has one or more atoms or substituents selected from the group consisting of C1 to C3 alkyl groups optionally having one or more halogen atoms and halogen atoms) or a C1 to C6 alkyl group having one pyridyl group (wherein the pyridyl group optionally has one or more atoms or substituents selected from the group consisting of C1 to C3 alkyl groups optionally having one or more halogen atoms and halogen atoms).

In the formula (1), compounds wherein $R^6$ is a (C1 to C6 alkoxy)C1 to C6 alkyl group optionally having one or more halogen atoms, $-C(O)R^{12}$, or $-C(O)OR^{12}$.

In the formula (1), compounds wherein $R^6$ is a C1 to C6 alkyl group optionally having one or more halogen atoms, a C2 to C6 alkenyl group optionally having one or more halogen atoms, or a C2 to C6 alkynyl group optionally having one or more halogen atoms.

In the formula (1), compounds wherein $R^6$ is a C1 to C6 alkyl group, a C2 to C6 alkenyl group, or a C2 to C6 alkynyl group, a (C1 to C6 alkoxy)C1 to C6 alkyl group, $-C(O)R^{12}$, or $-C(O)OR^{12}$.

In the formula (1), compounds wherein $R^6$ is a C1 to C6 alkyl group, a C2 to C6 alkenyl group, or a C2 to C6 alkynyl group.

In the formula (1), compounds wherein $R^6$ is a C1 to C6 alkyl group optionally having one or more atoms or groups selected from the group consisting of halogen atoms and cyclopropyl groups or a propargyl group.

In the formula (1), compounds wherein $R^6$ is a C1 to C6 alkyl group optionally having one or more atoms or groups selected from the group consisting of halogen atoms and cyclopropyl groups.

In the formula (1), compounds wherein $R^6$ is a methyl group, an ethyl group, a propyl group, an isopropyl group, a butyl group, an isobutyl group, a hexyl group, a propargyl group, a cyclopropyl group, a cyclobutyl group, a cyclohexyl group, a cyclopropylmethyl group, a cyclobutylmethyl group, a 2,2,2-trifluoroethyl group, a benzyl group, a 6-chloropyridin-3-ylmethyl group, a 2-chlorothiazolyl-5-ylmethyl group, a methoxymethyl group, an ethoxymethyl group, a methoxycarbonyl group, or an ethoxycarbonyl group.

In the formula (1), compounds wherein $R^6$ is a methyl group, an ethyl group, a propyl group, an isopropyl group, a butyl group, an isobutyl group, a hexyl group, a propargyl group, a cyclopropyl group, a cyclobutyl group, a cyclohexyl group, a cyclopropylmethyl group, a cyclobutylmethyl group, a 2,2,2-trifluoroethyl group, a benzyl group, a 6-chloropyridin-3-ylmethyl group, or a 2-chlorothiazolyl-5-ylmethyl group.

In the formula (1), compounds wherein $R^6$ is a methyl group, an ethyl group, a propyl group, an isopropyl group, a butyl group, an isobutyl group, or a hexyl group.

In the formula (1), compounds wherein $R^6$ is a cyclopropyl group, a cyclobutyl group, a cyclohexyl group, a cyclopropylmethyl group, or a cyclobutylmethyl group.

In the formula (1), compounds wherein $R^6$ is a benzyl group, a 6-chloropyridin-3-ylmethyl group, or a 2-chlorothiazolyl-5-ylmethyl group.

In the formula (1), compounds wherein $R^6$ is a methoxymethyl group, an ethoxymethyl group, a methoxycarbonyl group, or an ethoxycarbonyl group.

In the formula (1), compounds wherein $R^6$ is a methyl group.

In the formula (1), compounds wherein $R^6$ is an ethyl group.

In the formula (1), compounds wherein $R^6$ is a cyclopropylmethyl group.

In the formula (1), compounds wherein $R^7$ and $R^{11}$ are the same or different and are a C1 to C6 chain hydrocarbon group optionally having one or more atoms or groups selected from group X or a hydrogen atom.

In the formula (1), compounds wherein $R^7$ and $R^{11}$ are the same or different and are a C1 to C6 chain hydrocarbon group optionally having one or more atoms or groups selected from group X, $-OR^{16}$, $-S(O)_mR^{16}$, a fluorine atom, or a hydrogen atom.

In the formula (1), compounds wherein $R^7$ and $R^{11}$ are the same or different and are a C1 to C6 alkyl group optionally having one or more halogen atoms, $-OR^{16}$, $-S(O)_mR^{16}$, a fluorine atom, or a hydrogen atom.

In the formula (1), compounds wherein $R^7$ and $R^{11}$ are the same or different and are a fluorine atom or a hydrogen atom.

In the formula (1), compounds wherein $R^7$ and $R^{11}$ are a hydrogen atom.

In the formula (1), compounds wherein $R^8$, $R^9$ and $R^{10}$ are the same or different and are a C1 to C6 chain hydrocarbon group optionally having one or more atoms or groups selected from group X, $-OR^{12}$, $-S(O)_mR^{12}$, $-SF_5$, a halogen atom, or a hydrogen atom.

In the formula (1), compounds wherein $R^8$, $R^9$ and $R^{10}$ are the same or different and are a phenyl group optionally having one or more atoms or groups selected from group Z, a 5- or 6-membered heterocyclic group optionally having one or more atoms or groups selected from group Z, or a hydrogen atom.

In the formula (1), compounds wherein $R^8$, $R^9$ and $R^{10}$ are the same or different and are a C1 to C6 chain hydrocarbon group optionally having one or more atoms or groups selected from group X, a halogen atom, or a hydrogen atom.

In the formula (1), compounds wherein $R^8$, $R^9$ and $R^{10}$ are the same or different and are $-OR^{12}$, $-S(O)_mR^{12}$, a halogen atom, or a hydrogen atom.

In the formula (1), compounds wherein $R^8$, $R^9$ and $R^{10}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, $-OR^{12}$, $-S(O)_mR^{12}$, a halogen atom, or a hydrogen atom.

In the formula (1), compounds wherein $R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom, or a hydrogen atom.

In the formula (1), compounds wherein $R^8$, $R^9$ and $R^{10}$ are the same or different and are a C1 to C2 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom, or a hydrogen atom.

In the formula (1), compounds wherein $R^8$, $R^9$ and $R^{10}$ are the same or different and are a C1 to C2 haloalkyl group, a C2 to C6 haloalkenyl group, a C1 to C6 haloalkylsulfanyl group, a C1 to C6 haloalkylsulfinyl group, a C1 to C6 haloalkylsulfonyl group, a halogen atom, or a hydrogen atom.

In the formula (1), compounds wherein $R^8$, $R^9$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom, or a hydrogen atom.

In the formula (1), compounds wherein $R^8$, $R^9$ and $R^{10}$ are the same or different and are a C1 to C2 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom, or a hydrogen atom.

In the formula (1), compounds wherein $R^8$, $R^9$ and $R^{10}$ are the same or different and are a C1 to C2 perfluoroalkyl group, a C1 to C3 perfluoroalkylsulfanyl group, a C1 to C3 perfluoroalkylsulfinyl group, a C1 to C3 perfluoroalkylsulfonyl group, a halogen atom, or a hydrogen atom.

In the formula (1), compounds wherein $R^8$, $R^9$ and $R^{10}$ are the same or different and are a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, a fluorine atom, a chlorine atom, a bromine atom, or a hydrogen atom.

In the formula (1), compounds wherein $R^8$, $R^9$ and $R^{10}$ are the same or different and are a trifluoromethyl group, a pentafluoroethyl group, a trifluoromethoxy group, a trifluoromethylsulfanyl group, a trifluoromethylsulfinyl group or a trifluoromethylsulfonyl group, a fluorine atom, a chlorine atom, a bromine atom, or a hydrogen atom.

In the formula (1), compounds wherein $R^8$, $R^9$ and $R^{10}$ are the same or different and are a trifluoromethyl group, a pentafluoroethyl group, a trifluoromethylsulfanyl group, a trifluoromethylsulfinyl group or a trifluoromethylsulfonyl group, a fluorine atom, a chlorine atom, a bromine atom, or a hydrogen atom.

In the formula (1), compounds wherein $R^7$ and $R^{11}$ are the same or different and are a C1 to C6 alkyl group optionally having one or more halogen atoms, $-OR^{16}$, $-S(O)_mR^{16}$, a fluorine atom or a hydrogen atom, and $R^8$, $R^9$ and $R^{10}$ are the same or different and are a C1 to C6 chain hydrocarbon group optionally having one or more atoms or groups selected from group X, $-OR^{12}$, $-S(O)_mR^{12}$, $-SF_5$, a halogen atom or a hydrogen atom.

In the formula (1), compounds wherein $R^7$ and $R^{11}$ are the same or different and are a fluorine atom or a hydrogen atom, and $R^8$, $R^9$ and $R^{10}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, $-OR^{12}$, $-S(O)_mR^{12}$, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-S(O)_2NR^{12}R^{13}$, $-NR^{12}R^{13}$, $-NR^{12}C(O)R^{13}$, $-NR^{12}CO_2R^{13}$, $-NR^{12}S(O)_2R^{14}$, $-C(O)R^{12}$, $-CO_2R^{14}$, $-C(O)NR^{12}R^{13}$, $-SF_5$, a cyano group, a nitro group, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C6 chain hydrocarbon group optionally having one or more atoms or groups selected from group X, $-OR^{12}$, $-S(O)_mR^{12}$, $-SF_5$, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C2 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C2 haloalkyl group, a C2 to C6 haloalkenyl group, a C1 to C6 haloalkylsulfanyl group, a C1 to C6 haloalkylsulfinyl group, a C1 to C6 haloalkylsulfonyl group, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C2 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein $R^7$ and $R^{11}$ are a hydrogen atom, and $R^8$, $R^9$ and $R^{10}$ are the same or different and are a C1 to C2 perfluoroalkyl group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein $R^7$ and $R^{11}$ are a hydrogen atom, and $R^8$, $R^9$ and $R^{10}$ are the same or different and are a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a fluorine atom, a chlorine atom, a bromine atom or a hydrogen atom.

In the formula (1), compounds wherein $R^7$ and $R^{11}$ are a hydrogen atom, and $R^8$, $R^9$ and $R^{10}$ are the same or different and are a trifluoromethyl group, a pentafluoroethyl group, a trifluoromethoxy group, a trifluoromethylsulfanyl group, a trifluoromethylsulfinyl group, a trifluoromethylsulfonyl group, a fluorine atom, a chlorine atom, a bromine atom or a hydrogen atom.

In the formula (1), compounds wherein $R^7$ and $R^{11}$ are a hydrogen atom, and $R^8$, $R^9$ and $R^{10}$ are the same or different and are a trifluoromethyl group, a pentafluoroethyl group, a trifluoromethylsulfanyl group, a trifluoromethylsulfinyl group or a trifluoromethylsulfonyl group, a fluorine atom, a chlorine atom, a bromine atom or a hydrogen atom.

In the formula (1), compounds wherein $R^7$ and $R^{11}$ are a hydrogen atom, and $R^8$, $R^9$ and $R^{10}$ are the same or different and are a pentafluoroethyl group, a heptafluoroisopropyl group, a trifluoromethoxy group, a trifluoromethylsulfanyl group, a trifluoromethylsulfinyl group, a trifluoromethylsulfonyl group or a hydrogen atom.

In the formula (1), compounds wherein $R^7$ and $R^{11}$ are a hydrogen atom, and $R^8$, $R^9$ and $R^{10}$ are the same or different and are a pentafluoroethyl group, a trifluoromethoxy group, a trifluoromethylsulfanyl group, a trifluoromethylsulfinyl group, a trifluoromethylsulfonyl group or a hydrogen atom.

In the formula (1), compounds wherein $R^7$ and $R^{11}$ are a hydrogen atom, and $R^8$, $R^9$ and $R^{10}$ are the same or different and are a pentafluoroethyl group, a trifluoromethylsulfanyl group, a trifluoromethylsulfinyl group, a trifluoromethylsulfonyl group or a hydrogen atom.

In the formula (1), compounds wherein $R^7$, $R^8$, $R^{10}$ and $R^{11}$ are a hydrogen atom.

In the formula (1), compounds wherein $R^7$, $R^9$ and $R^{11}$ are a hydrogen atom.

In the formula (1), compounds wherein $R^7$, $R^8$, $R^{10}$ and $R^{11}$ are a hydrogen atom, and $R^9$ is a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group or a halogen atom.

In the formula (1), compounds wherein $R^7$, $R^9$ and $R^{11}$ are a hydrogen atom, and $R^8$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein $G^1$ is a nitrogen atom, $G^2$ is =CR$^8$—, $G^3$ is =CR$^9$—, $G^4$ is =CR$^{10}$—, and $G^5$ is =CR$^{11}$—.

In the formula (1), compounds wherein $G^1$ is =CR$^7$—, $G^2$ is a nitrogen atom, $G^3$ is =CR$^9$—, $G^4$ is =CR$^{10}$—, and $G^5$ is =CR$^{11}$—.

In the formula (1), compounds wherein $G^1$ is =CR$^7$—, $G^2$ is =CR$^8$—, $G^3$ is a nitrogen atom, $G^4$ is =CR$^{10}$—, and $G^5$ is =CR$^{11}$—.

In the formula (1), compounds wherein $G^1$ is a nitrogen atom, $G^2$ is =CR$^8$—, $G^3$ is a nitrogen atom, $G^4$ is =CR$^{10}$—, and $G^5$ is =CR$^{11}$—.

In the formula (1), compounds wherein $G^1$ is a nitrogen atom, $G^2$ is CR$^8$—, $G^3$ is =CR$^9$—, $G^4$ is =CR$^{10}$—, and $G^5$ is a nitrogen atom.

In the formula (1), compounds wherein $G^1$ is =CR$^7$—, $G^2$ is a nitrogen atom, $G^3$ is =CR$^9$—, $G^4$ is a nitrogen atom, and $G^5$ is =CR$^{11}$—.

In the formula (1), compounds wherein $G^1$ is a nitrogen atom, $G^2$ is a nitrogen atom, $G^3$ is =CR$^9$—, $G^4$ is =CR$^{10}$—, and $G^5$ is =CR$^{11}$—.

In the formula (1), compounds wherein $G^1$ is =CR$^7$—, $G^2$ is a nitrogen atom, $G^3$ is a nitrogen atom, $G^4$ is =CR$^{10}$—, and $G^5$ is =CR$^{11}$—.

In the formula (1), compounds wherein $G^1$ is a nitrogen atom, $G^2$ is =CR$^8$—, $G^3$ is =CR$^9$—, $G^4$ is a nitrogen atom, and $G^5$ is =CR$^{11}$—.

In the formula (1), compounds wherein one or two of $G^1$, $G^2$, $G^3$, $G^4$ and $G^5$ are a nitrogen atom.

In the formula (1), compounds wherein two of $G^1$, $G^2$, $G^3$, $G^4$ and $G^5$ are a nitrogen atom.

In the formula (1), compounds wherein one of $G^1$, $G^2$, $G^3$, $G^4$ and $G^5$ is a nitrogen atom.

In the formula (1), compounds wherein one or two of $G^1$, $G^2$, $G^4$ and $G^5$ are a nitrogen atom, and $G^3$ is =CR$^9$—.

In the formula (1), compounds wherein $G^1$ is a nitrogen atom.

In the formula (1), compounds wherein $G^2$ is a nitrogen atom.

In the formula (1), compounds wherein $G^3$ is a nitrogen atom.

In the formula (1), compounds wherein $G^4$ is a nitrogen atom.

In the formula (1), compounds wherein $G^5$ is a nitrogen atom.

In the formula (1), compounds wherein $G^1$ is a nitrogen atom or =CR$^7$—, $G^2$ is a nitrogen atom or =CR$^8$—, $G^3$ is =CR$^9$—, $G^4$ is =CR$^{10}$—, and $G^5$ is a nitrogen atom or =CR$^{11}$— (wherein one or two of $G^1$, $G^2$ and $G^5$ represent a nitrogen atom).

In the formula (1), compounds wherein one or two of $G^1$, $G^2$, $G^3$, $G^4$ and $G^5$ are a nitrogen atom, $R^7$ and $R^{11}$ are the same or different and are a C1 to C6 alkyl group optionally having one or more halogen atoms, —OR$^{15}$, —S(O)$_m$R$^{15}$, a fluorine atom, or a hydrogen atom, and $R^8$, $R^9$ and $R^{10}$ are the same or different and are a C1 to C6 chain hydrocarbon group optionally having one or more atoms or groups selected from group X, —OR$^{12}$, —S(O)$_m$R$^{12}$, —SF$_5$, a halogen atom or a hydrogen atom.

In the formula (1), compounds wherein one or two of $G^1$, $G^2$, $G^4$ and $G^5$ are a nitrogen atom, $G^3$ is =CR$^9$—, $R^7$ and $R^{11}$ are the same or different and are a fluorine atom or a hydrogen atom, and $R^8$, $R^9$ and $R^{10}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, —OR$^{12}$, —S(O)$_m$R$^{12}$, a halogen atom or a hydrogen atom.

In the formula (1), compounds wherein $G^1$ is a nitrogen atom or =CR$^7$—, $G^2$ is a nitrogen atom or =CR$^8$—, $G^3$ is =CR$^9$—, $G^4$ is =CR$^{10}$—, $G^5$ is a nitrogen atom or =CR$^{11}$— (wherein one or two of $G^1$, $G^2$ and $G^5$ represent a nitrogen atom), $R^7$ and $R^{11}$ are the same or different and are a fluorine atom or a hydrogen atom, and $R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (1), compounds wherein $G^1$ is a nitrogen atom or =CR$^7$—, $G^2$ is a nitrogen atom or =CR$^8$—, $G^3$ is =CR$^9$—, $G^4$ is =CR$^{10}$—, $G^5$ is a nitrogen atom or =CR$^{11}$— (wherein one or two of $G^1$, $G^2$ and $G^5$ represent a nitrogen atom), $R^7$ and $R^{11}$ are the same or different and are a fluorine atom or a hydrogen atom, and $R^8$, $R^9$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein $G^1$ is a nitrogen atom, $G^2$ is =CR$^8$—, $G^3$ is =CR$^9$—, $G^4$ is =CR$^{10}$—, $G^5$ is =CR$^{11}$—, $R^{11}$ is a fluorine atom or a hydrogen atom, and $R^8$, $R^9$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein Q is an oxygen atom.

In the formula (1), compounds wherein Q is a sulfur atom.

In the formula (1), compounds wherein m is 0.

In the formula (1), compounds wherein m is 1.

In the formula (1), compounds wherein m is 2.

In the formula (1), compounds wherein n is 0.

In the formula (1), compounds wherein n is 1.

In the formula (1), compounds wherein n is 2.

A compound represented by formula (H1):

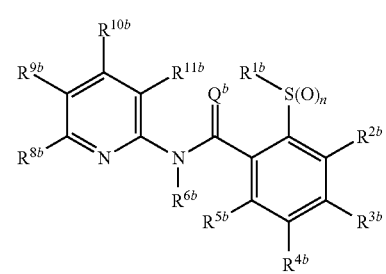

wherein $R^{1b}$ represents C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{b5}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ represents a fluorine atom or a hydrogen atom, $R^{8b}$, $R^{9b}$ and $R^{10b}$ are the same or different and represent a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8b}$, $R^{9b}$ and $R^{10b}$ do not represent a hydrogen atom at the same time), $Q^b$ represents an oxygen atom or a sulfur atom, and n represents 0, 1 or 2, or an N-oxide thereof.

In the formula (H1), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{b5}$ are the same or different and are a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ represents a fluorine atom or a hydrogen atom, $R^{8b}$, $R^{9b}$ and $R^{10b}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8b}$, $R^{9b}$ and $R^{10b}$ do not represent a hydrogen atom at the same time), $Q^b$ is an oxygen atom or a sulfur atom, and n is 0, 1 or 2, or an N-oxide thereof.

In the formula (H1), compounds wherein $R^{1b}$ is a C2 to C3 alkyl group, a cyclopropyl group or a cyclopropylmethyl group, or an N-oxide thereof.

In the formula (H1), compounds wherein $R^{11b}$ is a hydrogen atom, and $R^{8b}$, $R^{9b}$ and $R^{10b}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

A compound represented by formula (H2):

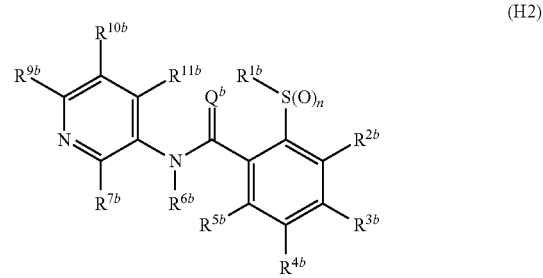

(H2)

wherein $R^{1b}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{7b}$ and $R^{11b}$ are the same or different and represent a fluorine atom or a hydrogen atom, $R^{9b}$ and $R^{10b}$ are the same or different and represent a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ represents an oxygen atom or a sulfur atom, and n represents 0, 1 or 2, or an N-oxide thereof.

In the formula (H2), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and are a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{7b}$ and $R^{11b}$ are the same or different and are a fluorine atom or a hydrogen atom, $R^{9b}$ and $R^{10b}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ is an oxygen atom or a sulfur atom, and n is 0, 1 or 2, or an N-oxide thereof.

In the formula (H2), compounds wherein $R^{1b}$ is a C2 to C3 alkyl group, a cyclopropyl group or a cyclopropylmethyl group, or an N-oxide thereof.

In the formula (H2), compounds wherein $R^{7b}$ and $R^{11b}$ are a hydrogen atom, and $R^{9b}$ and $R^{10b}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

A compound represented by formula (H3):

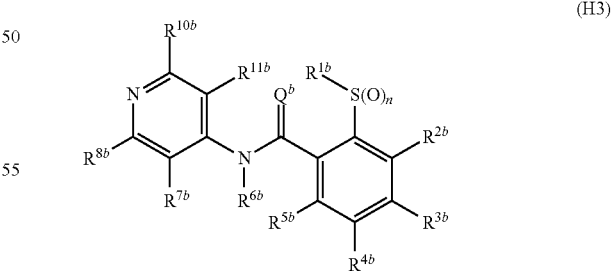

(H3)

wherein $R^{1b}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{7b}$ and $R^{11b}$ are the same or different and represent a fluorine atom or a hydrogen atom, $R^{8b}$ and $R^{10b}$ are the same or different and represent a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ represents an oxygen atom or a sulfur atom, and n represents 0, 1 or 2, or an N-oxide thereof.

In the formula (H3), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and are a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{7b}$ and $R^{10b}$ are the same or different and are a fluorine atom or a hydrogen atom, $R^{8b}$ and $R^{10b}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ is an oxygen atom or a sulfur atom, and n is 0, 1 or 2, or an N-oxide thereof.

In the formula (H3), compounds wherein $R^{1b}$ is a C2 to C3 alkyl group, a cyclopropyl group or a cyclopropylmethyl group, or an N-oxide thereof.

In the formula (H3), compounds wherein $R^{7b}$ and $R^{11b}$ are a hydrogen atom, and $R^{8b}$ and $R^{10b}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

A compound represented by formula (H4):

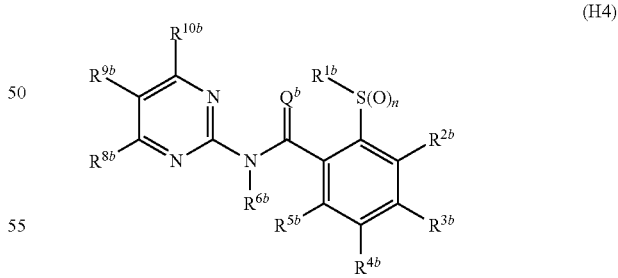

(H4)

wherein $R^{1b}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms, or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{8b}$, $R^{9b}$ and $R^{10b}$ are the same or different and represent a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8b}$, $R^{9b}$ and $R^{10b}$ do not represent a hydrogen atom at the same time), $Q^b$ represents an oxygen atom or a sulfur atom, and n represents 0, 1 or 2, or an N-oxide thereof.

In the formula (H4), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and are a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{8b}$, $R^{9b}$ and $R^{10b}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8b}$, $R^{9b}$ and $R^{10b}$ do not represent a hydrogen atom at the same time), $Q^b$ is an oxygen atom or a sulfur atom, and n is 0, 1 or 2, or an N-oxide thereof.

In the formula (H4), compounds wherein $R^{1b}$ is a C2 to C3 alkyl group, a cyclopropyl group or a cyclopropylmethyl group, or an N-oxide thereof.

In the formula (H4), compounds wherein $R^{8b}$, $R^{9b}$ and $R^{10b}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

A compound represented by formula (H5):

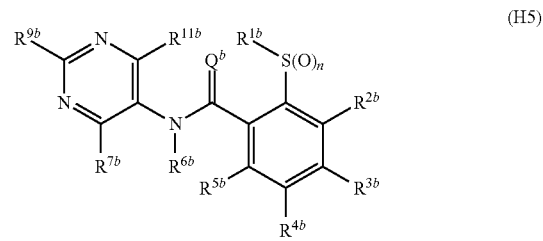

(H5)

wherein $R^{1b}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{7b}$ and $R^{11b}$ are the same or different and are a fluorine atom or a hydrogen atom, $R^{9b}$ represents a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group or a halogen atom, $Q^b$ represents an oxygen atom or a sulfur atom, and n represents 0, 1 or 2, or an N-oxide thereof.

In the formula (H5), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and are a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{7b}$ and $R^{11b}$ are the same or different and are a fluorine atom or a hydrogen atom, $R^{9b}$ is a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group or a halogen atom, $Q^b$ is an oxygen atom or a sulfur atom, and n is 0, 1 or 2, or an N-oxide thereof.

In the formula (H5), compounds wherein $R^{1b}$ is a C2 to C3 alkyl group, a cyclopropyl group or a cyclopropylmethyl group, or an N-oxide thereof.

In the formula (H5), compounds wherein $R^{7b}$ and $R^{11b}$ are a hydrogen atom, and $R^{9b}$ is a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group or a halogen atom, or an N-oxide thereof.

A compound represented by formula (H6):

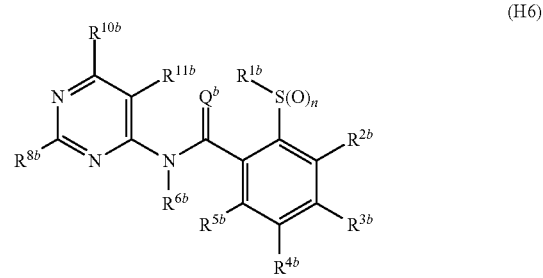

(H6)

wherein $R^{1b}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ represents a fluorine atom or a hydrogen atom, $R^{8b}$ and $R^{10b}$ are the same or different and represent a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ represents an oxygen atom or a sulfur atom, and n represents 0, 1 or 2, or an N-oxide thereof.

In the formula (H6), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or groups selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ is a fluorine atom or a hydrogen atom, $R^{8b}$ and $R^{10b}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ is an oxygen atom or a sulfur atom, and n is 0, 1 or 2, or an N-oxide thereof.

In the formula (H6), compounds wherein $R^{1b}$ is a C2 to C3 alkyl group, a cyclopropyl group or a cyclopropylmethyl group, or an N-oxide thereof.

In the formula (H6), compounds wherein $R^{11b}$ is a hydrogen atom, and $R^{8b}$ and $R^{10b}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

A compound represented by formula (H7):

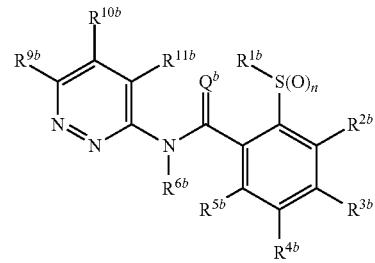

(H7)

wherein $R^{1b}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ represents a fluorine atom or a hydrogen atom, $R^{9b}$ and $R^{10b}$ are the same or different and represent a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ represents an oxygen atom or a sulfur atom, and n represents 0, 1 or 2, or an N-oxide thereof.

In the formula (H7), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and are a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ is a fluorine atom or a hydrogen atom, $R^{9b}$ and $R^{10b}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{9b}$ and $R^{10b}$ do not represent a hydrogen atom at the same time), $Q^b$ is an oxygen atom or a sulfur atom, and n is 0, 1 or 2, or an N-oxide thereof.

In the formula (H7), compounds wherein $R^{1b}$ is a C2 to C3 alkyl group, a cyclopropyl group or a cyclopropylmethyl group, or an N-oxide thereof.

In the formula (H7), compounds wherein $R^{11b}$ is a hydrogen atom, and $R^{9b}$ and $R^{10b}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

A compound represented by formula (H8):

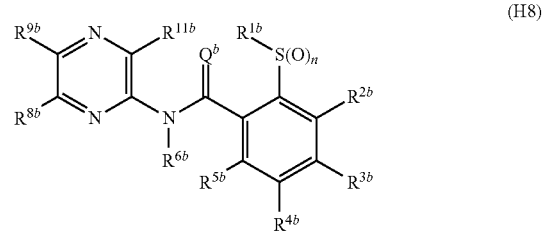

(H8)

wherein $R^{1b}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and represent a halogen atom or a hydrogen atom, $R^{3b}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ represents a fluorine atom or a hydrogen atom, $R^{8b}$ and $R^{9b}$ are the same or different and represent a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8b}$ and $R^{9b}$ do not represent a hydrogen atom at the same time), $Q^b$ represents an oxygen atom or a sulfur atom, and n represents 0, 1 or 2, or an N-oxide thereof.

In the formula (H8), compounds wherein $R^{1b}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkylalkyl)C1 to C3 alkyl group optionally having one or more halogen atoms, $R^{2b}$, $R^{4b}$ and $R^{5b}$ are the same or different and are a halogen atom or a hydrogen atom, $R^{3b}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $R^{6b}$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, $R^{11b}$ is a fluorine atom or a hydrogen atom, $R^{8b}$ and $R^{9b}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8b}$ and $R^{9b}$ do not represent a hydrogen atom at the same time), $Q^b$ is an oxygen atom or a sulfur atom, and n is 0, 1 or 2, or an N-oxide thereof.

In the formula (H8), compounds wherein $R^{1b}$ is a C2 to C3 alkyl group, a cyclopropyl group or a cyclopropylmethyl group, or an N-oxide thereof.

In the formula (H8), compounds wherein $R^{1b}$ is a hydrogen atom, and $R^{8b}$ and $R^{9b}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

In the formula (1), compounds wherein $R^1$ is a C3 to C6 cycloalkyl group optionally having one or more atoms or groups selected from the group consisting of halogen atoms and C1 to C3 alkyl groups, a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms, $R^2$, $R^4$ and $R^5$ are the same or different and are a C1 to C6 alkyl group optionally having one or more halogen atoms, $-OR^{12}$, $-S(O)_mR^{12}$, a halogen atom or a hydrogen atom, $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $-OR^{12}$, $-S(O)_mR^{12}$, $-C(O)R^{12}$, $-CO_2R^{12}$, $-C(O)NR^{12}R^{13}$, $-SF_5$, a cyano group, a nitro group, a halogen atom or a hydrogen atom, $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), a (C1 to C6 alkoxy)C1 to C6 alkyl group optionally having one or more halogen atoms, $-C(O)R^{12}$ or $-C(O)OR^{12}$, one or two of $G^1$, $G^2$, $G^3$, $G^4$ and $G^5$ are a nitrogen atom, $R^7$ and $R^{11}$ are the same or different and are a C1 to C6 alkyl group optionally having one or more halogen atoms, $-OR^{15}$, $-S(O)_mR^{15}$, a fluorine atom or a hydrogen atom, $R^8$, $R^9$ and $R^{10}$ are the same or different and are a C1 to C6 chain hydrocarbon group optionally having one or more atoms or groups selected from group X, $-OR^{12}$, $-S(O)_mR^{12}$, $-SF_5$, a halogen atom or a hydrogen atom, $R^{12}$ and $R^{13}$ are the same or different and are a C1 to C6 alkyl group optionally having one or more halogen atoms, a phenyl group (wherein the phenyl group optionally has a C1 to C3 alkyl group optionally having one or more halogen atoms or one or more halogen atoms), a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms) or a hydrogen atom, and Q is an oxygen atom, or an N-oxide thereof.

In the formula (1), compounds wherein $R^1$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkyl)C1 to C3 alkyl group optionally having one or more halogen atoms, $R^2$, $R^4$ and $R^5$ are the same or different and are a halogen atom or a hydrogen atom, $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), —$OR^{12}$, —$S(O)_mR^{12}$, a halogen atom or a hydrogen atom, $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms or a C2 to C6 alkoxycarbonyl group optionally having one or more halogen atoms, one or two of $G^1$, $G^2$, $G^3$, $G^4$ and $G^5$ are a nitrogen atom, $R^7$ and $R^{11}$ are the same or different and are a fluorine atom or a hydrogen atom, $R^8$, $R^9$ and $R^{10}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, —$OR^{12}$, —$S(O)_mR^{12}$, a halogen atom or a hydrogen atom, $R^{12}$ is a C1 to C6 alkyl group optionally having one or more halogen atoms or a hydrogen atom, and Q is an oxygen atom, or an N-oxide thereof.

In the formula (1), compounds wherein $R^1$ is a C2 to C6 alkyl group, a cyclopropyl group or a cyclopropylmethyl group, $R^2$, $R^4$ and $R^5$ are a hydrogen atom, $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or substituents selected from the group consisting of halogen atoms, and C1 to C3 alkyl groups optionally having one or more halogen atoms), a pyrimidinyl group (wherein the pyrimidinyl group optionally has one or more atoms or substituents selected from the group consisting of halogen atoms and C1 to C3 alkyl groups optionally having one or more halogen atoms), a halogen atom or a hydrogen atom, $R^6$ is a C1 to C6 alkyl group optionally having one or more atoms or groups selected from the group consisting of halogen atoms and cyclopropyl groups, one or two of $G^1$, $G^2$, $G^3$, $G^4$ and $G^5$ are a nitrogen atom, $R^7$ and $R^{11}$ are the same or different and are a fluorine atom or a hydrogen atom, $R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom, and Q is an oxygen atom, or an N-oxide thereof.

In the formula (1), compounds wherein $R^1$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkyl)C1 to C3 alkyl group optionally having one or more halogen atoms, $R^2$, $R^4$ and $R^5$ are the same or different and are a halogen atom or a hydrogen atom, $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $G^1$ is a nitrogen atom or =$CR^7$—,
$G^2$ is a nitrogen atom or =$CR^8$—,
$G^3$ is a nitrogen atom or =$CR^9$—,
$G^4$ is a nitrogen atom or =$CR^{10}$—,
$G^5$ is a nitrogen atom or =$CR^{11}$— (wherein, while at least one of $G^1$, $G^2$, $G^3$, $G^4$ and $G^5$ represents a nitrogen atom, not all of $G^2$, $G^3$ and $G^4$ represent a nitrogen atom), $R^7$ and $R^{11}$ are the same or different and are a fluorine atom or a hydrogen atom, $R^8$, $R^9$ and $R^{10}$ are the same or different and represent a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^8$, $R^9$ and $R^{10}$ do not represent a hydrogen atom at the same time, and at least one of $R^8$, $R^9$ and $R^{10}$ represents a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group or a C1 to C6 haloalkylsulfonyl group, Q is an oxygen atom or a sulfur atom, and n is 0, 1 or 2, or an N-oxide thereof.

In the formula (1), compounds wherein $R^1$ is a C2 to C6 alkyl group, a cyclopropyl group or a cyclopropylmethyl group, $R^2$, $R^4$ and $R^5$ are the same or different and are a halogen atom or a hydrogen atom, $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $G^1$ is a nitrogen atom,
$G^2$ is $=CR^8-$,
$G^3$ is $=CR^9-$,
$G^4$ is $=CR^{10}-$,
$G^5$ is $=CH-$,
$R^8$, $R^9$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and
Q is an oxygen atom, or an N-oxide thereof.

In the formula (1), compounds wherein
$R^1$ is an ethyl group, a cyclopropyl group or a cyclopropylmethyl group,
$R^2$, $R^4$ and $R^5$ are a hydrogen atom,
$R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a 2-pyridyl group, a 2-pyrimidinyl group, a 5-trifluoromethyl-2-pyridyl group, a 3-chloro-5-trifluoromethyl-2-pyridyl group, a fluorine atom, a chlorine atom, a bromine atom, an iodine atom or a hydrogen atom,
$R^6$ is a methyl group, an ethyl group, a propyl group, an isopropyl group, a butyl group, an isobutyl group, a hexyl group, a propargyl group, a cyclopropyl group, a cyclobutyl group, a cyclohexyl group, a cyclopropylmethyl group, a cyclobutylmethyl group, a 2,2,2-trifluoroethyl group, a benzyl group, a 6-chloropyridin-3-ylmethyl group, a 2-chlorothiazolyl-5-ylmethyl group, a methoxymethyl group, an ethoxymethyl group, a methoxycarbonyl group or an ethoxycarbonyl group,
$G^1$ is a nitrogen atom or $=CR^7-$,
$G^2$ is a nitrogen atom or $=CR^8-$,
$G^3$ is $=CR^9-$,
$G^4$ is $=CR^{10}-$,
$G^5$ is a nitrogen atom or $=CR^{11}-$ (wherein one or two of $G^1$, $G^2$ and $G^5$ represent a nitrogen atom),
$R^7$ and $R^{11}$ are a hydrogen atom,
$R^8$, $R^9$ and $R^{10}$ are the same or different and are a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, a fluorine atom, a chlorine atom, a bromine atom or a hydrogen atom, and
Q is an oxygen atom, or an N-oxide thereof.

In the formula (1), compounds wherein
$R^1$ is a C1 to C6 chain hydrocarbon group optionally having one or more atoms or groups selected from group X or a C3 to C6 cycloalkyl group optionally having one or more atoms or groups selected from group Y,
$R^2$, $R^4$ and $R^5$ are a hydrogen atom,
$R^3$ is a C1 to C6 chain hydrocarbon group optionally having one or more atoms or groups selected from group X or a hydrogen atom,
$R^6$ is a C1 to C6 chain hydrocarbon group optionally having one or more atoms or groups selected from group W or $C(O)OR^{12}$,
$G^1$ is a nitrogen atom or $=CR^7-$,
$G^2$ is a nitrogen atom or $=CR^8-$,
$G^3$ is a nitrogen atom or $=CR^9-$,
$G^4$ is a nitrogen atom or $=CR^{10}-$,
$G^5$ is a nitrogen atom or $=CR^{11}-$,
$R^7$, $R^8$, $R^{10}$ and $R^{11}$ are a hydrogen atom,
$R^9$ is a C1 to C6 chain hydrocarbon group optionally having one or more atoms or groups selected from group X or $-S(O)_mR^{12}$,
$R^{12}$ is the same or different and is a C1 to C6 alkyl group optionally having one or more halogen atoms, and
Q is an oxygen atom, or an N-oxide thereof.

In the formula (1), compounds wherein
$R^1$ is a C1 to C3 alkyl group optionally having a cyclopropyl group or a cyclopropyl group,
$R^2$, $R^4$ and $R^5$ are a hydrogen atom,
$R^3$ is a C1 to C3 chain hydrocarbon group optionally having one or more halogen atoms or a hydrogen atom,
$R^6$ is a C1 to C3 alkyl group, a C2 to C6 alkynyl group or a methoxycarbonyl group, which optionally has a cyclopropyl group or a methoxy group.
$G^1$ is a nitrogen atom or $=CR^7-$,
$G^2$ is a nitrogen atom or $=CR^8-$,
$G^3$ is a nitrogen atom or $=CR^9-$,
$G^4$ is a nitrogen atom or $=CR^{10}-$,
$G^5$ is a nitrogen atom or $=CR^{11}-$,
$R^7$, $R^8$, $R^{10}$ and $R^{11}$ are a hydrogen atom,
$R^9$ is a C1 to C3 alkyl group optionally having one or more halogen atoms or $-S(O)_mR^{12}$,
$R^{12}$ is the same or different and is a C1 to C3 alkyl group optionally having one or more halogen atoms, and
Q is an oxygen atom, or an N-oxide thereof.

In the formula (1), compounds wherein
$R^1$ is a C1 to C6 chain hydrocarbon group optionally having one or more atoms or groups selected from group X,
$R^2$, $R^4$ and $R^5$ are a hydrogen atom,
$R^3$ is a C1 to C6 chain hydrocarbon group optionally having one or more atoms or groups selected from group X or a hydrogen atom,
$R^6$ is a C1 to C6 chain hydrocarbon group optionally having one or more atoms or groups selected from group W,
$G^1$ is a nitrogen atom,
$G^2$, $G^4$ and $G^5$ are $=CH-$,
$G^3$ is $=CR^9-$,
$R^9$ is a C1 to C6 chain hydrocarbon group optionally having one or more atoms or groups selected from group X or $-S(O)_mR^{12}$,
$R^{12}$ is a C1 to C6 alkyl group optionally having one or more halogen atoms, and
Q is an oxygen atom, or an N-oxide thereof.

In the formula (1), compounds wherein
$R^1$ is a C1 to C6 alkyl group optionally having one or more halogen atoms,
$R^2$, $R^4$ and $R^5$ are a hydrogen atom,
$R^3$ is a C1 to C6 alkyl group optionally having one or more halogen atoms or a hydrogen atom, $R^6$ is a C1 to C6 alkyl group optionally having one or more halogen atoms or cyclopropyl groups, $G^1$ is a nitrogen atom, $G^2$, $G^4$ and $G^5$ are =CH—, $G^3$ is =CR$^9$—, $R^9$ is a C1 to C6 alkyl group optionally having one or more halogen atoms or —S(O)$_m$R$^{12}$, $R^{12}$ is a C1 to C6 alkyl group optionally having one or more halogen atoms, and Q is an oxygen atom, or an N-oxide thereof.

In the formula (1), compounds wherein $R^1$ is a C1 to C3 alkyl group, $R^2$, $R^4$ and $R^5$ are a hydrogen atom, $R^3$ is a C1 to C3 alkyl group optionally having one or more halogen atoms or a hydrogen atom, $R^6$ is a C1 to C3 alkyl group optionally having a cyclopropyl group, $G^1$ is a nitrogen atom, $G^2$, $G^4$ and $G^5$ are =CH—, $G^3$ is =CR$^9$—, $R^9$ is a C1 to C3 alkyl group optionally having one or more halogen atoms or —S(O)$_m$R$^{12}$, $R^{12}$ is a C1 to C3 perfluoroalkyl group, and Q is an oxygen atom, or an N-oxide thereof.

In the formula (1), compounds wherein $R^1$ is an ethyl group, $R^2$, $R^4$ and $R^5$ are a hydrogen atom, $R^3$ is a C1 to C3 perfluoroalkyl group or a hydrogen atom, $R^6$ is a C1 to C3 alkyl group or a cyclopropylmethyl group, $G^1$ is a nitrogen atom, $G^2$ is =CH—, $G^3$ is =CR$^9$—, $G^4$ is =CH—, $G^5$ is =CH—, $R^9$ is a C1 to C3 alkyl group optionally having one or more halogen atoms, a C1 to C3 alkylsulfanyl group optionally having one or more halogen atoms, a halogen atom or a hydrogen atom, and Q is an oxygen atom, or an N-oxide thereof.

Next, the method for producing the compound of the present invention and the present intermediate compound will be described.

The compound of the present invention and the intermediate compound can be produced, for example, according to the following (Production Method 1) to (Production Method 13).

(Production Method 1)

The compound of the present invention (1-n1) or the compound of the present invention (1-n2) in which n is 1 or 2 in the formula (1) can be produced by oxidizing the compound of the present invention (1-n0) in which n is 0:

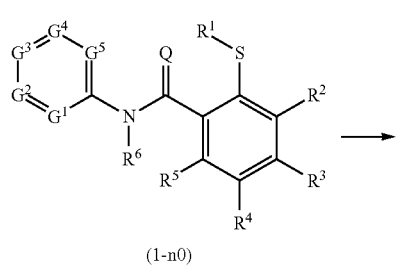

(1-n0)

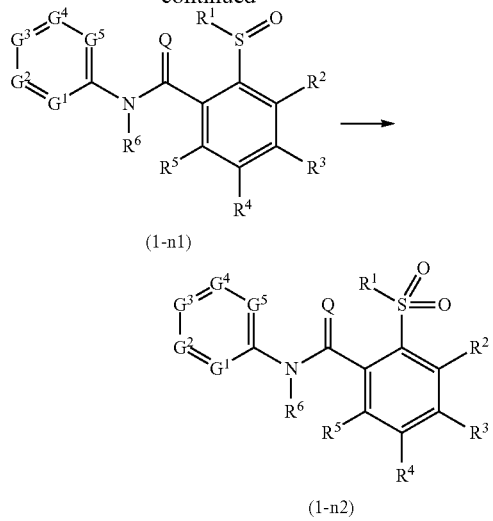

(1-n1)

(1-n2)

wherein symbols represent the same meaning as described above.

The compound of the present invention (1-n1) in which n is 1 in the formula (1) can be produced by subjecting the compound of the present invention (1-n0) in which n is 0 to an oxidation reaction.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include sodium periodate and m-chloroperbenzoic acid.

In the reaction, the oxidizing agent is usually used in a ratio of 1 to 3 mol, based on 1 mol of the compound of the present invention (1-n0). Preferably, the oxidizing agent is used in a ratio of 1 to 1.2 mol, based on 1 mol of the compound of the present invention (1-n0).

The reaction temperature is usually within the range of −20 to 80° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n1) can be isolated. The isolated compound of the present invention (1-n1) also can be further purified by chromatography, recrystallization, or the like. Alternatively, the compound of the present invention (1-n1) can be used to the next reaction as it is without isolation.

The compound of the present invention (1-n2) in which n is 2 in the formula (1) can be produced by allowing the compound of the present invention (1-n1) in which n is 1 to react with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 1 to 4 mol, based on 1 mol of the compound of the present invention (1-n1). Preferably, the oxidizing agent is used in a ratio of 1 to 1.2 mol, based on 1 mol of the compound of the present invention (1-n1).

The reaction temperature is usually within the range of −20 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n2) can be isolated. The compound of the present invention (1-n2) also can be further purified by chromatography, recrystallization, or the like.

The compound of the present invention (1-n2) in which n is 2 in the formula (1) can be produced by a one step reaction (one pot) by allowing the compound of the present invention (1-n0) in which n is 0 to react with an oxidizing agent.

The reaction is usually carried out in the presence of a solvent.

Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

The reaction can be also carried out, in the presence of a catalyst, as necessary.

Examples of the catalyst used in the reaction include sodium tungstate.

In the reaction, the oxidizing agent is usually used in a ratio of 2 to 5 mol, and the catalyst is usually used in a ratio of 0.01 to 0.5 mol, based on 1 mol of the compound of the present invention (1-n0). Preferably, the oxidizing agent is used in a ratio of 2 to 2.2 mol, based on 1 mol of the compound of the present invention (1-n0).

The reaction temperature is usually within the range of 0 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n2) can be isolated. The isolated compound of the present invention (1-n2) also can be further purified by chromatography, recrystallization, or the like.

(Production Method 2)

The compound of the present invention (P1) in which Q is an oxygen atom in the formula (1) can be produced by allowing the intermediate compound (M1) to react with the intermediate compound (M2):

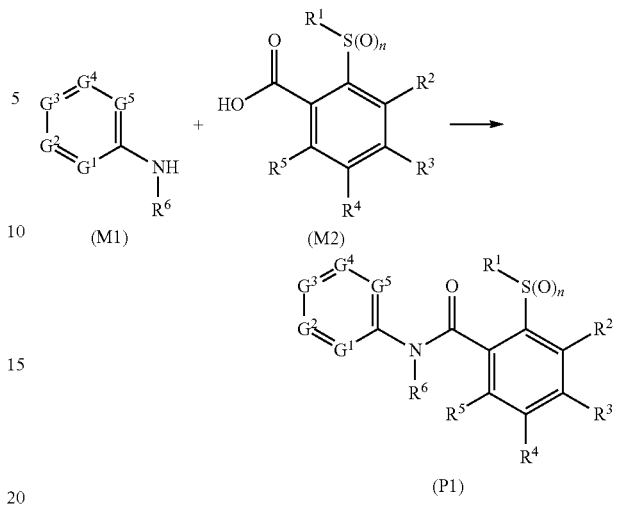

wherein symbols represent the same meaning as described above.

The compound of the present invention (P1) can be produced by allowing the intermediate compound (M1) to react with the intermediate compound (M2), in the presence of a condensing agent.

The reaction is usually carried out in the presence of a solvent. Examples of the solvent include ethers such as 1,4-dioxane, diethyl ether, tetrahydrofuran (hereinafter, referred to as THF) and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as N,N-dimethylformamide (hereinafter, referred to as DMF), N-methyl pyrrolidone (hereinafter, referred to as NMP), 1,3-dimethyl-2-imidazolidinone and dimethyl sulfoxide (hereinafter, referred to as DMSO), nitrogen-containing aromatic compounds such as pyridine and quinoline, and mixtures thereof.

Examples of the condensing agent include carbodiimides such as 1-ethyl-3-(3-dimethylaminopropyl)carbodiimide hydrochloride (hereinafter, referred to as EDCI hydrochloride) and 1,3-dicyclohexylcarbodiimide.

The reaction can be also carried out by adding a catalyst, as necessary.

Examples of the catalyst used in the reaction include 1-hydroxybenzotriazole (hereinafter, referred to as HOBt).

In the reaction, the intermediate compound (M2) is usually used in a ratio of 0.8 to 1.2 mol, the condensing agent is usually used in a ratio of 1 to 2 mol, and the catalyst is usually used in a ratio of 0.01 to 1 mol, based on 1 mol of the intermediate compound (M1).

The reaction temperature is usually within the range of 0 to 200° C. The reaction time is usually within the range of 0.1 to 24 hours.

After completion of the reaction, the compound of the present invention (P1) can be isolated by adding the reaction mixture to water, then extracting the mixture with an organic solvent, and concentrating the organic layer; collecting a solid generated by adding the reaction mixture to water by filtration; or collecting a solid generated in the reaction mixture by filtration. The isolated compound of the present invention (P1) also can be further purified by recrystallization, chromatography, or the like.

(Production Method 3)

The compound of the present invention (P1) in which Q is an oxygen atom in the formula (1) can be produced by allowing the intermediate compound (M1) to react with the intermediate

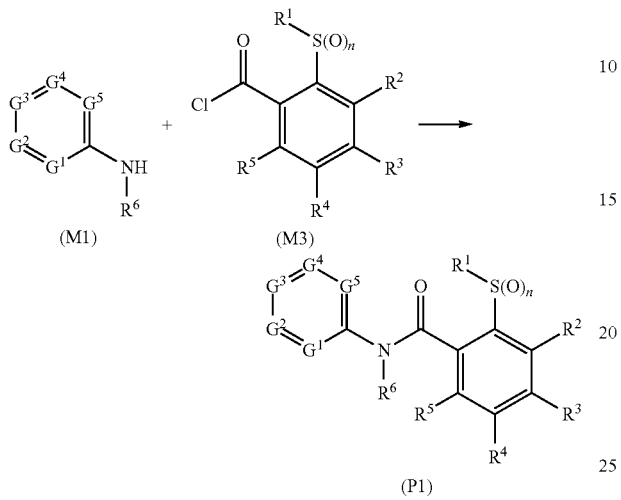

wherein symbols represent the same meaning as described above.

The compound of the present invention (P1) can be produced by allowing the intermediate compound (M1) to react with the intermediate compound (M3).

The reaction is usually carried out in the presence of a solvent.

Examples of the solvent used in the reaction include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out by adding a base, as necessary.

The base used in the reaction includes alkali metal carbonates such as sodium carbonate and potassium carbonate, tertiary amines such as triethylamine and N,N-diisopropylethylamine, nitrogen-containing aromatic compounds such as pyridine, 4-dimethylaminopyridine, and the like.

In the reaction, the intermediate compound (M3) is usually used in a ratio of 0.8 to 1.2 mol, and the base is usually used in a ratio of 1 to 2 mol, based on 1 mol of the intermediate compound (M1).

The reaction temperature is usually within the range of −20 to 200° C. The reaction time is usually within the range of 0.1 to 24 hours.

After completion of the reaction, water is added to the reaction mixture, then the reaction mixture is extracted with an organic solvent, and the organic layer is subjected to post-treatment operations such as drying and concentration, whereby the compound of the present invention (P1) can be isolated. The isolated compound of the present invention (P1) also can be further purified by chromatography, recrystallization, or the like.

(Production Method 4)

The compound of the present invention (P1) in which Q is an oxygen atom in the formula (1) can be produced by allowing the intermediate compound (M4) to react with the intermediate compound (M5):

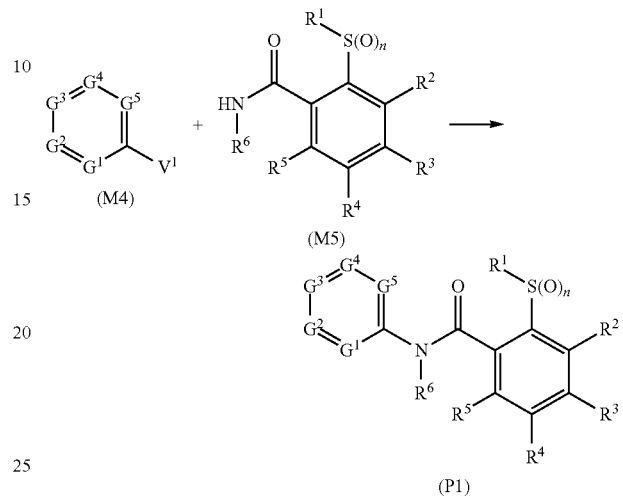

wherein $V^1$ represents a halogen atom, and other symbols represent the same meaning as described above.

When $V^1$ is a fluorine atom, the compound of the present invention (P1) in which Q is an oxygen atom in the formula (1) can be produced by allowing the intermediate compound (M4) to react with the intermediate compound (M5), in the presence of a base.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, water, and mixtures thereof.

Examples of the base include alkali metal carbonates such as sodium carbonate, potassium carbonate and cesium carbonate, and alkali metal hydrides such as sodium hydride.

In the reaction, the intermediate compound (M5) is usually used in a ratio of 0.8 to 1.2 mol, and the base is usually used in a ratio of 1 to 2 mol, based on 1 mol of the intermediate compound (M4).

The reaction temperature is usually within the range of 0 to 200° C. The reaction time is usually within the range of 0.5 to 24 hours.

After completion of the reaction, the reaction mixture is extracted with an organic solvent, and the organic layer is subjected to post-treatment operations such as drying and concentration, whereby the compound of the present invention (P1) can be isolated. The isolated compound of the present invention (P1) also can be further purified by chromatography, recrystallization, or the like.

When $V^1$ is a chlorine atom, a bromine atom or an iodine atom, the compound of the present invention (P1) in which Q is an oxygen atom in the formula (1) can be produced by reacting the intermediate compound (M4) with the intermediate compound (M5), in the presence of a base, a copper catalyst or a palladium catalyst.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, water, and mixtures thereof.

Examples of the base used in the reaction include alkali metal carbonates such as sodium carbonate and potassium carbonate, phosphates such as trisodium phosphate and tripotassium phosphate, alkali metal hydrides such as sodium hydride, tertiary amines such as triethylamine and N,N-diisopropylethylamine, and cyclic amines such as 1,4-diazabicyclo[2,2,2]octane (hereinafter, referred to as DABCO) and diazabicycloundecene (hereinafter, referred to as DBU).

Examples of the copper catalyst used in the reaction include copper(I) iodide, copper(I) bromide, copper(I) chloride, copper(I) oxide, and the like.

Examples of the palladium catalyst used in the reaction include palladium(II) acetate, tris(dibenzylideneacetone)dipalladium(0), and the like.

The reaction can be also carried out by adding a ligand as necessary.

Examples of the ligand used in the reaction include acetylacetone, salen, phenanthroline, triphenylphosphine, 4,5'-bis(diphenylphosphino)-9,9'-dimethylxanthene, and the like.

In the reaction, the intermediate compound (M5) is usually used in a ratio of 0.8 to 1.2 mol, the base is usually used in a ratio of 1 to 2 mol, the copper catalyst is usually used in a ratio of 0.01 to 0.5 mol, the palladium catalyst is usually used in a ratio of 0.01 to 0.2 mol, and the ligand is usually used in a ratio of 0.01 to 0.5 mol, based on 1 mol of the intermediate compound (M4).

The reaction temperature is usually within the range of 0 to 200° C. The reaction time is usually within the range of 0.5 to 24 hours.

After completion of the reaction, the reaction mixture is extracted with an organic solvent, and the organic layer is subjected to post-treatment operations such as drying and concentration, whereby the compound of the present invention (P1) can be isolated. The isolated compound of the present invention (P1) also can be further purified by chromatography, recrystallization, or the like.

(Production Method 5)

The compound of the present invention (1) can be produced by allowing the intermediate compound (M6) to react with the intermediate compound (M7), in the presence of a base:

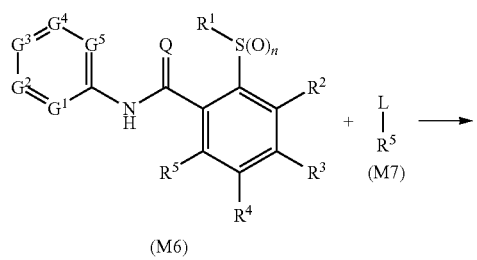
(M6)

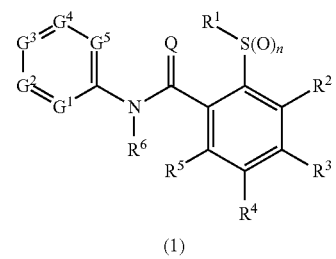
(1)

wherein L represents a leaving group such as a chlorine atom, a bromine atom, an iodine atom, a trifluoromethanesulfonyloxy group or a methanesulfonyloxy group, and other symbols represent the same meaning as described above.

The reaction is usually carried out in the presence of a solvent.

Examples of the solvent used in the reaction include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, and mixtures thereof.

Examples of the base used in the reaction include hydrides of alkali metals or alkaline earth metals such as sodium hydride, potassium hydride and calcium hydride, inorganic bases such as sodium carbonate and potassium carbonate, organic bases such as triethylamine, and the like.

In the reaction, the intermediate compound (M7) is usually used in a ratio of 1 to 5 mol, and the base is usually used in a ratio of 1 to 2 mol, based on 1 mol of the intermediate compound (M6).

The reaction temperature is usually within the range of 0 to 100° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (1) can be isolated. The isolated compound of the present invention (1) also can be further purified by chromatography, recrystallization, or the like.

(Production Method 6)

The compound of the present invention (1) can be produced by allowing the intermediate compound (M6) to react with the intermediate compound (M8), in the presence of a condensing agent:

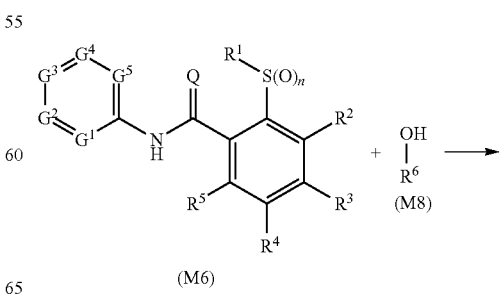
(M6)

-continued

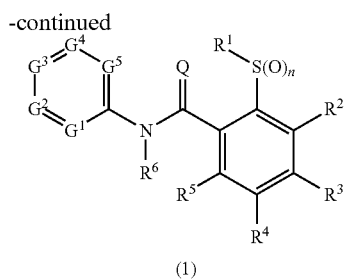

(1)

wherein symbols represent the same meaning as described above.

The reaction is usually carried out in the presence of a solvent.

Examples of the solvent used in the reaction include ethers such as THF, ethylene glycol dimethyl ether, tert-butyl methyl ether and 1,4-dioxane, aromatic hydrocarbons such as toluene and xylene, nitriles such as acetonitrile, aliphatic halogenated hydrocarbons such as dichloromethane and chloroform, aprotic polar solvents such as DMF, NMP and DMSO, and mixtures thereof.

Examples of the condensing agent include a mixture of diethyl azodicarboxylate, 1,1'-(diazocarbonyl)dipiperidine and triphenylphosphine.

In the reaction, the intermediate compound (M8) is usually used in a ratio of 1 to 5 mol, and the condensing agent is usually used in a ratio of 1 to 2 mol, based on 1 mol of the intermediate compound (M6).

The reaction temperature is usually within the range of 0 to 150° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (1) can be isolated. The isolated compound of the present invention (1) also can be further purified by chromatography, recrystallization, or the like.

(Production Method 7)

The compound of the present invention (P2) in which Q is an oxygen atom and n is 0 in the formula (1) can be produced by allowing the intermediate compound (M11) to react with the intermediate compound (M12), in the presence of a base:

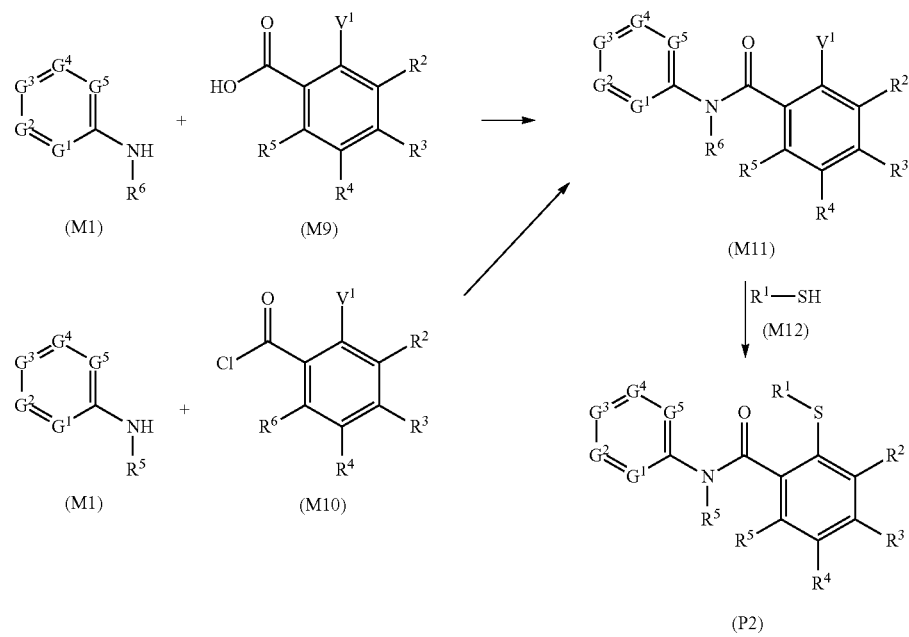

wherein symbols represent the same meaning as described above.

The intermediate compound (M11) can be produced, using the intermediate compound (M9) in place of the intermediate compound (M2), in accordance with the method of Production Method 2.

The intermediate compound (M11) can be produced, using the intermediate compound (M10) in place of the intermediate compound (M2), in accordance with the method of the step of Production Method 2.

The compound of the present invention (P2) in which Q is an oxygen atom and n is 0 in the formula (1) can be produced by allowing the intermediate compound (M11) to react with the intermediate compound (M12), in the presence of a base.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, water, and mixtures thereof.

Examples of the base include alkali metal carbonates such as sodium carbonate and potassium carbonate, and alkali metal hydrides such as sodium hydride.

In the reaction, the compound (M12) is usually used in a ratio of 0.8 to 1.2 mol, and the base is usually used in a ratio of 1 to 2 mol, based on 1 mol of the intermediate compound (M11).

The reaction temperature is usually within the range of 0 to 150° C. The reaction time is usually within the range of 0.5 to 24 hours.

After completion of the reaction, the reaction mixture is extracted with an organic solvent, and the organic layer is subjected to post-treatment operations such as drying and concentration, whereby the compound of the present invention (P2) can be isolated. The isolated compound of the present invention (P2) also can be further purified by chromatography, recrystallization, or the like.

In the reaction, $V^1$ is preferably a fluorine atom or a chlorine atom.

The compound of the present invention (P2) in which Q is an oxygen atom and n is 0 in the formula (1) can be produced by allowing the intermediate compound (M13) to react with the intermediate compound (M14), in the presence of a base:

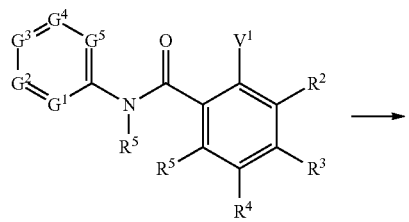

(M11)

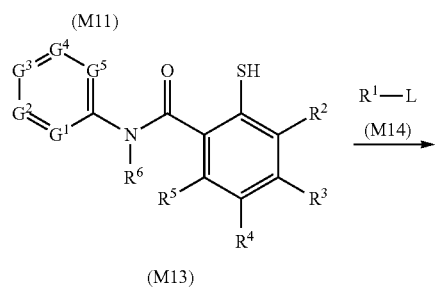

(M13)

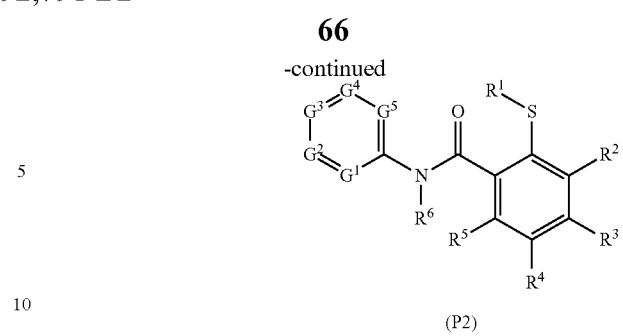

(P2)

wherein symbols represent the same meaning as described above.

The intermediate compound (M13) can be produced, using sodium sulfide, sodium hydrogen sulfide or hydrogen sulfide in place of the intermediate compound (M12), in accordance with the method of Production Method 7.

The compound of the present invention (P2) in which Q is an oxygen atom and n is 0 in the formula (1) can be produced by allowing the intermediate compound (M13) to react with the intermediate compound (M14), in the presence of a base.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, and mixtures thereof.

Examples of the base include hydrides of alkali metals or alkaline earth metals such as sodium hydride, potassium hydride and calcium hydride, inorganic bases such as sodium carbonate and potassium carbonate, organic bases such as triethylamine, and the like.

In the reaction, the intermediate compound (M14) is usually used in a ratio of 1 to 5 mol, and the base is usually used in a ratio of 1 to 2 mol, based on 1 mol of the intermediate compound (M13).

The reaction temperature is usually within the range of 0 to 100° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (P2) can be isolated. The isolated compound of the present invention (P2) also can be further purified by chromatography, recrystallization, or the like.

(Production Method 9)

The compound of the present invention (P3) in which Q is a sulfur atom in the formula (1) can be produced by allowing the compound of the present invention (P1) in which Q is an oxygen atom in the formula (1) to react with a sulfurizing agent:

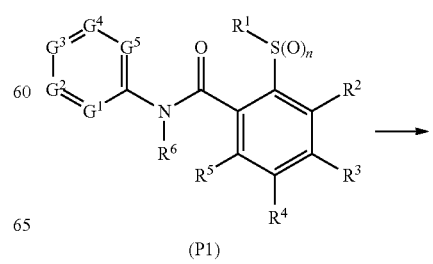

(P1)

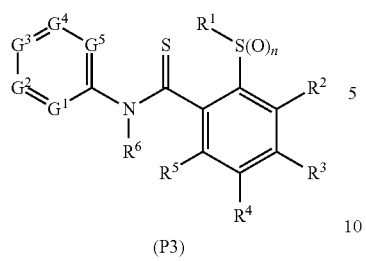

(P3)

wherein symbols represent the same meaning as described above.

The reaction is usually carried out in the presence or absence of a solvent.

Examples of the solvent include ethers such as 1,4-dioxane, diethyl ether, tetrahydrofuran, tert-butyl methyl ether and diglyme, halogenated hydrocarbons such as dichloromethane, chloroform, carbon tetrachloride, 1,2-dichloroethane and chlorobenzene, aromatic hydrocarbons such as toluene, benzene and xylene, nitriles such as acetonitrile, nitrogen-containing aromatic compounds such as pyridine, picoline, lutidine and quinoline, and mixtures thereof.

The sulfurizing agent includes diphosphorus pentasulfide, Lawesson's reagent (2,4-bis-(4-methoxyphenyl)-1,3-dithia-2,4-diphosphetane-2,4-disulfide), and the like.

In the reaction, the sulfurizing agent is usually used in a ratio of 1 to 3 mol, based on 1 mol of the compound of the present invention (P1).

The reaction temperature is usually within the range of 0 to 200° C., and the reaction time is usually within the range of 1 to 24 hours.

After completion of the reaction, the compound of the present invention (P3) can be isolated by adding the reaction mixture to water, then extracting the mixture with an organic solvent, and concentrating the organic layer; collecting a solid generated by adding the reaction mixture to water by filtration; or collecting a solid generated in the reaction mixture by filtration. The isolated compound of the present invention (P3) also can be further purified by recrystallization, chromatography, or the like.

(Production Method 10)

The intermediate compound (M2) can be produced by hydrolyzing the intermediate compound (M15). Also, the intermediate compound (M3) can be produced by allowing the intermediate compound (M2) to react with a chlorinating agent:

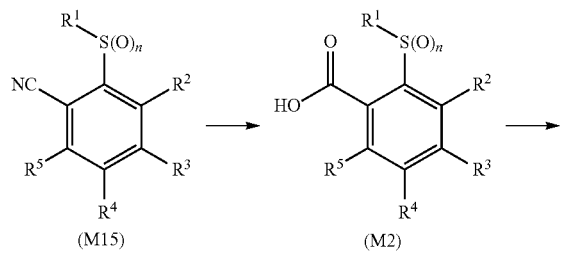

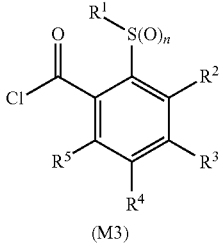

(M3)

wherein symbols represent the same meaning as described above.

The intermediate compound (M2) can be produced by hydrolyzing the intermediate compound (M15).

When hydrolyzed by an acid, the reaction is usually carried out using an aqueous solution of an acid as a solvent.

Examples of the acid include mineral acids such as hydrochloric acid, nitric acid, phosphoric acid and sulfuric acid, and carboxylic acids such as acetic acid and trifluoroacetic acid.

The reaction temperature is usually within the range of 0 to 150° C. The reaction time is usually within the range of 0.1 to 24 hours.

After completion of the reaction, the reaction mixture is extracted with an organic solvent, and the organic layer is subjected to post-treatment operations such as drying and concentration, whereby the intermediate compound (M2) can be isolated. The isolated intermediate compound (M2) also can be further purified by chromatography, recrystallization, or the like.

When hydrolyzed by a base, the reaction is usually carried out in the presence of a solvent.

Examples of the solvent include ethers such as THF, ethylene glycol dimethyl ether, tert-butyl methyl ether and 1,4-dioxane, alcohols such as methanol and ethanol, water, and mixtures thereof.

Examples of the base include alkali metal hydroxides such as sodium hydroxide and potassium hydroxide.

In the reaction, the base is usually used in a ratio of 1 to 10 mol, based on 1 mol of the intermediate compound (M15).

The reaction temperature is usually within the range of 0 to 120° C. The reaction time is usually within the range of 0.1 to 24 hours.

After completion of the reaction, the reaction solution is acidified, then the reaction mixture is extracted with an organic solvent, and the organic layer is subjected to post-treatment operations such as drying and concentration, whereby the intermediate compound (M2) can be isolated. The isolated intermediate compound (M2) also can be further purified by chromatography, recrystallization, or the like.

The intermediate compound (M3) can be produced by allowing the intermediate compound (M2) to react with a chlorinating agent.

The reaction is usually carried out in the presence of a solvent.

Examples of the solvent include ethers such as THF, ethylene glycol dimethyl ether, tert-butyl methyl ether and 1,4-dioxane, aromatic hydrocarbons such as toluene and xylene, aliphatic halogenated hydrocarbons such as dichloromethane and chloroform, and mixtures thereof.

The chlorinating agent includes thionyl chloride, oxalyl dichloride, phosphorus oxychloride, and the like.

The reaction can be also carried out by adding DMF as necessary.

In the reaction, the chlorinating agent is usually used in a ratio of 1 to 5 mol, and DMF is usually used in a ratio of 0.001 to 0.1 mol, based on 1 mol of the intermediate compound (M2).

The reaction temperature is usually within the range of 0 to 100° C. The reaction time is usually within the range of 0.1 to 24 hours.

After completion of the reaction, the intermediate compound (M3) can be isolated by distilling the solvent. Alternatively, the intermediate compound (M3) can be used to the next reaction as it is without isolation.

(Production Method 11)

The intermediate compound (M2) in which n is 0 can be produced by allowing the intermediate compound (M16) to react with the intermediate compound (M12), in the presence of a base. In addition, the intermediate compound (M2) in which n is 1 or n is 2 can be produced by oxidizing the intermediate compound (M2) in which n is 0:

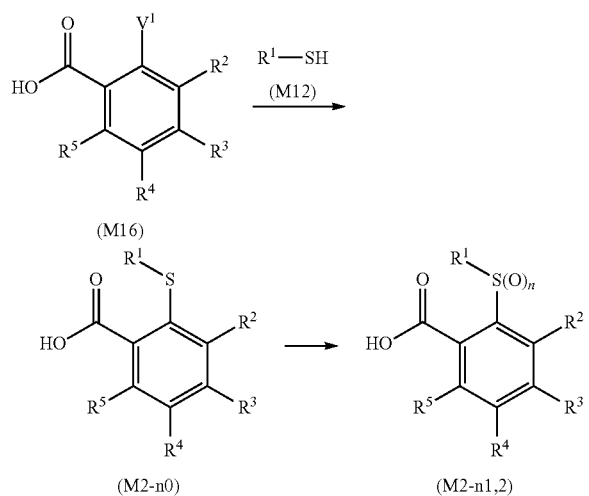

wherein symbols represent the same meaning as described above.

The intermediate compound (M2-n0) in which n is 0 can be produced, using the intermediate compound (M16) in place of the intermediate compound (M11), in accordance with the method of Production Method 7.

In the reaction, $V^1$ is preferably a fluorine atom or a chlorine atom.

The intermediate compound (M2-n1) or intermediate compound (M2-n2) in which n is 1 or 2 can be produced, using the intermediate compound (M2-n0) in which n is 0 in place of the compound of the present invention (1-n0) in which n is 0, in accordance with the method of Production Method 1.

(Production Method 12)

The intermediate compound (M6-QO) in which Q is an oxygen atom in the intermediate compound (M6) can be produced, using the intermediate compound (M17) in place of the intermediate compound (M1), in accordance with the method of Production Method 2. In addition, the intermediate compound (M6-QO) can be produced, using the intermediate compound (M17) in place of the intermediate compound (M1), in accordance with the method of Production Method 3.

The intermediate compound (M6-QS) in which Q is a sulfur atom in the intermediate compound (M6) can be produced, using the intermediate compound (M6-QO) in which Q is an oxygen atom in place of the compound of the present invention (P1), in accordance with the method of Production Method 9:

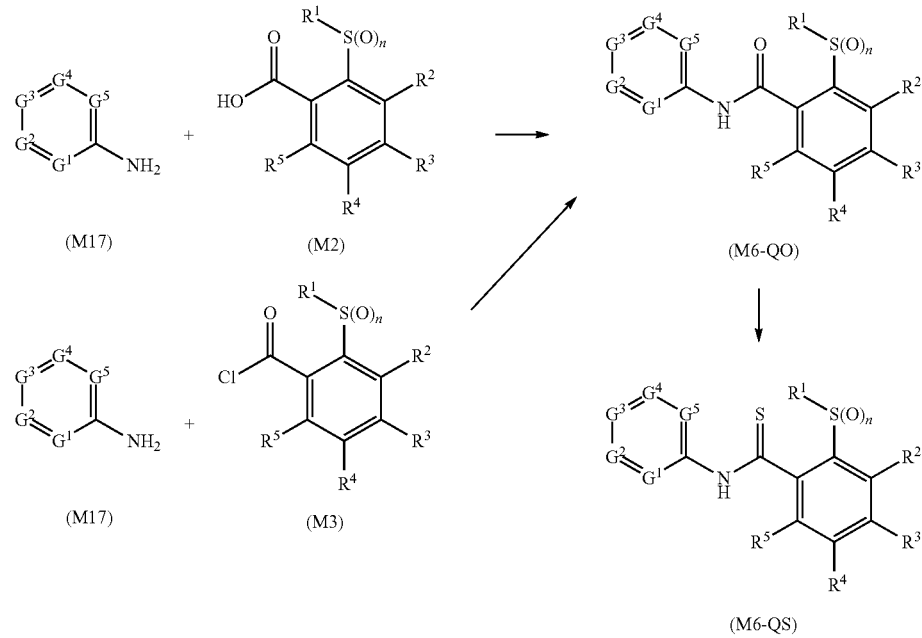

wherein symbols represent the same meaning as described above.

(Production Method 13)

Among the compounds of the present invention and the above-described intermediate compounds, a compound having a nitrogen-containing heterocyclic group having a lone pair of electrons on the nitrogen atom is reacted with an oxidizing agent, whereby an N-oxide in which the nitrogen atom is oxidized can be manufactured in some cases.

Examples of the nitrogen-containing heterocyclic group include a pyridine ring.

The reaction can be carried out by a known method, and is carried out using an oxidizing agent such as m-chloroperbenzoic acid or hydrogen peroxide, in a solvent, for example, a halogenated hydrocarbon such as dichloromethane, chloroform or chlorobenzene, an alcohol such as methanol or ethanol, acetic acid, water, and mixtures thereof.

Examples of the intermediate compound (M6) include following compounds.

A compound represented by formula (2):

$$\text{(2)}$$

[Chemical structure showing compound with groups $G^{1a}$, $G^{2a}$, $G^{3a}$, $G^{4a}$, $G^{5a}$, $Q^a$, $R^{1a}$, $R^{2a}$, $R^{3a}$, $R^{4a}$, $R^{5a}$, $S(O)_n$, and NH]

wherein $R^{1a}$ represents a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkyl)C1 to C3 alkyl group optionally having one or more halogen atoms, $R^{2a}$, $R^{4a}$ and $R^{5a}$ are the same or different and represent a halogen atom or a hydrogen atom, $R^{3a}$ represents a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $G^{1a}$ represents a nitrogen atom or $=CR^{7a}-$,
$G^{2a}$ represents a nitrogen atom or $=CR^{8a}-$,
$G^{3a}$ represents a nitrogen atom or $=CR^{9a}-$,
$G^{4a}$ represents a nitrogen atom or $=CR^{10a}-$,
$G^{5a}$ represents a nitrogen atom or $=CR^{11a}-$ (wherein, while at least one of $G^{1a}$, $G^{2a}$, $G^{3a}$, $G^{4a}$ and $G^{5a}$ represents a nitrogen atom, not all of $G^{2a}$, $G^{3a}$ and $G^{4a}$ represent a nitrogen atom), $R^{7a}$ and $R^{11a}$ are the same or different and represent a fluorine atom or a hydrogen atom, and $R^{8a}$, $R^{9a}$ and $R^{10a}$ are the same or different and represent a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8a}$, $R^{9a}$ and $R^{10a}$ do not represent a hydrogen atom at the same time, and at least one of $R^{8a}$, $R^{9a}$ and $R^{10a}$ represents a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group or a C1 to C6 haloalkylsulfonyl group), $Q^a$ represents an oxygen atom or a sulfur atom, and
n represents 0, 1 or 2,
or an N-oxide thereof.

In the formula (2), compounds wherein $R^{1a}$ is a C3 to C6 cycloalkyl group optionally having one or more atoms or groups selected from the group consisting of halogen atoms and C1 to C3 alkyl groups, a C2 to C6 alkyl group optionally having one or more halogen atoms or a (C3 to C6 cycloalkyl)C1 to C3 alkyl group optionally having one or more halogen atoms, $R^{2a}$, $R^{4a}$ and $R^{5a}$ are the same or different and are a halogen atom or a hydrogen atom, $R^{3a}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or substituents selected from the group consisting of C1 to C3 alkyl groups optionally having one or more halogen atoms and halogen atoms), a halogen atom or a hydrogen atom, $G^{1a}$ is a nitrogen atom or $=CR^{7a}-$,
$G^{2a}$ is a nitrogen atom or $=CR^{8a}-$,
$G^{3a}$ is a nitrogen atom or $=CR^{9a}-$,
$G^{4a}$ is a nitrogen atom or $=CR^{10a}-$,
$G^{5a}$ is a nitrogen atom or $=CR^{11a}-$ (wherein, while at least one of $G^{1a}$, $G^{2a}$, $G^{3a}$, $G^{4a}$ and $G^{5a}$ represents a nitrogen atom, not all of $G^{2a}$, $G^{3a}$ and $G^{4a}$ represent a nitrogen atom), $R^{7a}$ and $R^{11a}$ are the same or different and are a fluorine atom or a hydrogen atom, $R^{8a}$, $R^{9a}$ and $R^{10a}$ are the same or different and are a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group, a C1 to C6 haloalkylsulfonyl group, a halogen atom or a hydrogen atom (wherein $R^{8a}$, $R^{9a}$ and $R^{10a}$ do not represent a hydrogen atom at the same time, and at least one of $R^{8a}$, $R^{9a}$ and $R^{10a}$ represents a C1 to C6 haloalkyl group, a C2 to C6 haloalkenyl group, a C1 to C6 perfluoroalkoxy group, a C1 to C6 haloalkylsulfanyl group, a C1 to C6 haloalkylsulfinyl group or a C1 to C6 haloalkylsulfonyl group, $Q^a$ is an oxygen atom or a sulfur atom, and n is 0, 1 or 2, or an N-oxide thereof.

In the formula (2), compounds wherein $G^{1a}$ is a nitrogen atom, $G^{2a}$ is $=CR^{8a}$—, $G^{3a}$ is $=CR^{9a}$—, $G^{4a}$ is $=CR^{10a}$— and $G^{5a}$ is $=CR^{11a}$—, or an N-oxide thereof.

In the formula (2), compounds wherein $G^{1a}$ is $=CR^{7a}$—, $G^{2a}$ is a nitrogen atom, $G^{3a}$ is $=CR^{9a}$—, $G^{4a}$ is $=CR^{10a}$ and $G^{5a}$ is $=CR^{11a}$—, or an N-oxide thereof.

In the formula (2), compounds wherein $G^1$ is $=CR^{7a}$—, $G^{2a}$ is $=CR^{8a}$—, $G^{3a}$ is a nitrogen atom, $G^{4a}$ is $=CR^{10a}$— and $G^{5a}$ is $=CR^{11a}$—, or an N-oxide thereof.

In the formula (2), compounds wherein $G^{1a}$ is a nitrogen atom, $G^{2a}$ is $=CR^{8a}$—, $G^{3a}$ is a nitrogen atom, $G^{4a}$ is $=CR^{10a}$— and $G^{5a}$ is $=CR^{11a}$—, or an N-oxide thereof.

In the formula (2), compounds wherein $G^{1a}$ is a nitrogen atom, $G^{2a}$ is $CR^{8a}$—, $G^{3a}$ is $=CR^{9a}$—, $G^{4a}$ is $=CR^{10a}$— and $G^{5a}$ is a nitrogen atom, or an N-oxide thereof.

In the formula (2), compounds wherein $G^{1a}$ is $=CR^{7a}$—, $G^{2a}$ is a nitrogen atom, $G^{3a}$ is $=CR^{9a}$—, $G^{4a}$ is a nitrogen atom and $G^{5a}$ is $=CR^{11a}$—, or an N-oxide thereof.

In the formula (2), compounds wherein $G^{1a}$ is a nitrogen atom, $G^{2a}$ is a nitrogen atom, $G^{3a}$ is $=CR^{9a}$—, $G^{4a}$ is $=CR^{10a}$— and $G^{5a}$ is $=CR^{11a}$—, or an N-oxide thereof.

In the formula (2), compounds wherein $G^{1a}$ is $=CR^{7a}$—, $G^{2a}$ is a nitrogen atom, $G^{3a}$ is a nitrogen atom, $G^{4a}$ is $=CR^{10a}$— and $G^{5a}$ is $=CR^{11a}$—, or an N-oxide thereof.

In the formula (2), compounds wherein $G^{1a}$ is a nitrogen atom, $G^{2a}$ is $=CR^{8a}$—, $G^{3a}$ is $=CR^{9a}$—, $G^{4a}$ is a nitrogen atom and $G^{5a}$ is $=CR^{11a}$—, or an N-oxide thereof.

In the formula (2), compounds wherein one or two of $G^{1a}$, $G^{2a}$, $G^{3a}$, $G^{4a}$ and $G^{5a}$ are a nitrogen atom, or an N-oxide thereof.

In the formula (2), compounds wherein one or two of $G^{1a}$, $G^{2a}$, $G^{4a}$ and $G^{5a}$ are a nitrogen atom and $G^{3a}$ is $=CR^{9a}$—, or an N-oxide thereof.

In the formula (2), compounds wherein $G^{1a}$ is a nitrogen atom or $=CR^{7a}$—, $G^{2a}$ is a nitrogen atom or $=CR^{8a}$—, $G^{3a}$ is $=CR^{9a}$—, $G^{4a}$ is $=CR^{10a}$—, and $G^{5a}$ is a nitrogen atom or $=CR^{11a}$— (wherein one or two of $G^{1a}$, $G^{2a}$ and $G^{5a}$ represent a nitrogen atom), or an N-oxide thereof.

In the formula (2), compounds wherein $R^{1a}$ is a C2 to C6 alkyl group, a cyclopropyl group or a cyclopropylmethyl group, $R^{2a}$, $R^{4a}$ and $R^{5a}$ are a hydrogen atom, one or two of $G^{1a}$, $G^{2a}$, $G^{3a}$, $G^{4a}$ and $G^{5a}$ are a nitrogen atom, $R^{7a}$ and $R^{11a}$ are a hydrogen atom, $R^{8a}$, $R^{9a}$ and $R^{11a}$ are the same or different and are a C1 to C2 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom, or an N-oxide thereof.

In the formula (2), compounds wherein $R^{1a}$ is a C2 to C6 alkyl group optionally having one or more halogen atoms, $R^{2a}$, $R^{4a}$ and $R^{5a}$ are the same or different and are a hydrogen atom, $R^{3a}$ is a C1 to C3 alkyl group optionally having one or more halogen atoms or a hydrogen atom, $G^{1a}$ represents a nitrogen atom or $=CR^{7a}$—, $G^{2a}$ represents a nitrogen atom or $=CR^{8a}$—, $G^{3a}$ represents $=CR^{9a}$—, $G^{4a}$ represents $=CR^{10a}$—, $G^{5a}$ represents $=CH$— (wherein one or two of $G^{1a}$ and $G^{2a}$ represent a nitrogen atom), $R^{7a}$ represents a C1 to C3 alkyl group, or a C1 to C3 alkylsulfanyl group, $R^{8a}$, $R^{9a}$ and $R^{10a}$ are the same or different and represent a C1 to C3 haloalkyl group, a C1 to C3 haloalkylsulfanyl group or a hydrogen atom, and $Q^a$ is an oxygen atom, or an N-oxide thereof.

In the formula (2), compounds wherein $R^{1a}$ is an ethyl group, a cyclopropyl group or a cyclopropylmethyl group, $R^{2a}$, $R^{4a}$ and $R^{5a}$ are a hydrogen atom, one or two of $G^{1a}$, $G^{2a}$, $G^{3a}$, $G^{4a}$ and $G^{5a}$ are a nitrogen atom, $R^{7a}$ and $R^{11a}$ are a hydrogen atom, $R^{8a}$, $R^{9a}$ and $R^{10a}$ are the same or different and are a C1 to C2 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom, or an N-oxide thereof.

In the formula (2), compounds wherein $R^{1a}$ is an ethyl group, a cyclopropyl group or a cyclopropylmethyl group, $R^{2a}$, $R^{4a}$ and $R^{5a}$ are a hydrogen atom, $R^{3a}$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a 2-pyridyl group, a 2-pyrimidinyl group, a 5-trifluoromethyl-2-pyridyl group, a 3-chloro-5-trifluoromethyl-2-pyridyl group, a fluorine atom, a chlorine atom, a bromine atom, an iodine atom or a hydrogen atom, one or two of $G^{1a}$, $G^{2a}$, $G^{3a}$, $G^{4a}$ and $G^{5a}$ are a nitrogen atom, $R^{7a}$ and $R^{11a}$ are a hydrogen atom, $R^{8a}$, $R^{9a}$ and $R^{10a}$ are the same or different and are a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group, a fluorine atom, a chlorine atom, a bromine atom or a hydrogen atom, and $Q^a$ is an oxygen atom, or an N-oxide thereof.

In the formula (2), compounds wherein $R^{1a}$ is an ethyl group, a cyclopropyl group or a cyclopropylmethyl group, $R^{2a}$, $R^{4a}$ and $R^{5a}$ are a hydrogen atom, $R^{3a}$ is a C1 to C3 perfluoroalkyl group, a halogen atom or a hydrogen atom, $G^{1a}$ is a nitrogen atom, $G^{2a}$ is $=CR^{8a}$—, $G^{3a}$ represents $=CR^{9a}$—, $G^{4a}$ represents $=CR^{10a}$—, $G^{5a}$ represents $=CH$—, $R^{8a}$ and $R^{10a}$ are the same or different and are a C1 to C3 alkyl group optionally having one or more halogen atoms, a halogen atom or a hydrogen atom, $R^{9a}$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a halogen atom or a hydrogen atom, and $Q^a$ is an oxygen atom, or an N-oxide thereof.

Next, specific examples of the compound of the present invention are shown below.

In the formula (1):

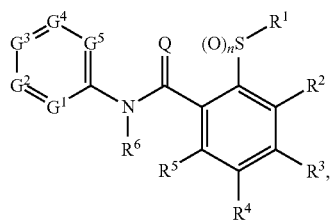
(1)

compounds of the present invention wherein n is 0, $R^2$, $R^3$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

TABLE 1

| $R^1$ | $R^6$ | $G^X$ |
|---|---|---|
| Me | Me | $CCF_3$ |
| Et | Me | $CCF_3$ |
| Pr | Me | $CCF_3$ |
| $CH_2CF_3$ | Me | $CCF_3$ |
| $CH_2C≡CH$ | Me | $CCF_3$ |
| CycPr | Me | $CCF_3$ |
| $CH_2CycPr$ | Me | $CCF_3$ |
| Me | Et | $CCF_3$ |
| Et | Et | $CCF_3$ |
| Pr | Et | $CCF_3$ |
| $CH_2CF_3$ | Et | $CCF_3$ |
| $CH_2C≡CH$ | Et | $CCF_3$ |
| CycPr | Et | $CCF_3$ |
| $CH_2CycPr$ | Et | $CCF_3$ |
| Me | CycPr | $CCF_3$ |
| Et | CycPr | $CCF_3$ |
| Pr | CycPr | $CCF_3$ |
| $CH_2CF_3$ | CycPr | $CCF_3$ |
| $CH_2C≡CH$ | CycPr | $CCF_3$ |
| CycPr | CycPr | $CCF_3$ |
| $CH_2CycPr$ | CycPr | $CCF_3$ |

TABLE 2

| $R^1$ | $R^6$ | $G^X$ |
|---|---|---|
| Me | $CH_2CycPr$ | $CCF_3$ |
| Et | $CH_2CycPr$ | $CCF_3$ |
| Pr | $CH_2CycPr$ | $CCF_3$ |
| $CH_2CF_3$ | $CH_2CycPr$ | $CCF_3$ |
| $CH_2C≡CH$ | $CH_2CycPr$ | $CCF_3$ |
| CycPr | $CH_2CycPr$ | $CCF_3$ |
| $CH_2CycPr$ | $CH_2CycPr$ | $CCF_3$ |
| Me | $CH_2C≡CH$ | $CCF_3$ |
| Et | $CH_2C≡CH$ | $CCF_3$ |
| Pr | $CH_2C≡CH$ | $CCF_3$ |
| $CH_2CF_3$ | $CH_2C≡CH$ | $CCF_3$ |
| $CH_2C≡CH$ | $CH_2C≡CH$ | $CCF_3$ |
| CycPr | $CH_2C≡CH$ | $CCF_3$ |
| $CH_2CycPr$ | $CH_2C≡CH$ | $CCF_3$ |
| Me | $CH_2OCH_3$ | $CCF_3$ |
| Et | $CH_2OCH_3$ | $CCF_3$ |
| Pr | $CH_2OCH_3$ | $CCF_3$ |
| $CH_2CF_3$ | $CH_2OCH_3$ | $CCF_3$ |

TABLE 2-continued

| $R^1$ | $R^6$ | $G^X$ |
|---|---|---|
| $CH_2C≡CH$ | $CH_2OCH_3$ | $CCF_3$ |
| CycPr | $CH_2OCH_3$ | $CCF_3$ |
| $CH_2CycPr$ | $CH_2OCH_3$ | $CCF_3$ |

TABLE 3

| $R^1$ | $R^6$ | $G^X$ |
|---|---|---|
| Me | $CO_2CH_3$ | $CCF_3$ |
| Et | $CO_2CH_3$ | $CCF_3$ |
| Pr | $CO_2CH_3$ | $CCF_3$ |
| $CH_2CF_3$ | $CO_2CH_3$ | $CCF_3$ |
| $CH_2C≡CH$ | $CO_2CH_3$ | $CCF_3$ |
| CycPr | $CO_2CH_3$ | $CCF_3$ |
| $CH_2CycPr$ | $CO_2CH_3$ | $CCF_3$ |
| Me | 6-chloro-pyridin-3-ylmethyl | $CCF_3$ |
| Et | 6-chloro-pyridin-3-ylmethyl | $CCF_3$ |
| Pr | 6-chloro-pyridin-3-ylmethyl | $CCF_3$ |
| $CH_2CF_3$ | 6-chloro-pyridin-3-ylmethyl | $CCF_3$ |
| $CH_2C≡CH$ | 6-chloro-pyridin-3-ylmethyl | $CCF_3$ |
| CycPr | 6-chloro-pyridin-3-ylmethyl | $CCF_3$ |
| $CH_2CycPr$ | 6-chloro-pyridin-3-ylmethyl | $CCF_3$ |
| Me | 2-chloro-thiazol-5-ylmethyl | $CCF_3$ |
| Et | 2-chloro-thiazol-5-ylmethyl | $CCF_3$ |
| Pr | 2-chloro-thiazol-5-ylmethyl | $CCF_3$ |
| $CH_2CF_3$ | 2-chloro-thiazol-5-ylmethyl | $CCF_3$ |
| $CH_2C≡CH$ | 2-chloro-thiazol-5-ylmethyl | $CCF_3$ |
| CycPr | 2-chloro-thiazol-5-ylmethyl | $CCF_3$ |
| $CH_2CycPr$ | 2-chloro-thiazol-5-ylmethyl | $CCF_3$ |

TABLE 4

| $R^1$ | $R^6$ | $G^X$ |
|---|---|---|
| Me | Me | $CCF_2CF_3$ |
| Et | Me | $CCF_2CF_3$ |
| Pr | Me | $CCF_2CF_3$ |
| $CH_2CF_3$ | Me | $CCF_2CF_3$ |
| $CH_2C≡CH$ | Me | $CCF_2CF_3$ |
| CycPr | Me | $CCF_2CF_3$ |
| $CH_2CycPr$ | Me | $CCF_2CF_3$ |
| Me | Et | $CCF_2CF_3$ |
| Et | Et | $CCF_2CF_3$ |
| Pr | Et | $CCF_2CF_3$ |
| $CH_2CF_3$ | Et | $CCF_2CF_3$ |
| $CH_2C≡CH$ | Et | $CCF_2CF_3$ |
| CycPr | Et | $CCF_2CF_3$ |
| $CH_2CycPr$ | Et | $CCF_2CF_3$ |
| Me | CycPr | $CCF_2CF_3$ |
| Et | CycPr | $CCF_2CF_3$ |
| Pr | CycPr | $CCF_2CF_3$ |
| $CH_2CF_3$ | CycPr | $CCF_2CF_3$ |
| $CH_2C≡CH$ | CycPr | $CCF_2CF_3$ |
| CycPr | CycPr | $CCF_2CF_3$ |
| $CH_2CycPr$ | CycPr | $CCF_2CF_3$ |

TABLE 5

| $R^1$ | $R^6$ | $G^X$ |
|---|---|---|
| Me | $CH_2CycPr$ | $CCF_2CF_3$ |
| Et | $CH_2CycPr$ | $CCF_2CF_3$ |
| Pr | $CH_2CycPr$ | $CCF_2CF_3$ |
| $CH_2CF_3$ | $CH_2CycPr$ | $CCF_2CF_3$ |
| $CH_2C≡CH$ | $CH_2CycPr$ | $CCF_2CF_3$ |
| CycPr | $CH_2CycPr$ | $CCF_2CF_3$ |
| $CH_2CycPr$ | $CH_2CycPr$ | $CCF_2CF_3$ |
| Me | $CH_2C≡CH$ | $CCF_2CF_3$ |
| Et | $CH_2C≡CH$ | $CCF_2CF_3$ |
| Pr | $CH_2C≡CH$ | $CCF_2CF_3$ |
| $CH_2CF_3$ | $CH_2C≡CH$ | $CCF_2CF_3$ |

TABLE 5-continued

| R¹ | R⁶ | G$^X$ |
|---|---|---|
| CH₂C≡CH | CH₂C≡CH | CCF₂CF₃ |
| CycPr | CH₂C≡CH | CCF₂CF₃ |
| CH₂CycPr | CH₂C≡CH | CCF₂CF₃ |
| Me | CH₂OCH₃ | CCF₂CF₃ |
| Et | CH₂OCH₃ | CCF₂CF₃ |
| Pr | CH₂OCH₃ | CCF₂CF₃ |
| CH₂CF₃ | CH₂OCH₃ | CCF₂CF₃ |
| CH₂C≡CH | CH₂OCH₃ | CCF₂CF₃ |
| CycPr | CH₂OCH₃ | CCF₂CF₃ |
| CH₂CycPr | CH₂OCH₃ | CCF₂CF₃ |

TABLE 6

| R¹ | R⁶ | G$^X$ |
|---|---|---|
| Me | CO₂CH₃ | CCF₂CF₃ |
| Et | CO₂CH₃ | CCF₂CF₃ |
| Pr | CO₂CH₃ | CCF₂CF₃ |
| CH₂CF₃ | CO₂CH₃ | CCF₂CF₃ |
| CH₂C≡CH | CO₂CH₃ | CCF₂CF₃ |
| CycPr | CO₂CH₃ | CCF₂CF₃ |
| CH₂CycPr | CO₂CH₃ | CCF₂CF₃ |
| Me | 6-chloro-pyridin-3-ylmethyl | CCF₂CF₃ |
| Et | 6-chloro-pyridin-3-ylmethyl | CCF₂CF₃ |
| Pr | 6-chloro-pyridin-3-ylmethyl | CCF₂CF₃ |
| CH₂CF₃ | 6-chloro-pyridin-3-ylmethyl | CCF₂CF₃ |
| CH₂C≡CH | 6-chloro-pyridin-3-ylmethyl | CCF₂CF₃ |
| CycPr | 6-chloro-pyridin-3-ylmethyl | CCF₂CF₃ |
| CH₂CycPr | 6-chloro-pyridin-3-ylmethyl | CCF₂CF₃ |
| Me | 2-chloro-thiazol-5-ylmethyl | CCF₂CF₃ |
| Et | 2-chloro-thiazol-5-ylmethyl | CCF₂CF₃ |
| Pr | 2-chloro-thiazol-5-ylmethyl | CCF₂CF₃ |
| CH₂CF₃ | 2-chloro-thiazol-5-ylmethyl | CCF₂CF₃ |
| CH₂C≡CH | 2-chloro-thiazol-5-ylmethyl | CCF₂CF₃ |
| CycPr | 2-chloro-thiazol-5-ylmethyl | CCF₂CF₃ |
| CH₂CycPr | 2-chloro-thiazol-5-ylmethyl | CCF₂CF₃ |

TABLE 7

| R¹ | R⁶ | G$^X$ |
|---|---|---|
| Me | Me | COCF₃ |
| Et | Me | COCF₃ |
| Pr | Me | COCF₃ |
| CH₂CF₃ | Me | COCF₃ |
| CH₂C≡CH | Me | COCF₃ |
| CycPr | Me | COCF₃ |
| CH₂CycPr | Me | COCF₃ |
| Me | Et | COCF₃ |
| Et | Et | COCF₃ |
| Pr | Et | COCF₃ |
| CH₂CF₃ | Et | COCF₃ |
| CH₂C≡CH | Et | COCF₃ |
| CycPr | Et | COCF₃ |
| CH₂CycPr | Et | COCF₃ |
| Me | CycPr | COCF₃ |
| Et | CycPr | COCF₃ |
| Pr | CycPr | COCF₃ |
| CH₂CF₃ | CycPr | COCF₃ |
| CH₂C≡CH | CycPr | COCF₃ |
| CycPr | CycPr | COCF₃ |
| CH₂CycPr | CycPr | COCF₃ |

TABLE 8

| R¹ | R⁶ | G$^X$ |
|---|---|---|
| Me | CH₂CycPr | COCF₃ |
| Et | CH₂CycPr | COCF₃ |
| Pr | CH₂CycPr | COCF₃ |
| CH₂CF₃ | CH₂CycPr | COCF₃ |

TABLE 8-continued

| R¹ | R⁶ | G$^X$ |
|---|---|---|
| CH₂C≡CH | CH₂CycPr | COCF₃ |
| CycPr | CH₂CycPr | COCF₃ |
| CH₂CycPr | CH₂CycPr | COCF₃ |
| Me | CH₂C≡CH | COCF₃ |
| Et | CH₂C≡CH | COCF₃ |
| Pr | CH₂C≡CH | COCF₃ |
| CH₂CF₃ | CH₂C≡CH | COCF₃ |
| CH₂C≡CH | CH₂C≡CH | COCF₃ |
| CycPr | CH₂C≡CH | COCF₃ |
| CH₂CycPr | CH₂C≡CH | COCF₃ |
| Me | CH₂OCH₃ | COCF₃ |
| Et | CH₂OCH₃ | COCF₃ |
| Pr | CH₂OCH₃ | COCF₃ |
| CH₂CF₃ | CH₂OCH₃ | COCF₃ |
| CH₂C≡CH | CH₂OCH₃ | COCF₃ |
| CycPr | CH₂OCH₃ | COCF₃ |
| CH₂CycPr | CH₂OCH₃ | COCF₃ |

TABLE 9

| R¹ | R⁶ | G$^X$ |
|---|---|---|
| Me | CO₂CH₃ | COCF₃ |
| Et | CO₂CH₃ | COCF₃ |
| Pr | CO₂CH₃ | COCF₃ |
| CH₂CF₃ | CO₂CH₃ | COCF₃ |
| CH₂C≡CH | CO₂CH₃ | COCF₃ |
| CycPr | CO₂CH₃ | COCF₃ |
| CH₂CycPr | CO₂CH₃ | COCF₃ |
| Me | 6-chloro-pyridin-3-ylmethyl | COCF₃ |
| Et | 6-chloro-pyridin-3-ylmethyl | COCF₃ |
| Pr | 6-chloro-pyridin-3-ylmethyl | COCF₃ |
| CH₂CF₃ | 6-chloro-pyridin-3-ylmethyl | COCF₃ |
| CH₂C≡CH | 6-chloro-pyridin-3-ylmethyl | COCF₃ |
| CycPr | 6-chloro-pyridin-3-ylmethyl | COCF₃ |
| CH₂CycPr | 6-chloro-pyridin-3-ylmethyl | COCF₃ |
| Me | 2-chloro-thiazol-5-ylmethyl | COCF₃ |
| Et | 2-chloro-thiazol-5-ylmethyl | COCF₃ |
| Pr | 2-chloro-thiazol-5-ylmethyl | COCF₃ |
| CH₂CF₃ | 2-chloro-thiazol-5-ylmethyl | COCF₃ |
| CH₂C≡CH | 2-chloro-thiazol-5-ylmethyl | COCF₃ |
| CycPr | 2-chloro-thiazol-5-ylmethyl | COCF₃ |
| CH₂CycPr | 2-chloro-thiazol-5-ylmethyl | COCF₃ |

TABLE 10

| R¹ | R⁶ | G$^X$ |
|---|---|---|
| Me | Me | CSCF₃ |
| Et | Me | CSCF₃ |
| Pr | Me | CSCF₃ |
| CH₂CF₃ | Me | CSCF₃ |
| CH₂C≡CH | Me | CSCF₃ |
| CycPr | Me | CSCF₃ |
| CH₂CycPr | Me | CSCF₃ |
| Me | Et | CSCF₃ |
| Et | Et | CSCF₃ |
| Pr | Et | CSCF₃ |
| CH₂CF₃ | Et | CSCF₃ |
| CH₂C≡CH | Et | CSCF₃ |
| CycPr | Et | CSCF₃ |
| CH₂CycPr | Et | CSCF₃ |
| Me | CycPr | CSCF₃ |
| Et | CycPr | CSCF₃ |
| Pr | CycPr | CSCF₃ |
| CH₂CF₃ | CycPr | CSCF₃ |
| CH₂C≡CH | CycPr | CSCF₃ |
| CycPr | CycPr | CSCF₃ |
| CH₂CycPr | CycPr | CSCF₃ |

TABLE 11

| R$^1$ | R$^6$ | G$^X$ |
|---|---|---|
| Me | CH$_2$CycPr | CSCF$_3$ |
| Et | CH$_2$CycPr | CSCF$_3$ |
| Pr | CH$_2$CycPr | CSCF$_3$ |
| CH$_2$CF$_3$ | CH$_2$CycPr | CSCF$_3$ |
| CH$_2$C≡CH | CH$_2$CycPr | CSCF$_3$ |
| CycPr | CH$_2$CycPr | CSCF$_3$ |
| CH$_2$CycPr | CH$_2$CycPr | CSCF$_3$ |
| Me | CH$_2$C≡CH | CSCF$_3$ |
| Et | CH$_2$C≡CH | CSCF$_3$ |
| Pr | CH$_2$C≡CH | CSCF$_3$ |
| CH$_2$CF$_3$ | CH$_2$C≡CH | CSCF$_3$ |
| CH$_2$C≡CH | CH$_2$C≡CH | CSCF$_3$ |
| CycPr | CH$_2$C≡CH | CSCF$_3$ |
| CH$_2$CycPr | CH$_2$C≡CH | CSCF$_3$ |
| Me | CH$_2$OCH$_3$ | CSCF$_3$ |
| Et | CH$_2$OCH$_3$ | CSCF$_3$ |
| Pr | CH$_2$OCH$_3$ | CSCF$_3$ |
| CH$_2$CF$_3$ | CH$_2$OCH$_3$ | CSCF$_3$ |
| CH$_2$C≡CH | CH$_2$OCH$_3$ | CSCF$_3$ |
| CycPr | CH$_2$OCH$_3$ | CSCF$_3$ |
| CH$_2$CycPr | CH$_2$OCH$_3$ | CSCF$_3$ |

TABLE 12

| R$^1$ | R$^6$ | G$^X$ |
|---|---|---|
| Me | CO$_2$CH$_3$ | CSCF$_3$ |
| Et | CO$_2$CH$_3$ | CSCF$_3$ |
| Pr | CO$_2$CH$_3$ | CSCF$_3$ |
| CH$_2$CF$_3$ | CO$_2$CH$_3$ | CSCF$_3$ |
| CH$_2$C≡CH | CO$_2$CH$_3$ | CSCF$_3$ |
| CycPr | CO$_2$CH$_3$ | CSCF$_3$ |
| CH$_2$CycPr | CO$_2$CH$_3$ | CSCF$_3$ |
| Me | 6-chloro-pyridin-3-ylmethyl | CSCF$_3$ |
| Et | 6-chloro-pyridin-3-ylmethyl | CSCF$_3$ |
| Pr | 6-chloro-pyridin-3-ylmethyl | CSCF$_3$ |
| CH$_2$CF$_3$ | 6-chloro-pyridin-3-ylmethyl | CSCF$_3$ |
| CH$_2$C≡CH | 6-chloro-pyridin-3-ylmethyl | CSCF$_3$ |
| CycPr | 6-chloro-pyridin-3-ylmethyl | CSCF$_3$ |
| CH$_2$CycPr | 6-chloro-pyridin-3-ylmethyl | CSCF$_3$ |
| Me | 2-chloro-thiazol-5-ylmethyl | CSCF$_3$ |
| Et | 2-chloro-thiazol-5-ylmethyl | CSCF$_3$ |
| Pr | 2-chloro-thiazol-5-ylmethyl | CSCF$_3$ |
| CH$_2$CF$_3$ | 2-chloro-thiazol-5-ylmethyl | CSCF$_3$ |
| CH$_2$C≡CH | 2-chloro-thiazol-5-ylmethyl | CSCF$_3$ |
| CycPr | 2-chloro-thiazol-5-ylmethyl | CSCF$_3$ |
| CH$_2$CycPr | 2-chloro-thiazol-5-ylmethyl | CSCF$_3$ |

TABLE 13

| R$^1$ | R$^6$ | G$^X$ |
|---|---|---|
| Me | Me | CS(O)CF$_3$ |
| Et | Me | CS(O)CF$_3$ |
| Pr | Me | CS(O)CF$_3$ |
| CH$_2$CF$_3$ | Me | CS(O)CF$_3$ |
| CH$_2$C≡CH | Me | CS(O)CF$_3$ |
| CycPr | Me | CS(O)CF$_3$ |
| CH$_2$CycPr | Me | CS(O)CF$_3$ |
| Me | Et | CS(O)CF$_3$ |
| Et | Et | CS(O)CF$_3$ |
| Pr | Et | CS(O)CF$_3$ |
| CH$_2$CF$_3$ | Et | CS(O)CF$_3$ |
| CH$_2$C≡CH | Et | CS(O)CF$_3$ |
| CycPr | Et | CS(O)CF$_3$ |
| CH$_2$CycPr | Et | CS(O)CF$_3$ |
| Me | CycPr | CS(O)CF$_3$ |
| Et | CycPr | CS(O)CF$_3$ |
| Pr | CycPr | CS(O)CF$_3$ |
| CH$_2$CF$_3$ | CycPr | CS(O)CF$_3$ |
| CH$_2$C≡CH | CycPr | CS(O)CF$_3$ |
| CycPr | CycPr | CS(O)CF$_3$ |
| CH$_2$CycPr | CycPr | CS(O)CF$_3$ |

TABLE 14

| R$^1$ | R$^6$ | G$^X$ |
|---|---|---|
| Me | CH$_2$CycPr | CS(O)CF$_3$ |
| Et | CH$_2$CycPr | CS(O)CF$_3$ |
| Pr | CH$_2$CycPr | CS(O)CF$_3$ |
| CH$_2$CF$_3$ | CH$_2$CycPr | CS(O)CF$_3$ |
| CH$_2$C≡CH | CH$_2$CycPr | CS(O)CF$_3$ |
| CycPr | CH$_2$CycPr | CS(O)CF$_3$ |
| CH$_2$CycPr | CH$_2$CycPr | CS(O)CF$_3$ |
| Me | CH$_2$C≡CH | CS(O)CF$_3$ |
| Et | CH$_2$C≡CH | CS(O)CF$_3$ |
| Pr | CH$_2$C≡CH | CS(O)CF$_3$ |
| CH$_2$CF$_3$ | CH$_2$C≡CH | CS(O)CF$_3$ |
| CH$_2$C≡CH | CH$_2$C≡CH | CS(O)CF$_3$ |
| CycPr | CH$_2$C≡CH | CS(O)CF$_3$ |
| CH$_2$CycPr | CH$_2$C≡CH | CS(O)CF$_3$ |
| Me | CH$_2$OCH$_3$ | CS(O)CF$_3$ |
| Et | CH$_2$OCH$_3$ | CS(O)CF$_3$ |
| Pr | CH$_2$OCH$_3$ | CS(O)CF$_3$ |
| CH$_2$CF$_3$ | CH$_2$OCH$_3$ | CS(O)CF$_3$ |
| CH$_2$C≡CH | CH$_2$OCH$_3$ | CS(O)CF$_3$ |
| CycPr | CH$_2$OCH$_3$ | CS(O)CF$_3$ |
| CH$_2$CycPr | CH$_2$OCH$_3$ | CS(O)CF$_3$ |

TABLE 15

| R$^1$ | R$^6$ | G$^X$ |
|---|---|---|
| Me | CO$_2$CH$_3$ | CS(O)CF$_3$ |
| Et | CO$_2$CH$_3$ | CS(O)CF$_3$ |
| Pr | CO$_2$CH$_3$ | CS(O)CF$_3$ |
| CH$_2$CF$_3$ | CO$_2$CH$_3$ | CS(O)CF$_3$ |
| CH$_2$C≡CH | CO$_2$CH$_3$ | CS(O)CF$_3$ |
| CycPr | CO$_2$CH$_3$ | CS(O)CF$_3$ |
| CH$_2$CycPr | CO$_2$CH$_3$ | CS(O)CF$_3$ |
| Me | 6-chloro-pyridin-3-ylmethyl | CS(O)CF$_3$ |
| Et | 6-chloro-pyridin-3-ylmethyl | CS(O)CF$_3$ |
| Pr | 6-chloro-pyridin-3-ylmethyl | CS(O)CF$_3$ |
| CH$_2$CF$_3$ | 6-chloro-pyridin-3-ylmethyl | CS(O)CF$_3$ |
| CH$_2$C≡CH | 6-chloro-pyridin-3-ylmethyl | CS(O)CF$_3$ |
| CycPr | 6-chloro-pyridin-3-ylmethyl | CS(O)CF$_3$ |
| CH$_2$CycPr | 6-chloro-pyridin-3-ylmethyl | CS(O)CF$_3$ |
| Me | 2-chloro-thiazol-5-ylmethyl | CS(O)CF$_3$ |
| Et | 2-chloro-thiazol-5-ylmethyl | CS(O)CF$_3$ |
| Pr | 2-chloro-thiazol-5-ylmethyl | CS(O)CF$_3$ |
| CH$_2$CF$_3$ | 2-chloro-thiazol-5-ylmethyl | CS(O)CF$_3$ |
| CH$_2$C≡CH | 2-chloro-thiazol-5-ylmethyl | CS(O)CF$_3$ |
| CycPr | 2-chloro-thiazol-5-ylmethyl | CS(O)CF$_3$ |
| CH$_2$CycPr | 2-chloro-thiazol-5-ylmethyl | CS(O)CF$_3$ |

TABLE 16

| R$^1$ | R$^6$ | G$^X$ |
|---|---|---|
| Me | Me | CS(O)$_2$CF$_3$ |
| Et | Me | CS(O)$_2$CF$_3$ |
| Pr | Me | CS(O)$_2$CF$_3$ |
| CH$_2$CF$_3$ | Me | CS(O)$_2$CF$_3$ |
| CH$_2$C≡CH | Me | CS(O)$_2$CF$_3$ |
| CycPr | Me | CS(O)$_2$CF$_3$ |
| CH$_2$CycPr | Me | CS(O)$_2$CF$_3$ |
| Me | Et | CS(O)$_2$CF$_3$ |
| Et | Et | CS(O)$_2$CF$_3$ |
| Pr | Et | CS(O)$_2$CF$_3$ |
| CH$_2$CF$_3$ | Et | CS(O)$_2$CF$_3$ |
| CH$_2$C≡CH | Et | CS(O)$_2$CF$_3$ |
| CycPr | Et | CS(O)$_2$CF$_3$ |
| CH$_2$CycPr | Et | CS(O)$_2$CF$_3$ |

TABLE 16-continued

| R$^1$ | R$^6$ | G$^X$ |
|---|---|---|
| Me | CycPr | CS(O)$_2$CF$_3$ |
| Et | CycPr | CS(O)$_2$CF$_3$ |
| Pr | CycPr | CS(O)$_2$CF$_3$ |
| CH$_2$CF$_3$ | CycPr | CS(O)$_2$CF$_3$ |
| CH$_2$C≡CH | CycPr | CS(O)$_2$CF$_3$ |
| CycPr | CycPr | CS(O)$_2$CF$_3$ |
| CH$_2$CycPr | CycPr | CS(O)$_2$CF$_3$ |

TABLE 17

| R$^1$ | R$^6$ | G$^X$ |
|---|---|---|
| Me | CH$_2$CycPr | CS(O)$_2$CF$_3$ |
| Et | CH$_2$CycPr | CS(O)$_2$CF$_3$ |
| Pr | CH$_2$CycPr | CS(O)$_2$CF$_3$ |
| CH$_2$CF$_3$ | CH$_2$CycPr | CS(O)$_2$CF$_3$ |
| CH$_2$C≡CH | CH$_2$CycPr | CS(O)$_2$CF$_3$ |
| CycPr | CH$_2$CycPr | CS(O)$_2$CF$_3$ |
| CH$_2$CycPr | CH$_2$CycPr | CS(O)$_2$CF$_3$ |
| Me | CH$_2$C≡CH | CS(O)$_2$CF$_3$ |
| Et | CH$_2$C≡CH | CS(O)$_2$CF$_3$ |
| Pr | CH$_2$C≡CH | CS(O)$_2$CF$_3$ |
| CH$_2$CF$_3$ | CH$_2$C≡CH | CS(O)$_2$CF$_3$ |
| CH$_2$C≡CH | CH$_2$C≡CH | CS(O)$_2$CF$_3$ |
| CycPr | CH$_2$C≡CH | CS(O)$_2$CF$_3$ |
| CH$_2$CycPr | CH$_2$C≡CH | CS(O)$_2$CF$_3$ |
| Me | CH$_2$OCH$_3$ | CS(O)$_2$CF$_3$ |
| Et | CH$_2$OCH$_3$ | CS(O)$_2$CF$_3$ |
| Pr | CH$_2$OCH$_3$ | CS(O)$_2$CF$_3$ |
| CH$_2$CF$_3$ | CH$_2$OCH$_3$ | CS(O)$_2$CF$_3$ |
| CH$_2$C≡CH | CH$_2$OCH$_3$ | CS(O)$_2$CF$_3$ |
| CycPr | CH$_2$OCH$_3$ | CS(O)$_2$CF$_3$ |
| CH$_2$CycPr | CH$_2$OCH$_3$ | CS(O)$_2$CF$_3$ |

TABLE 18

| R$^1$ | R$^6$ | G$^X$ |
|---|---|---|
| Me | CO$_2$CH$_3$ | CS(O)$_2$CF$_3$ |
| Et | CO$_2$CH$_3$ | CS(O)$_2$CF$_3$ |
| Pr | CO$_2$CH$_3$ | CS(O)$_2$CF$_3$ |
| CH$_2$CF$_3$ | CO$_2$CH$_3$ | CS(O)$_2$CF$_3$ |
| CH$_2$C≡CH | CO$_2$CH$_3$ | CS(O)$_2$CF$_3$ |
| CycPr | CO$_2$CH$_3$ | CS(O)$_2$CF$_3$ |
| CH$_2$CycPr | CO$_2$CH$_3$ | CS(O)$_2$CF$_3$ |
| Me | 6-chloro-pyridin-3-ylmethyl | CS(O)$_2$CF$_3$ |
| Et | 6-chloro-pyridin-3-ylmethyl | CS(O)$_2$CF$_3$ |
| Pr | 6-chloro-pyridin-3-ylmethyl | CS(O)$_2$CF$_3$ |
| CH$_2$CF$_3$ | 6-chloro-pyridin-3-ylmethyl | CS(O)$_2$CF$_3$ |
| CH$_2$C≡CH | 6-chloro-pyridin-3-ylmethyl | CS(O)$_2$CF$_3$ |
| CycPr | 6-chloro-pyridin-3-ylmethyl | CS(O)$_2$CF$_3$ |
| CH$_2$CycPr | 6-chloro-pyridin-3-ylmethyl | CS(O)$_2$CF$_3$ |
| Me | 2-chloro-thiazol-5-ylmethyl | CS(O)$_2$CF$_3$ |
| Et | 2-chloro-thiazol-5-ylmethyl | CS(O)$_2$CF$_3$ |
| Pr | 2-chloro-thiazol-5-ylmethyl | CS(O)$_2$CF$_3$ |
| CH$_2$CF$_3$ | 2-chloro-thiazol-5-ylmethyl | CS(O)$_2$CF$_3$ |
| CH$_2$C≡CH | 2-chloro-thiazol-5-ylmethyl | CS(O)$_2$CF$_3$ |
| CycPr | 2-chloro-thiazol-5-ylmethyl | CS(O)$_2$CF$_3$ |
| CH$_2$CycPr | 2-chloro-thiazol-5-ylmethyl | CS(O)$_2$CF$_3$ |

(In [Table 1] to [Table 18] above, Me represents a methyl group, Et represents an ethyl group, Pr represents a n-propyl group, and CycPr represents a cyclopropyl group.)

In the formula (1), compounds of the present invention wherein n is 1, $R^2$, $R^3$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^2$, $R^3$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^2$, $R^3$, $R^4$ and $R^5$ are a hydrogen atom, $G^1$ is a nitrogen atom, $G^2$, $G^4$ and $G^5$ are =CH—, Q is a sulfur atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^2$, $R^3$, $R^4$ and $R^5$ are a hydrogen atom, $G^1$ is a nitrogen atom, $G^2$, $G^4$ and $G^5$ are =CH—, Q is a sulfur atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^2$, $R^3$, $R^4$ and $R^5$ are a hydrogen atom, $G^1$ is a nitrogen atom, $G^2$, $G^4$ and $G^5$ are =CH—, Q is a sulfur atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a fluorine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a fluorine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a fluorine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a chlorine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a chlorine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a chlorine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a bromine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a bromine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a bromine atom, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a methyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a methyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a methyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a trifluoromethyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a trifluoromethyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a trifluoromethyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a trifluoromethoxy group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a trifluoromethoxy group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a trifluoromethoxy group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a 2-pyridyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a 2-pyridyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a 2-pyridyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a 5-trifluoromethyl-2-pyridyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a 5-trifluoromethyl-2-pyridyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a 5-trifluoromethyl-2-pyridyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a 2-pyrimidinyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a 2-pyrimidinyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a 2-pyrimidinyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a methoxycarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a methoxycarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a methoxycarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is an ethoxycarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is an ethoxycarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is an ethoxycarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is an aminocarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is an aminocarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is an aminocarbonyl group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is an amino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is an amino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is an amino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a methoxycarbonylamino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a methoxycarbonylamino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a methoxycarbonylamino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a tert-butyloxycarbonylamino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a tert-butyloxycarbonylamino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a tert-butyloxycarbonylamino group, $R^2$, $R^4$ and $R^5$ are a hydrogen atom, $G^1$ is a nitrogen atom, $G^2$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^2$, $R^3$, $R^4$ and $R^5$ are a hydrogen atom, $G^2$ is a nitrogen atom, $G^1$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^2$, $R^3$, $R^4$ and $R^5$ are a hydrogen atom, $G^2$ is a nitrogen atom, $G^1$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^2$, $R^3$, $R^4$ and $R^5$ are a hydrogen atom, $G^2$ is a nitrogen atom, $G^1$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^3$ is a trifluoromethyl group, $R^2$, $R^4$ and $R^5$ are a hydrogen atom, $G^2$ is a nitrogen atom, $G^3$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 1, $R^3$ is a trifluoromethyl group, $R^2$, $R^4$ and $R^5$ are a hydrogen atom, $G^2$ is a nitrogen atom, $G^3$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 2, $R^3$ is a trifluoromethyl group, $R^2$, $R^4$ and $R^5$ are a hydrogen atom, $G^2$ is a nitrogen atom, $G^3$, $G^4$ and $G^5$ are =CH—, Q is an oxygen atom, and $R^1$, $R^6$ and $G^3$ are the combinations shown in $R^1$, $R^6$ and $G^X$ in [Table 1] to [Table 18].

In the formula (1), compounds of the present invention wherein n is 0, $R^2$, $R^3$, $R^4$ and $R^5$ are a hydrogen atom, $G^1$ is a nitrogen atom, $G^3$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3] (wherein $G^2$ and $G^4$ represent the combinations shown in $G^x$ at the same time).

In the formula (1), compounds of the present invention wherein n is 1, $R^2$, $R^3$, $R^4$ and $R^5$ are a hydrogen atom, $G^1$ is a nitrogen atom, $G^3$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3] (wherein $G^2$ and $G^4$ represent the combinations shown in $G^x$ at the same time).

In the formula (1), compounds of the present invention wherein n is 2, $R^2$, $R^3$, $R^4$ and $R^5$ are a hydrogen atom, $G^1$ is a nitrogen atom, $G^3$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 0, $R^3$ is a trifluoromethyl group, $R^2$, $R^4$ and $R^5$ are a hydrogen atom, $G^1$ is a nitrogen atom, $G^3$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 1, $R^3$ is a trifluoromethyl group, $R^2$, $R^4$ and $R^5$ are a hydrogen atom, $G^1$ is a nitrogen atom, $G^3$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 2, $R^3$ is a trifluoromethyl group, $R^2$, $R^4$ and $R^5$ are a hydrogen atom, $G^1$ is a nitrogen atom, $G^3$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 0, $R^2$, $R^3$, $R^4$ and $R^5$ are a hydrogen atom, $G^3$ is a nitrogen atom, $G^1$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 1, $R^2$, $R^3$, $R^4$ and $R^5$ are a hydrogen atom, $G^3$ is a nitrogen atom, $G^1$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 2, $R^2$, $R^3$, $R^4$ and $R^5$ are a hydrogen atom, $G^3$ is a nitrogen atom, $G^1$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 0, $R^3$ is a trifluoromethyl group, $R^2$, $R^4$ and $R^5$ are a hydrogen atom, $G^3$ is a nitrogen atom, $G^1$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 1, $R^3$ is a trifluoromethyl group, $R^2$, $R^4$ and $R^5$ are a hydrogen atom, $G^3$ is a nitrogen atom, $G^1$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

In the formula (1), compounds of the present invention wherein n is 2, $R^3$ is a trifluoromethyl group, $R^2$, $R^4$ and $R^5$ are a hydrogen atom, $G^3$ is a nitrogen atom, $G^1$ and $G^5$ are =CH—, Q is an oxygen atom, and $R^1$, $R^6$, $G^2$ and $G^4$ are the combinations shown in $R^1$, $R^6$ and $G^X$ in [Table 1] to [Table 3](wherein $G^2$ and $G^4$ represent the combinations shown in $G^x$ at the same time).

Next, specific examples of the present intermediate compound represented by the formula (2) are shown below.

In the formula (2):

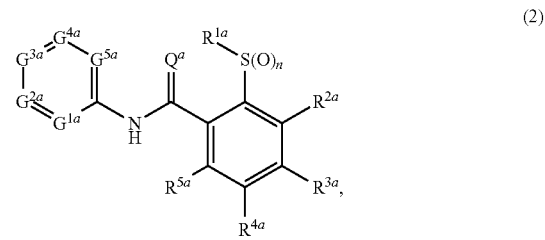

(2)

present intermediate compounds wherein n is 0, $R^{2a}$, $R^{3a}$, $R^{4a}$ and $R^{5a}$ are a hydrogen atom, $G^{2a}$ is a nitrogen atom, $G^{1a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

TABLE 19

| $R^{1a}$ | $G^X$ |
|---|---|
| Me | $CCF_3$ |
| Et | $CCF_3$ |
| Pr | $CCF_3$ |
| $CH_2CF_3$ | $CCF_3$ |
| $CH_2C\equiv CH$ | $CCF_3$ |
| CycPr | $CCF_3$ |
| $CH_2CycPr$ | $CCF_3$ |
| Me | $CCF_2CF_3$ |
| Et | $CCF_2CF_3$ |
| Pr | $CCF_2CF_3$ |
| $CH_2CF_3$ | $CCF_2CF_3$ |
| $CH_2C\equiv CH$ | $CCF_2CF_3$ |
| CycPr | $CCF_2CF_3$ |
| $CH_2CycPr$ | $CCF_2CF_3$ |
| Me | $COCF_3$ |
| Et | $COCF_3$ |
| Pr | $COCF_3$ |
| $CH_2CF_3$ | $COCF_3$ |
| $CH_2C\equiv CH$ | $COCF_3$ |
| CycPr | $COCF_3$ |
| $CH_2CycPr$ | $COCF_3$ |

TABLE 20

| $R^{1a}$ | $G^X$ |
|---|---|
| Me | $SCF_3$ |
| Et | $SCF_3$ |
| Pr | $SCF_3$ |
| $CH_2CF_3$ | $SCF_3$ |
| $CH_2C\equiv CH$ | $SCF_3$ |
| CycPr | $SCF_3$ |
| $CH_2CycPr$ | $SCF_3$ |
| Me | $S(O)CF_3$ |
| Et | $S(O)CF_3$ |
| Pr | $S(O)CF_3$ |
| $CH_2CF_3$ | $S(O)CF_3$ |
| $CH_2C\equiv CH$ | $S(O)CF_3$ |
| CycPr | $S(O)CF_3$ |
| $CH_2CycPr$ | $S(O)CF_3$ |
| Me | $S(O)_2CF_3$ |
| Et | $S(O)_2CF_3$ |
| Pr | $S(O)_2CF_3$ |
| $CH_2CF_3$ | $S(O)_2CF_3$ |
| $CH_2C\equiv CH$ | $S(O)_2CF_3$ |
| CycPr | $S(O)_2CF_3$ |
| $CH_2CycPr$ | $S(O)_2CF_3$ |

(In [Table 19] to [Table 20] above, Me represents a methyl group, Et represents an ethyl group, Pr represents a n-propyl group, and CycPr represents a cyclopropyl group.)

In the formula (2), present intermediate compounds wherein n is 1, $R^{2a}$, $R^{3a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{2a}$, $R^{3a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{2a}$, $R^{3a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is a sulfur atom, and $R^{1a}$ and $G^{3a}$ are the combinations shown in $R^{1a}$ and $G^X$ in [Table 19] to [Table 20].

In the formula (2), present intermediate compounds wherein n is 1, $R^{2a}$, $R^{3a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is a sulfur atom, and $R^{1a}$ and $G^{3a}$ are the combinations shown in $R^{1a}$ and $G^X$ in [Table 19] to [Table 20].

In the formula (2), present intermediate compounds wherein n is 2, $R^{2a}$, $R^{3a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is a sulfur atom, and $R^{1a}$ and $G^{3a}$ are the combinations shown in $R^1$ and $G^X$ in [Table 19] to [Table 20].

In the formula (2), present intermediate compounds wherein n is 0, $R^{3a}$ is a fluorine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a fluorine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a fluorine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a chlorine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a chlorine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a chlorine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a bromine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a bromine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a bromine atom, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^1$ and $G^X$ in [Table 19] to [Table 20].

In the formula (2), present intermediate compounds wherein n is 0, $R^{3a}$ is a methyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a methyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a methyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a trifluoromethyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a trifluoromethyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a trifluoromethyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a trifluoromethoxy group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a trifluoromethoxy group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a trifluoromethoxy group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a 2-pyridyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a 2-pyridyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a 2-pyridyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a 5-trifluoromethyl-2-pyridyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a 5-trifluoromethyl-2-pyridyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a 5-trifluoromethyl-2-pyridyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a 2-pyrimidinyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a 2-pyrimidinyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a 2-pyrimidinyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a methoxycarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a methoxycarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a methoxycarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is an ethoxycarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is an ethoxycarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is an ethoxycarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is an aminocarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is an aminocarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is an aminocarbonyl group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a methoxycarbonylamino group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a methoxycarbonylamino group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a methoxycarbonylamino group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a tert-butyloxycarbonylamino group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{3a}$ is a tert-butyloxycarbonylamino group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{3a}$ is a tert-butyloxycarbonylamino group, $R^{2a}$, $R^{4a}$ and $R^{5a}$ are a hydrogen atom, $G^{1a}$ is a nitrogen atom, $G^{2a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{2a}$, $R^{3a}$, $R^{4a}$ and $R^{5a}$ are a hydrogen atom, $G^{2a}$ is a nitrogen atom, $G^{1a}$, $G^{4a}$ and $G^{5a}$ are ═CH─, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 1, $R^{2a}$, $R^{3a}$, $R^{4a}$ and $R^{5a}$ are a hydrogen atom, $G^{2a}$ is a nitrogen atom, $G^{1a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 2, $R^{2a}$, $R^{3a}$, $R^{4a}$ and $R^{5a}$ are a hydrogen atom, $G^{2a}$ is a nitrogen atom, $G^{1a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

In the formula (2), present intermediate compounds wherein n is 0, $R^{3a}$ is a trifluoromethyl group, $R^{2a}$, $R^{4a}$ and $R^{5a}$ are a hydrogen atom, $G^{2a}$ is a nitrogen atom, $G^{1a}$, $G^{4a}$ and $G^{5a}$ are =CH—, $Q^a$ is an oxygen atom, and $R^{1a}$ and $G^{3a}$ are the combinations shown in $R^1$ and $G^X$ in [Table 19] to [Table 20].

In the formula (2), present intermediate compounds wherein n is 1, $R^{3a}$ is a trifluoromethyl group, $R^{2a}$, $R^{4a}$ and $R^{5a}$ are a hydrogen atom, $G^{2a}$ is a nitrogen atom, $G^{1a}$, $G^{4a}$ and $G^{5a}$ are =CH—, $Q^a$ is an oxygen atom, and $R^{1a}$ and $G^3$& are the combinations shown in $R^{1a}$ and $G^X$ in [Table 19] to [Table 20].

In the formula (2), present intermediate compounds wherein n is 2, $R^{3a}$ is a trifluoromethyl group, $R^{2a}$, $R^{4a}$ and $R^{5a}$ are a hydrogen atom, $G^{2a}$ is a nitrogen atom, $G^{1a}$, $G^{4a}$ and $G^{5a}$ are =CH—, $Q^a$ is an oxygen atom, and $R^{1a}$ and $G^{3a}$ are the combinations shown in $R^{1a}$ and $G^X$ in [Table 19] to [Table 20].

TABLE 21

| $R^{1a}$ |
|---|
| Me |
| Et |
| Pr |
| $CH_2CF_3$ |
| $CH_2C\equiv CH$ |
| CycPr |
| $CH_2$CycPr |

In the formula (2), present intermediate compounds wherein n is 0, $R^{2a}$, $R^{3a}$, $R^{4a}$ and $R^{5a}$ are a hydrogen atom, $G^{1a}$ is a nitrogen atom, $G^{3a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 1, $R^{2a}$, $R^{3a}$, $R^{4a}$ and $R^{5a}$ are a hydrogen atom, $G^{1a}$ is a nitrogen atom, $G^{3a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 2, $R^{2a}$, $R^{3a}$, $R^{4a}$ and $R^{5a}$ are a hydrogen atom, $G^{1a}$ is a nitrogen atom, $G^{3a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 0, $R^{3a}$ is a trifluoromethyl group, $R^{2a}$, $R^{4a}$ and $R^{5a}$ are a hydrogen atom, $G^{1a}$ is a nitrogen atom, $G^{3a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 1, $R^{3a}$ is a trifluoromethyl group, $R^{2a}$, $R^{4a}$ and $R^{5a}$ are a hydrogen atom, $G^{1a}$ is a nitrogen atom, $G^{3a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 2, $R^{3a}$ is a trifluoromethyl group, $R^{2a}$, $R^{4a}$ and $R^{5a}$ are a hydrogen atom, $G^{1a}$ is a nitrogen atom, $G^{3a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 0, $R^{2a}$, $R^{3a}$, $R^{4a}$ and $R^{5a}$ are a hydrogen atom, $G^{3a}$ is a nitrogen atom, $G^{1a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 1, $R^{2a}$, $R^{3a}$, $R^{4a}$ and $R^{5a}$ are a hydrogen atom, $G^{3a}$ is a nitrogen atom, $G^{1a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 2, $R^{2a}$, $R^{3a}$, $R^{4a}$ and $R^{5a}$ are a hydrogen atom, $G^{3a}$ is a nitrogen atom, $G^{1a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 0, $R^{3a}$ is a trifluoromethyl group, $R^{2a}$, $R^{4a}$ and $R^{5a}$ are a hydrogen atom, $G^{3a}$ is a nitrogen atom, $G^{1a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 1, $R^{3a}$ is a trifluoromethyl group, $R^{2a}$, $R^{4a}$ and $R^{5a}$ are a hydrogen atom, $G^{3a}$ is a nitrogen atom, $G^{1a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

In the formula (2), present intermediate compounds wherein n is 2, $R^{3a}$ is a trifluoromethyl group, $R^{2a}$, $R^{4a}$ and $R^{5a}$ are a hydrogen atom, $G^{3a}$ is a nitrogen atom, $G^{1a}$ and $G^{5a}$ are =CH—, $G^{2a}$ and $G^{4a}$ are =C(CF$_3$)—, $Q^a$ is an oxygen atom, and $R^{1a}$ is the combination shown in [Table 21].

Examples of the pest on which the compound of the present invention and the present intermediate compound have an effect include arthropod pests such as pest insects and pest mites and nematoda. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysarcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicoidea such as *Cimex lectularius*, and Psyliidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai*, *Homona magnanima*, *Archips fuscocupreanus*, and

*Cydia pomonella*, Gracillariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: *Culex* such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, *Stomoxys*, and Stomoxyidae.

Coleoptera: Corn rootworm such as *Diabrotica virgifera virgifera* and *Diabrotica undecimpunctata howardi*, Scarabaeidae such as *Anomala cuprea*, *Anomala rufocuprea*, and *Popillia japonica*, Curculionidae such as *Sitophilus zeamais*, *Lissorhoptrus oryzophilus*, *Callosobruchuys chienensis*, *Echinocnemus squameus*, *Anthonomus grandis*, and *Sphenophorus venatus*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Dermestidae such as *Anthrenus verbasci* and *Dermestes maculates*, Anobiidae such as *Lasioderma serricorne*, *Epilachna* such as *Epilachna vigintioctopunctata*, Lyctidae such as *Lyctus brunneus* and *Tomicus piniperda*, Bostrychidae, Ptinidae, Cerambycidae such as *Anoplophora malasiaca*, *Agriotes* spp., and *Paederus fuscipes*.

Orthoptera: *Locusta migratoria*, *Gryllotalpa africana*, *Oxya yezoensis*, *Oxya japonica*, and *Grylloidea*.

Siphonaptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like.

Mallophaga: *Dalmalinia ovis*, *Dalmalinia bovis*, *Menopon gallinae*, *Trichodectes canis*, *Felicola subrostrata*, and the like.

Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*, Vespidae, Bethylidae, and Tenthredinidae such as *Athalia rosae* and *Athalia japonica*.

Nematoda: *Aphelenchoides besseyi*, *Nothotylenchus acris*, *Meloidogyne incognita*, *Meloidogyne hapla*, *Meloidogyne javanica*, *Heterodera glycines*, *Globodera rostochiensis*, *Pratylenchus coffeae*, and *Pratylenchus neglectus*.

Blattodea: *Blattella germanica*, *Periplaneta fuliginosa*, *Periplaneta americana*, *Periplaneta brunnea*, and *Blatta orientalis*.

Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, *Sinocapritermes mushae*, and the like.

Acarina: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, *Phyllocoptruta citri*, *Aculops lycopersici*, *Calacarus carinatus*, *Acaphylla theavagrans*, *Eriophyes chibaensis*, and *Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus*, *Cheyletus malaccensis*, *Cheyletus moorei*, and *Cheyletiella yasguri*, Sarcoptidae such as *Octodectes cynotis* and *Sacroptes scabiei*, Demodicidae such as *Demodex canis*, Listrophoridae, Oribatei, Dermanyssidae such as *Ornithonyssus bacoti*, *Ornithonyssus sylvairum*, and *Dermanyssus gallinae*, Trombiculidae such as *Leptotrombidium akamushi*, Arachnida such as *Chiracanthium japonicum* and *Latrodectus hasseltii*, and the like.

Chilopoda: *Thereuonema hilgendorfi*, *Scolopendra subspinipes*, and the like.

Diplopoda: *Oxidus gracilis*, *Nedyopus tambanus*, and the like.

Isopoda: *Armadillidium vulgare*, and the like.

Gastropoda: *Limax marginatus*, *Limax flavus*, and the like.

The pest control agent of the present invention contains the compound of the present invention or the present intermediate compound and an inert carrier. The pest control agent of the present invention is usually obtained by mixing the compound of the present invention or the present intermediate compound and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, smoking agents, poisonous baits, resin formulations, shampoo agents, paste formulations, foam agents, carbon dioxide preparations, tablets, and the like. These formulations may be processed into mosquito repellent coils, electric mosquito repellent mats, mosquito repellent liquid formulations, smoking agents, fumigants, sheet formulations, spot-on agents, or oral treatment agents, and used.

The pest control agent of the present invention usually contains the compound of the present invention or the present intermediate compound in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like, and synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc.), ester adipates or stearic acid may be added to these base materials as necessary. The resin formulation is obtained by kneading a compound into the base material using an ordinary kneading apparatus, and then molding it by injection molding, extrusion molding, press molding or the like, and can be processed into a plate, film, taped, reticular or string resin formulation by further undergoing molding or cutting step as necessary. These resin formulation is processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant such as cheese flavor, onion flavor and peanut oil or the like are added as necessary.

The method for controlling pests of the present invention is carried out by applying an effective amount of the compound of the present invention or the present intermediate compound to a pest directly and/or a pest-infested area (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g per the amount of the compound of the present invention or the present intermediate compound per 10000 $m^2$. When the pest control agent of the present invention is formulated into an emulsifiable concentrate, a wettable powder, a flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly applied by being sprayed on a pest or a plant such as crops which should be protected from pests, and also may be applied on a soil in order to control a pest that infests in the soil of cultivated land.

Also, the resin formulation processed into a sheet or string can be also applied by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention or the present intermediate compound per 1 $m^2$ of an area to be treated, in the case of using it on a planar area, and is usually 0.01 to 500 mg in an amount of the compound of the present invention or the present intermediate compound per 1 $m^3$ of a space to be treated, in the case of using it in a space. When the pest control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, smoking agents, poisonous baits and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation on to an animal, when non-systemic control is intended. The amount of the compound of the present invention or the present intermediate compound when administered to an animal body is usually within the range from 0.1 to 1000 mg per 1 kg of the weight of an animal.

The pest control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (azalea, camellia, hydrangea, sasanqua, *Illicium religiosum*, cherry tree, tulip tree, crape myrtle, fragrant olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horsechestnut, etc.), sweet viburnum, Podocarpus macrophyllus, Japanese cedar, Japanese cypress, croton, spindle tree, Chinese hawthorn, etc.

Lawn: zoysia (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsettia, gladiolus, cattleya, daisy, cymbidium, begonia, etc.), bio-fuel plants (Jatropha, curcas, safflower, *Camelina alyssum*, switchgrass, miscanthus, reed canary grass, *Arundo donax*, kenaf, cassava, willow, algae, etc.), foliage plants, etc.

The "crops" also contains genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropylether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogenphosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, and 2,3,5,6-tetrafluoro-4-(methoxymethyl)benzyl(1RS,3RS; 1RS, 3SR)-2,2-dimethyl-3-(2-methyl-1-propenyl)cyclopropanecarboxylate, 2,3,5,6-tetrafluoro-4-(methoxymethyl)benzyl(EZ)-(1RS,3RS; 1RS,3SR)-2,2-dimethyl-3-(2-cyano-1-propenyl)cyclopropanecarboxylate.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof.

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, compounds represented by the following formula (K):

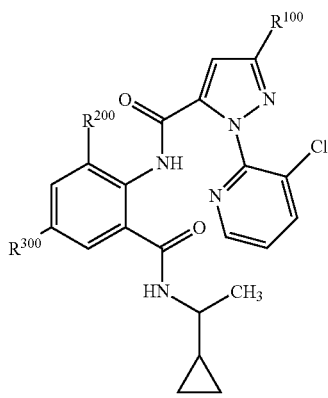

wherein
$R^{100}$ represents chlorine, bromine or a trifluoromethyl group,
$R^{200}$ represents chlorine, bromine or a methyl group, and
$R^{300}$ represents chlorine, bromine or a cyano group, and
compounds represented by the following formula (L):

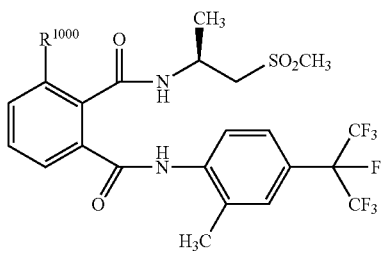

wherein
$R^{1000}$ represents chlorine, bromine or iodine.

Active Ingredients of Miticide acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol, methyisothiocyanate, morantel tartarate, and imicyafos.

Active Ingredients of Fungicide azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine fungicidal compounds such as fenpropimorph, tridemorph, and fenpropidin;

Benzimidazole fungicidal compounds such as carbendezim, benomyl, thiabendazole, and thiophanate-methyl;

procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active Ingredients of Herbicide (1) Phenoxy Fatty Acid Herbicidal Compounds
2,4-PA, MCP, MCPB, phenothiol, mecoprop, fluroxypyr, triclopyr, clomeprop, and naproanilide.

(2) Benzoate Herbicidal Compounds
2,3,6-TBA, dicamba, clopyralid, picloram, aminopyralid, quinclorac, and quinmerac.

(3) Urea Herbicidal Compounds
diuron, linuron, chlortoluron, isoproturon, fluometuron, isouron, tebuthiuron, methabenzthiazuron, cumyluron, daimuron, and methyl-daimuron.

(4) Triazine Herbicidal Compounds
atrazine, ametoryn, cyanazine, simazine, propazine, simetryn, dimethametryn, prometryn, metribuzin, triaziflam, and indaziflam.

(5) Bipyridinium Herbicidal Compounds
paraquat, and diquat.

(6) Hydroxybenzonitrile Herbicidal Compounds
bromoxynil, and ioxynil.

(7) Dinitroaniline Herbicidal Compounds
pendimethalin, prodiamine, and trifluralin.

(8) Organophosphorus Herbicidal Compounds
amiprofos-methyl, butamifos, bensulide, piperophos, anilofos, glyphosate, glufosinate, glufosinate-P, and bialaphos.

(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.

(10) Acid Amide Herbicidal Compounds
propanil, propyzamide, bromobutide, and etobenzanid.

(11) Chloroacetanilide Herbicidal Compounds
acetochlor, alachlor, butachlor, dimethenamid, propachlor, metazachlor, metolachlor, pretilachlor, thenylchlor, and pethoxamid.

(12) Diphenyl Ether Herbicidal Compounds
acifluorfen-sodium, bifenox, oxyfluorfen, lactofen, fomesafen, chlomethoxynil, and aclonifen.

(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds
benzofenap, pyrazolate, pyrazoxyfen, topramezone, and pyrasulfotole.

(15) Triketone Herbicidal Compounds
isoxaflutole, benzobicyclon, sulcotrione, mesotrione, tembotrione, and tefuryltrione.

(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.

(17) Trione Oxime Herbicidal Compounds
alloxydim-sodium, sethoxydim, butroxydim, clethodim, cloproxydim, cycloxydim, tepraloxydim, tralkoxydim, and profoxydim.

(18) Sulfonyl Urea Herbicidal Compounds chlorsulfuron, sulfometuron-methyl, metsulfuron-methyl, chlorimuron-ethyl, tribenuron-methyl, triasulfuron, metsulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds imazamethabenz-methyl, imazamethapyr, imazamox, imazapyr, imazaquin, and imazethapyr.

(20) Sulfonamide Herbicidal Compounds flumetsulam, metosulam, diclosulam, florasulam, cloransulam-methyl, penoxsulam, and pyroxsulam.

(21) Pyrimidinyloxybenzoate Herbicidal Compounds pyrithiobac-sodium, bispyribac-sodium, pyriminobac-methyl, pyribenzoxim, pyriftalid, and pyrimisulfan.

(22) Other Herbicidal Compounds bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist piperonyl butoxide, sesamex, sulfoxide, N-(2-ethylhexyl)-8,9,10-trinorborn-5-ene-2,3-dicarboximide (MGK 264), N-declyimidazole), WARF-antiresistant, TBPT, TPP, IBP, PSCP, CH$_3$I, t-phenylbutenone, diethyl maleate, DMC, FDMC, ETP, and ETN.

EXAMPLES

Hereinbelow, the present invention will be further described in detail by production examples, reference examples, formulation examples, test examples, and the like. However, the present invention is not limited to these examples.

First, the production examples for the production of the compounds of the present invention and the present intermediate compounds are shown below.

Production Example 1 (1)

A mixture of 0.81 g of 2-amino-5-trifluoromethylpyridine, 0.91 g of 2-ethylsulfanyl-benzoic acid, 1.15 g of EDCI hydrochloride, 0.06 g of HOBt and 10 mL of pyridine was stirred at 60° C. for 2 hours. A saturated aqueous sodium bicarbonate solution was added to the cooled reaction mixture, and the precipitated solid was taken by filtration and washed with acetonitrile to obtain 0.60 g of 2-ethylsulfanyl-N-(5-trifluoromethyl-pyridin-2-yl)-benzamide.

2-Ethylsulfanyl-N-(5-trifluoromethyl-pyridin-2-yl)-benzamide

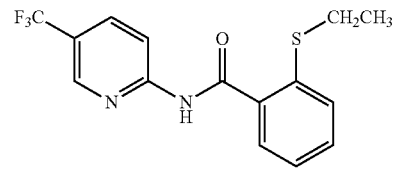 [SMILES: CCSc1ccccc1C(=O)Nc1ccc(C(F)(F)F)cn1]

$^1$H-NMR (CDCl$_3$) δ: 9.56 (1H, s), 8.55 (1H, d), 8.52 (1H, s), 7.98 (1H, dd), 7.81 (1H, d), 7.51-7.43 (2H, m), 7.36-7.30 (1H, m), 2.97 (2H, q), 1.32 (3H, t).

Production Example 1 (2)

0.03 g of 60% sodium hydride (oil-based) and 0.14 g of methyl iodide were added to a mixture of 0.15 g of 2-ethylsulfanyl-N-(5-trifluoromethyl-pyridin-2-yl)-benzamide and 2 mL of THF, and the mixture was stirred at room temperature for 5 hours. A saturated aqueous sodium bicarbonate solution was poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.10 g of 2-ethylsulfanyl-N-methyl-N-(5-trifluoromethyl-pyridin-2-yl)-benzamide (hereinafter, referred to as Compound of Present Invention 1).

Compound of Present Invention 1

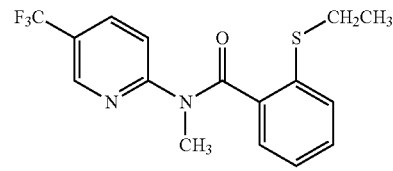 [SMILES: CCSc1ccccc1C(=O)N(C)c1ccc(C(F)(F)F)cn1]

$^1$H-NMR (CDCl$_3$) δ: 8.67 (1H, s), 7.77 (1H, dd), 7.67 (1H, d), 7.40-7.31 (2H, m), 7.24-7.16 (2H, m), 3.49 (3H, s), 2.95 (2H, q), 1.29 (3H, t).

Production Example 2 (1)

1.5 mL of ethyl mercaptan was added to a mixture of 3.83 g of 2-fluoro-4-trifluoromethylbenzoic acid, 10 mL of NMP and 15 g of cesium carbonate, and the mixture was stirred at 60° C. for 4 hours. A saturated aqueous sodium bicarbonate solution was added to the cooled reaction mixture, and the mixture was extracted with ethyl acetate. Hydrochloric acid was added to the aqueous layer, and the precipitated solid was taken by filtration and dried under reduced pressure to obtain 4.6 g of 2-ethylsulfanyl-4-trifluoromethylbenzoic acid.

2-Ethylsulfanyl-4-trifluoromethylbenzoic acid

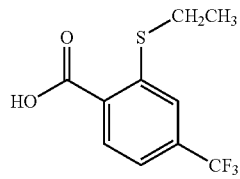

$^1$H-NMR (CDCl$_3$) δ: 8.22 (1H, d), 7.55 (1H, s), 7.43 (1H, d), 3.02 (2H, q), 1.43 (3H, t).

Production Example 2 (2)

A mixture of 1.62 g of 2-amino-5-trifluoromethylpyridine, 2.5 g of 2-ethylsulfanyl-4-trifluoromethylbenzoic acid, 2.3 g of EDCI hydrochloride, 0.13 g of HOBt and 5 mL of pyridine was stirred at room temperature for 2 hours and at 60° C. for 1 hour. A saturated aqueous sodium bicarbonate solution was added to the cooled reaction mixture, and the mixture was extracted with ethyl acetate. The organic layer was dried over anhydrous sodium sulfate and then concentrated under reduced pressure, and the resulting residue was applied to a silica gel column chromatography to obtain 2.56 g of 2-ethylsulfanyl-4-trifluoromethyl-N-(5-trifluoromethyl-pyridin-2-yl)-benzamide.

2-Ethylsulfanyl-4-trifluoromethyl-N-(5-trifluoromethyl-pyridin-2-yl)-benzamide

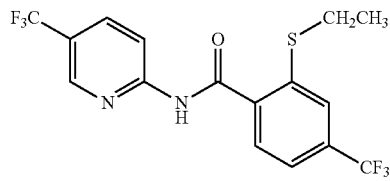 [SMILES: CCSc1cc(C(F)(F)F)ccc1C(=O)Nc1ccc(C(F)(F)F)cn1]

$^1$H-NMR (CDCl$_3$) δ: 9.28 (1H, s), 8.56 (1H, s), 8.53 (1H, d), 8.01 (1H, d), 7.87 (1H, d), 7.68 (1H, s), 7.56 (1H, d), 3.03 (2H, q), 1.36 (3H, t).

Production Example 2 (3)

0.12 g of 60% sodium hydride (oil-based) and 0.56 g of methyl iodide were added to a mixture of 0.78 g of 2-ethylsulfanyl-4-trifluoromethyl-N-(5-trifluoromethyl-pyridin-2-yl)-benzamide and 5 mL of THF, and the mixture was stirred at room temperature for 2 hours. 1 g of methyl iodide was added to the reaction mixture, and the mixture was stirred at room temperature for 2 hours. 1 g of methyl iodide was further added to the reaction mixture, and the mixture was stirred at room temperature for 1 hour. Water was added to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.59 g of 2-ethylsulfanyl-N-methyl-4-trifluoromethyl-N-(5-trifluoromethyl-pyridin-2-yl)-benzamide (hereinafter, referred to as Compound of Present Invention 2).

Compound of Present Invention 2

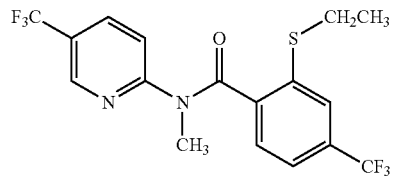 [SMILES: CCSc1cc(C(F)(F)F)ccc1C(=O)N(C)c1ccc(C(F)(F)F)cn1]

$^1$H-NMR (CDCl$_3$) δ: 8.66 (1H, s), 7.83 (1H, dd), 7.73 (1H, s), 7.57 (1H, s), 7.44 (1H, d), 7.34 (1H, d), 3.49 (3H, s), 3.01 (2H, q), 1.32 (3H, t).

Production Example 3

0.53 g of m-chloroperbenzoic acid (purity of 68%) was added to a mixture of 0.36 g of 2-ethylsulfanyl-N-methyl-4-trifluoromethyl-N-(5-trifluoromethyl-pyridin-2-yl)-benzamide and 3 mL of chloroform under ice cooling, and the mixture was stirred at room temperature for 3 hours. A saturated aqueous sodium bicarbonate solution and a saturated aqueous sodium thiosulfate solution were added to the reaction mixture, and the mixture was extracted with ethyl acetate. The organic layer was dried over anhydrous sodium sulfate and concentrated under reduced pressure. The resulting residue was applied to a silica gel column chromatography to obtain 0.37 g of 2-ethylsulfonyl-N-methyl-4-trifluoromethyl-N-(5-trifluoromethyl-pyridin-2-yl)-benzamide (hereinafter, referred to as Compound of Present Invention 3).

Compound of Present Invention 3

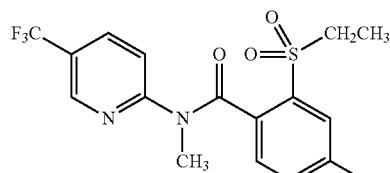

$^1$H-NMR (CDCl$_3$) δ: 8.70 (1H, s), 8.29 (1H, s), 8.12-7.19 (4H, m), 3.78-3.19 (5H, m), 1.37 (3H, t).

Production Example 4

0.21 g of potassium carbonate and 0.78 g of methyl iodide were added to a mixture of 0.39 g of 2-ethylsulfanyl-4-trifluoromethyl-N-(5-trifluoromethyl-pyridin-2-yl)-benzamide and 3 mL of acetone, and the mixture was stirred at room temperature for 1 hour. 3 mL of DMF was added to the reaction mixture, and the mixture was stirred at 60° C. for 1 hour. A saturated aqueous sodium bicarbonate solution was added to the cooled reaction mixture, and the mixture was extracted with ethyl acetate. The organic layer was dried over anhydrous sodium sulfate and then concentrated under reduced pressure, and the resulting residue was applied to a silica gel column chromatography to obtain 0.31 g of N-ethyl-2-ethylsulfanyl-4-trifluoromethyl-N-(5-trifluoromethyl-pyridin-2-yl)-benzamide (hereinafter, referred to as Compound of Present Invention 4).

Compound of Present Invention 4

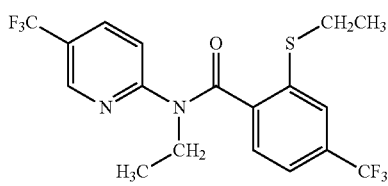 [SMILES: CCSc1cc(C(F)(F)F)ccc1C(=O)N(CC)c1ccc(C(F)(F)F)cn1]

¹H-NMR (CDCl₃) δ: 8.66 (1H, s), 7.77 (1H, dd), 7.60-7.27 (4H, m), 4.18-4.02 (2H, m), 3.01 (2H, q), 1.34 (3H, t), 1.25 (3H, t).

Production Example 5

0.27 g of m-chloroperbenzoic acid (purity of 68%) was added to a mixture of 0.20 g of N-ethyl-2-ethylsulfanyl-4-trifluoromethyl-N-(5-trifluoromethyl-pyridin-2-yl)-benzamide and 5 mL of chloroform under ice cooling, and the mixture was stirred at room temperature for 3 hours. A saturated aqueous sodium bicarbonate solution and a saturated aqueous sodium thiosulfate solution were added to the reaction mixture, and the mixture was extracted with ethyl acetate. The organic layer was dried over anhydrous sodium sulfate and concentrated under reduced pressure. The resulting residue was applied to a silica gel column chromatography to obtain 0.26 g of N-ethyl-2-ethylsulfonyl-4-trifluoromethyl-N-(5-trifluoromethyl-pyridin-2-yl)-benzamide (hereinafter, referred to as Compound of Present Invention 5).

Compound of Present Invention 5

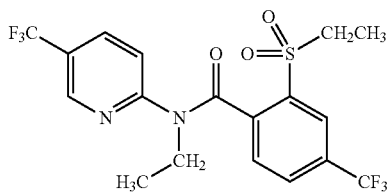

¹H-NMR (CDCl₃) δ: 8.73 (1H, s), 8.26 (1H, s), 7.84-7.10 (4H, m), 4.41-3.98 (2H, m), 3.81-3.49 (2H, m), 1.41-1.23 (6H, m).

Production Example 6 (1)

28 g of sodium pentafluoropropionate and 14 g of copper iodide were added to a mixture of 7.2 g of 2-chloro-5-iodopyridine, 75 mL of NMP and 75 mL of xylene under room temperature, and the mixture was heated to 150° C. and heated and stirred for 5.5 hours. After cooling the mixture to 80° C., 180 mL of a 40% aqueous methylamine solution was added in 4 parts every 2 hours, and the mixture was heated and stirred for 8.5 hours. After the reaction, the mixture was ice-cooled to 0° C., a 28% aqueous ammonia solution and a saturated aqueous sodium bicarbonate solution were added, and the mixture was extracted with MTBE. The organic layer was dried over anhydrous sodium sulfate and then concentrated under reduced pressure. The residue was applied to a silica gel column chromatography to obtain 4.6 g of methyl-(5-pentafluoroethyl-pyridin-2-yl)-amine.

Methyl-(5-pentafluoroethyl-pyridin-2-yl)-amine

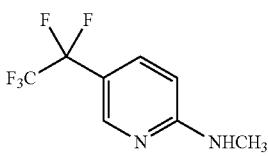

¹H-NMR (CDCl₃) δ: 8.28 (1H, d), 7.56 (1H, dd), 6.41 (1H, d), 5.74 (1H, brs), 2.95 (3H, d).

Production Example 6 (2)

0.23 g of oxalyl chloride was added to a mixture of 0.30 g of 2-ethylsulfanyl-4-trifluoromethylbenzoic acid, 10 mL of chloroform and 0.1 mL of DMF under ice cooling, and the mixture was stirred at room temperature for 2 hours. The reaction mixture was concentrated under reduced pressure, and added to a mixture of 0.22 g of methyl-(5-pentafluoroethyl-pyridin-2-yl)-amine and 1 mL of toluene, and the mixture was stirred at 100° C. for 1 hour. A saturated aqueous sodium bicarbonate solution was added to the cooled reaction mixture, and the mixture was extracted with ethyl acetate. The organic layer was dried over anhydrous sodium sulfate and then concentrated under reduced pressure, and the resulting residue was applied to a silica gel column chromatography to obtain 0.39 g of 2-ethylsulfanyl-N-methyl-N-(5-pentafluoroethyl-pyridin-2-yl)-4-trifluoromethyl-benzamide (hereinafter, referred to as Compound of Present Invention 6).

Compound of Present Invention 6

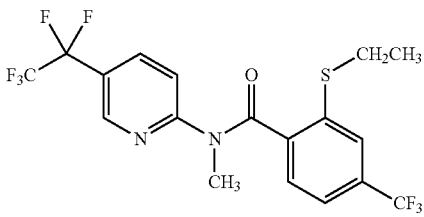 [SMILES: CCSc1cc(C(F)(F)F)ccc1C(=O)N(C)c1ccc(C(F)(F)C(F)(F)F)cn1]

¹H-NMR (CDCl₃) δ: 8.62 (1H, s), 7.85-7.78 (2H, m), 7.57 (1H, s), 7.46 (1H, d), 7.35 (1H, d), 3.49 (3H, s), 3.01 (2H, q), 1.32 (3H, t).

Production Example 7

0.39 g of m-chloroperbenzoic acid (purity of 68%) was added to a mixture of 0.30 g of 2-ethylsulfanyl-N-methyl-N-(5-pentafluoroethyl-pyridin-2-yl)-4-trifluoromethyl-benzamide and 5 mL of chloroform under ice cooling, and the mixture was stirred at room temperature for 2 hours. A saturated aqueous sodium bicarbonate solution and a saturated aqueous sodium thiosulfate solution were added to the reaction mixture, and the mixture was extracted with ethyl acetate. The organic layer was dried over anhydrous sodium sulfate and concentrated under reduced pressure. The resulting residue was applied to a silica gel column chromatography to obtain 0.31 g of 2-ethylsulfonyl-N-methyl-N-(5-pentafluoroethyl-pyridin-2-yl)-4-trifluoromethyl-benzamide (hereinafter, referred to as Compound of Present Invention 9).

Compound of Present Invention 9

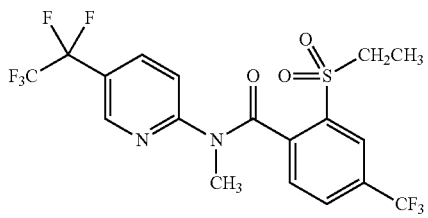 [SMILES: CCS(=O)(=O)c1cc(C(F)(F)F)ccc1C(=O)N(C)c1ccc(C(F)(F)C(F)(F)F)cn1]

¹H-NMR (CDCl₃) δ: 8.66 (1H, s), 8.30 (1H, s), 8.11-7.06 (4H, m), 3.77-3.06 (5H, m), 1.36 (3H, t).

Production Example 8 (1)

A mixture of 23.9 g of 2-chloro-5-iodopyridine, 14 ml of thiobenzoic acid, 1.90 g of copper iodide, 3.60 g of 1,10-phenanthroline, 35 ml of diisopropylethylamine and 200 ml of toluene was stirred at 110° C. for 4 hours. Water was added to the reaction mixture cooled to room temperature, and the insoluble matter was filtered with celite (registered trademark), then the filtered matter was washed with ethyl acetate, and the filtrate was extracted with ethyl acetate. The combined organic layer was dried over anhydrous magnesium sulfate and then concentrated under reduced pressure. The resulting residue was applied to a silica gel column chromatography to obtain 21.2 g of thiobenzoic acid S-(6-chloropyridin-3-yl)ester.

Thiobenzoic acid S-(6-chloropyridin-3-yl)ester

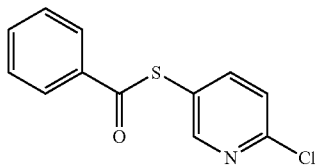 [SMILES: O=C(Sc1ccc(Cl)nc1)c1ccccc1]

¹H-NMR (CDCl₃) δ: 8.43-8.42 (1H, m), 8.01-7.98 (2H, m), 7.79-7.76 (1H, m), 7.66-7.61 (1H, m), 7.52-7.47 (2H, m), 7.44-7.41 (1H, m).

Production Example 8 (2)

A mixture of 21.2 g of thiobenzoic acid S-(6-chloropyridin-3-yl)ester, 17.6 g of potassium carbonate and 170 ml of methanol was stirred at room temperature for 2 hours. The reaction mixture was filtered, the filtered matter was washed with methanol, and then the filtrate was concentrated under reduced pressure. 170 ml of a 1 N aqueous sodium hydroxide solution was added to the resulting crude product, an aqueous solution of 56.0 g of potassium ferricyanide was added dropwise, and the mixture was stirred at room temperature for 2 hours. The reaction mixture was extracted with methyl-tert-butyl ether. The combined organic layer was dried over anhydrous magnesium sulfate, and then concentrated under reduced pressure. The residue was applied to a silica gel column chromatography to obtain 11.5 g of a compound represented by the following formula:

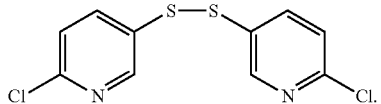 [SMILES: Clc1ccc(SSc2ccc(Cl)nc2)cn1]

¹H-NMR (CDCl³) δ: 8.41 (2H, d), 7.74 (2H, dd), 7.29 (2H, d).

Production Example 8 (3)

A mixture of 11.5 g of the compound represented by the following formula:

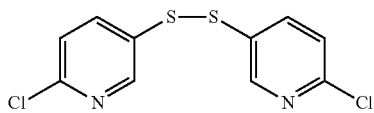 [SMILES: Clc1ccc(SSc2ccc(Cl)nc2)cn1]

and 133 ml of DMF was cooled to −50° C., and an excess amount of CF₃I gas was bubbled to dissolve the compound in DMF. 37.0 ml of tetrakisdimethylaminoethylenediamine was added dropwise at a rate such that the internal temperature does not surpass −40° C. Thereafter, the mixture was heated to −10° C. over 1 hour and further stirred at −10° C. for 2 hours. Water was added to the reaction mixture, and the mixture was heated to room temperature and then extracted with ethyl acetate. The combined organic layer was dried over anhydrous magnesium sulfate and then concentrated under reduced pressure. The resulting residue was applied to a silica gel column chromatography to obtain 7.25 g of 2-chloro-5-trifluoromethylsulfanylpyridine.

2-Chloro-5-trifluoromethylsulfanylpyridine

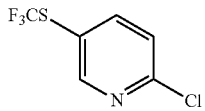

¹H-NMR (CDCl₃) δ: 8.62 (1H, d), 7.93 (1H, dd), 7.43 (1H, d).

Production Example 8 (4)

1.86 g of a 40% aqueous methylamine solution was added dropwise to a mixture of 1.71 g of 2-chloro-5-trifluoromethylsulfanylpyridine and 16 ml of NMP, and then the mixture was heated to 60° C. and heated and stirred for 2 hours. After cooling the mixture to room temperature, 1.66 g of potassium carbonate was added, and 1.86 g of a 40% aqueous methylamine solution was added dropwise. The mixture was heated to 60° C. and further heated and stirred for 2 hours. After cooling the mixture to room temperature, water was added, and the mixture was extracted with ethyl acetate. The combined organic layer was dried over anhydrous magnesium sulfate and then concentrated under reduced pressure. The resulting residue was applied to a silica gel column chromatography to obtain 1.52 g of methyl-(5-trifluoromethylsulfanylpyridin-2-yl)-amine.

Methyl-(5-trifluoromethylsulfanylpyridin-2-yl)-amine

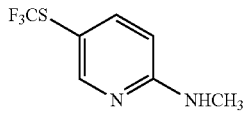

$^1$H-NMR (CDCl$_3$) δ: 8.28 (1H, d), 7.63 (1H, dd), 6.41-6.38 (1H, m), 4.90 (1H, brs), 2.96 (3H, d,).

Production Example 8 (5)

0.38 g of oxalyl chloride was added to a mixture of 0.55 g of 2-ethylsulfanyl-4-trifluoromethylbenzoic acid, 10 mL of chloroform and 0.1 mL of DMF under ice cooling, and the mixture was stirred at room temperature for 2 hours. The reaction mixture was concentrated under reduced pressure, and added to a mixture of 0.41 g of methyl-(5-trifluoromethylsulfanylpyridin-2-yl)-amine and 1 mL of toluene, and the mixture was stirred at 100° C. for 1 hour. A saturated aqueous sodium bicarbonate solution was added to the cooled reaction mixture, and the mixture was extracted with ethyl acetate. The organic layer was dried over anhydrous sodium sulfate and then concentrated under reduced pressure, and the resulting residue was applied to a silica gel column chromatography to obtain 0.77 g of 2-ethylsulfanyl-N-methyl-4-trifluoromethyl-N-(5-trifluoromethylsulfanyl-pyridin-2-yl)-benzamide (hereinafter, referred to as Compound of Present Invention 7).

Compound of Present Invention 7

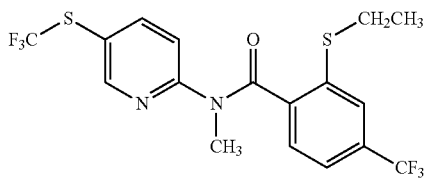 [SMILES: CCSc1cc(C(F)(F)F)ccc1C(=O)N(C)c1ccc(SC(F)(F)F)cn1]

$^1$H-NMR (CDCl$_3$) δ: 8.59 (1H, d), 7.86 (1H, dd), 7.74-7.63 (1H, m), 7.56 (1H, s), 7.43 (1H, d), 7.33 (1H, d), 3.48 (3H, s), 3.00 (2H, q), 1.32 (3H, t).

Production Example 9

0.82 g of m-chloroperbenzoic acid (purity of 68%) was added to a mixture of 0.63 g of 2-ethylsulfanyl-N-methyl-4-trifluoromethyl-N-(5-trifluoromethylsulfanyl-pyridin-2-yl)-benzamide and 10 mL of chloroform under ice cooling, and the mixture was stirred for 2 hours under ice cooling. A saturated aqueous sodium bicarbonate solution and a saturated aqueous sodium thiosulfate solution were added to the reaction mixture, and the mixture was extracted with ethyl acetate. The organic layer was dried over anhydrous sodium sulfate and concentrated under reduced pressure. The resulting residue was applied to a silica gel column chromatography to obtain 0.62 g of 2-ethylsulfonyl-N-methyl-4-trifluoromethyl-N-(5-trifluoromethylsulfanyl-pyridin-2-yl)-benzamide (hereinafter, referred to as Compound of Present Invention 10) and 0.04 g of 2-ethylsulfonyl-N-methyl-4-trifluoromethyl-N-(5-trifluoromethylsulfinyl-pyridin-2-yl)-benzamide (hereinafter, referred to as Compound of Present Invention 11).

Compound of Present Invention 10

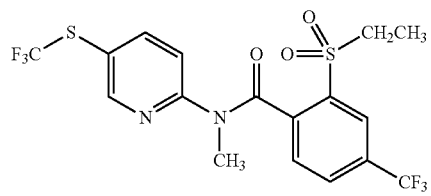 [SMILES: CCS(=O)(=O)c1cc(C(F)(F)F)ccc1C(=O)N(C)c1ccc(SC(F)(F)F)cn1]

$^1$H-NMR (CDCl$_3$) δ: 8.64 (1H, s), 8.28 (1H, s), 8.12-7.07 (4H, m), 3.77-3.15 (5H, m), 1.36 (3H, t).

Compound of Present Invention 11

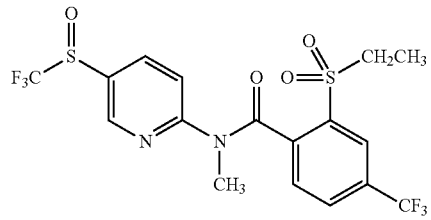 [SMILES: CCS(=O)(=O)c1cc(C(F)(F)F)ccc1C(=O)N(C)c1ccc(S(=O)C(F)(F)F)cn1]

$^1$H-NMR (CDCl$_3$) δ: 8.76 (1H, s), 8.31 (1H, s), 8.12-6.99 (4H, m), 3.90-3.26 (5H, m), 1.37 (3H, t).

The compounds described in the production examples described above and the compounds produced by the production method according to the method described in the production examples described above are shown in the tables.

The compounds of the present invention represented by the formula (1):

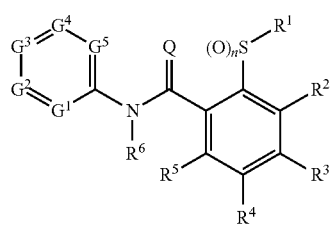

(1)

wherein R$^1$, R$^2$, R$^3$, R$^4$, R$^5$, R$^6$, G$^1$, G$^2$, G$^3$, G$^4$, G$^5$, n and Q represent the combinations shown in [Table 22] to [Table 24] shown below.

TABLE 22

| Compound of Present Invention | R¹ | R² | R³ | R⁴ | R⁵ | R⁶ | G¹ | G² | G³ | G⁴ | G⁵ | n | Q |
|---|---|---|---|---|---|---|---|---|---|---|---|---|---|
| 1 | Et | H | H | H | H | Me | N | CH | CCF$_3$ | CH | CH | 0 | 0 |
| 2 | Et | H | CF$_3$ | H | H | Me | N | CH | CCF$_3$ | CH | CH | 0 | 0 |
| 3 | Et | H | CF$_3$ | H | H | Me | N | CH | CCF$_3$ | CH | CH | 2 | 0 |
| 4 | Et | H | CF$_3$ | H | H | Et | N | CH | CCF$_3$ | CH | CH | 0 | 0 |
| 5 | Et | H | CF$_3$ | H | H | Et | N | CH | CCF$_3$ | CH | CH | 2 | 0 |
| 6 | Et | H | CF$_3$ | H | H | Me | N | CH | CCF$_2$CF$_3$ | CH | CH | 0 | 0 |
| 7 | Et | H | CF$_3$ | H | H | Me | N | CH | CCF$_3$ | CH | CH | 0 | 0 |
| 8 | Et | H | CF$_3$ | H | H | CH$_2$CycPr | N | CH | CCF$_3$ | CH | CH | 2 | 0 |
| 9 | Et | H | CF$_3$ | H | H | Me | N | CH | CCF$_2$CF$_3$ | CH | CH | 2 | 0 |
| 10 | Et | H | CF$_3$ | H | H | Me | N | CH | CSCF$_3$ | CH | CH | 2 | 0 |
| 11 | Et | H | CF$_3$ | H | H | Me | N | CH | CS(O)CF$_3$ | CH | CH | 2 | 0 |
| 12 | Et | H | CF$_3$ | H | H | Me | N | CH | CS(O)$_2$CF$_3$ | CH | CH | 2 | 0 |
| 13 | Et | H | H | H | H | Me | N | CH | CCF$_2$CF$_3$ | CH | CH | 0 | 0 |
| 14 | Et | H | H | H | H | Me | N | CH | CSCF$_3$ | CH | CH | 0 | 0 |
| 15 | Et | H | H | H | H | Me | N | CH | CCF$_2$CF$_3$ | CH | CH | 2 | 0 |
| 16 | Et | H | H | H | H | Me | N | CH | CSCF$_3$ | CH | CH | 2 | 0 |
| 17 | Et | H | H | H | H | Me | N | CH | CS(O)$_2$CF$_3$ | CH | CH | 2 | 0 |
| 18 | Et | H | H | H | H | Me | N | CH | CS(O)CF$_3$ | CH | CH | 2 | 0 |
| 19* | Et | H | H | H | H | Me | N | CH | CSCF$_3$ | CH | CH | 2 | 0 |
| 20 | Et | H | CF$_3$ | H | H | Me | N | CH | CCF$_2$CF$_3$ | CH | CH | 1 | 0 |
| 21 | Et | H | CF$_3$ | H | H | Me | N | CH | CSCF$_3$ | CH | CH | 1 | 0 |

TABLE 23

| Compound of Present Invention | R¹ | R² | R³ | R⁴ | R⁵ | R⁶ | G¹ | G² | G³ | G⁴ | G⁵ | n | Q |
|---|---|---|---|---|---|---|---|---|---|---|---|---|---|
| 22 | Et | H | CF$_3$ | H | H | CH$_2$CCH | N | CH | CCF$_3$ | CH | CH | 2 | 0 |
| 23 | Et | H | CF$_3$ | H | H | CH$_2$CCH | N | CH | CCF$_2$CF$_3$ | CH | CH | 2 | 0 |
| 24 | Et | H | CF$_3$ | H | H | CH$_2$CCH | N | CH | CSCF$_3$ | CH | CH | 2 | 0 |
| 25 | Et | H | CF$_3$ | H | H | CH$_2$OCH$_3$ | N | CH | CCF$_3$ | CH | CH | 2 | 0 |
| 26 | Et | H | CF$_3$ | H | H | CH$_2$OCH$_3$ | N | CH | CCF$_2$CF$_3$ | CH | CH | 2 | 0 |
| 27 | Et | H | CF$_3$ | H | H | CH$_2$OCH$_3$ | N | CH | CSCF$_3$ | CH | CH | 2 | 0 |
| 28 | Et | H | CF$_3$ | H | H | CO$_2$CH$_3$ | N | CH | CCF$_3$ | CH | CH | 2 | 0 |
| 29 | Et | H | CF$_3$ | H | H | CO$_2$CH$_3$ | N | CH | CCF$_2$CF$_3$ | CH | CH | 2 | 0 |
| 30 | Et | H | CF$_3$ | H | H | CO$_2$CH$_3$ | N | CH | CSCF$_3$ | CH | CH | 2 | 0 |
| 31 | Et | H | CF$_3$ | H | H | Me | CH | N | CCF$_3$ | CH | CH | 2 | 0 |
| 32 | Et | H | CF$_3$ | H | H | Me | CH | N | CCF$_2$CF$_3$ | CH | CH | 2 | 0 |
| 33 | Et | H | CF$_3$ | H | H | Me | CH | N | CSCF$_3$ | CH | CH | 2 | 0 |
| 34 | Et | H | CF$_3$ | H | H | Me | N | N | CCF$_3$ | CH | CH | 2 | 0 |
| 35 | Et | H | CF$_3$ | H | H | Me | N | N | CCF$_2$CF$_3$ | CH | CH | 2 | 0 |
| 36 | Et | H | CF$_3$ | H | H | Me | N | N | CSCF$_3$ | CH | CH | 2 | 0 |
| 37 | CycPr | H | CF$_3$ | H | H | Me | N | CH | CCF$_3$ | CH | N | 2 | 0 |
| 38 | CycPr | H | CF$_3$ | H | H | Me | N | CH | CCF$_2$CF$_3$ | CH | N | 2 | 0 |
| 39 | CycPr | H | CF$_3$ | H | H | Me | N | CH | CSCF$_3$ | CH | N | 2 | 0 |
| 40 | CH$_2$CycPr | H | CF$_3$ | H | H | Me | N | CH | CCF$_3$ | N | CH | 2 | 0 |
| 41 | CH$_2$CycPr | H | CF$_3$ | H | H | Me | N | CH | CCF$_2$CF$_3$ | N | CH | 2 | 0 |
| 42 | CH$_2$CycPr | H | CF$_3$ | H | H | Me | N | CH | CSCF$_3$ | N | CH | 2 | 0 |
| 43 | Et | H | CF$_3$ | H | H | CH$_2$CycPr | N | CH | CCF$_3$ | CH | CH | 0 | 0 |
| 44 | Et | H | Br | H | H | CH$_3$ | N | CH | CCF$_2$CF$_3$ | CH | CH | 2 | 0 |

TABLE 24

| Compound of Present Invention | R¹ | R² | R³ | R⁴ | R⁵ | R⁶ | G¹ | G² | G³ | G⁴ | G⁵ | n | Q |
|---|---|---|---|---|---|---|---|---|---|---|---|---|---|
| 45 | Et | H | CF$_3$ | H | H | CH$_3$ | N | CH | CF | CH | CH | 0 | 0 |
| 46 | Et | H | CF$_3$ | H | H | CH$_3$ | N | CH | CBr | CH | CH | 0 | 0 |
| 47 | Et | H | CF$_3$ | H | H | CH$_3$ | N | CH | CCl | CH | CH | 0 | 0 |
| 48 | Et | H | CF$_3$ | H | H | CH$_3$ | N | CH | CF | CH | CH | 2 | 0 |
| 49* | Et | H | CF$_3$ | H | H | CH$_3$ | N | CH | CF | CH | CH | 2 | 0 |
| 50 | Et | H | CF$_3$ | H | H | CH$_3$ | N | CH | CCH$_3$ | CH | CH | 2 | 0 |
| 51* | Et | H | CF$_3$ | H | H | CH$_3$ | N | CH | CCH$_3$ | CH | CH | 2 | 0 |
| 52 | Et | H | CF$_3$ | H | H | CH$_3$ | N | CH | CCl | CH | CH | 2 | 0 |
| 53* | Et | H | CF$_3$ | H | H | CH$_3$ | N | CH | CCl | CH | CH | 2 | 0 |
| 54 | Et | H | CF$_3$ | H | H | CH$_3$ | N | CH | CBr | CH | CH | 2 | 0 |
| 55* | Et | H | CF$_3$ | H | H | CH$_3$ | N | CH | CBr | CH | CH | 2 | 0 |
| 56 | Et | H | H | H | Cl | CH$_3$ | N | CH | CCF$_2$CF$_3$ | CH | CH | 2 | 0 |
| 57 | Et | H | H | H | H | CH$_3$ | N | CH | CSCF$_3$ | CH | CH | 1 | 0 |

TABLE 24-continued

| Compound of Present Invention | R¹ | R² | R³ | R⁴ | R⁵ | R⁶ | G¹ | G² | G³ | G⁴ | G⁵ | n | Q |
|---|---|---|---|---|---|---|---|---|---|---|---|---|---|
| 58 | Et | H | H | H | SO₂Et | CH₃ | N | CH | CCF₂CF₃ | CH | CH | 2 | 0 |
| 59 | Et | H | CF₃ | H | H | CH₃ | N | CCl | Cl | CH | CH | 2 | 0 |
| 60 | Et | H | CF₃ | H | H | CycPro | N | CH | CSCF₃ | CH | CH | 2 | 0 |
| 61 | Et | H | CF₃ | H | H | thietan-3-yl | N | CH | CSCF₃ | CH | CH | 2 | 0 |
| 62 | Et | H | CF₃ | H | H | CH₃ | N | CH | CCH₃ | CH | CH | 0 | 0 |

(In [Table 22] to [Table 24] described above, Et represents an ethyl group, and CycPr represents a cyclopropyl group.)

Here, "*" in the compound of the present invention in the tables means that the compound is an N-oxide. Specific examples are the following compounds.

Compound of Present Invention 19

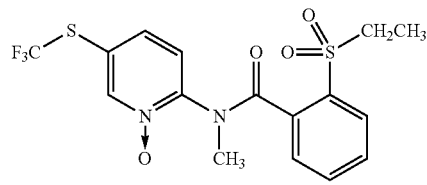 [SMILES: CCS(=O)(=O)c1ccccc1C(=O)N(C)c1ccc(SC(F)(F)F)c[n+]1[O-]]

Compound of Present Invention 49

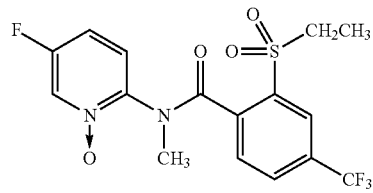 [SMILES: CCS(=O)(=O)c1cc(C(F)(F)F)ccc1C(=O)N(C)c1ccc(F)c[n+]1[O-]]

Compound of Present Invention 51

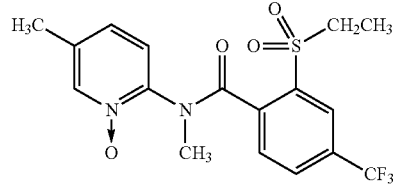

Compound of Present Invention 53

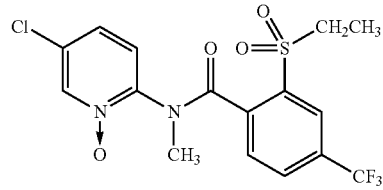 [SMILES: CCS(=O)(=O)c1cc(C(F)(F)F)ccc1C(=O)N(C)c1ccc(Cl)c[n+]1[O-]]

Compound of Present Invention 55

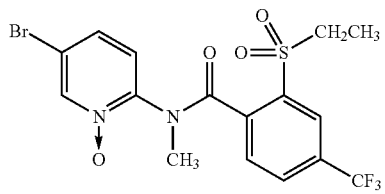

$^1$H-NMR data of the compounds of the present invention shown in [Table 22] to [Table 24] are shown below.

Compound of Present Invention 8
$^1$H-NMR (CDCl₃) δ: 8.72 (1H, s), 8.27 (1H, s), 7.79-7.44 (3H, m), 7.26-7.16 (1H, m), 4.41-4.22 (1H, m), 3.94-3.78 (1H, m), 3.74-3.46 (2H, m), 1.44-1.15 (4H, m), 0.61-0.03 (4H, m).

Compound of Present Invention 12
$^1$H-NMR (CDCl₃) δ: 9.00 (1H, s), 8.49-7.24 (5H, m), 3.72-3.28 (5H, m), 1.37 (3H, t).

Compound of Present Invention 13
$^1$H-NMR (CDCl₃) δ: 8.63 (1H, s), 7.76 (2H, s), 7.41-7.31 (2H, m), 7.25-7.18 (2H, m), 3.49 (3H, s), 2.95 (2H, q), 1.28 (3H, t).

Compound of Present Invention 14
$^1$H-NMR (CDCl₃) δ: 8.60 (1H, d), 7.80 (1H, dd), 7.64 (1H, d), 7.40-7.30 (2H, m), 7.24-7.15 (2H, m), 3.48 (3H, s), 2.94 (2H, q), 1.28 (3H, t).

Compound of Present Invention 15
$^1$H-NMR (CDCl₃) δ: 8.66 (1H, s), 8.04 (1H, d), 7.85-7.19 (5H, m), 3.90-3.21 (5H, m), 1.34 (3H, t).

Compound of Present Invention 16
$^1$H-NMR (CDCl₃) δ: 8.64 (1H, s), 8.03 (1H, d), 7.90-6.92 (5H, m), 3.81-3.23 (5H, m), 1.34 (3H, t).

Compound of Present Invention 17
$^1$H-NMR (CDCl₃) δ: 9.00 (1H, s), 8.25-7.12 (6H, m), 3.67-3.29 (5H, m), 1.43-1.20 (3H, m).

Compound of Present Invention 18
$^1$H-NMR (CDCl₃) δ: 8.76 (1H, s), 8.11-8.01 (1H, m), 7.76-7.18 (5H, m), 3.77-3.25 (5H, m), 1.43-1.27 (3H, m).

Compound of Present Invention 19
$^1$H-NMR (CDCl₃) δ: 8.43 (1H, s), 7.95 (1H, d), 7.74 (1H, d), 7.52-7.22 (4H, m), 3.72-3.34 (5H, m), 1.36-1.23 (3H, m).

Compound of Present Invention 20
$^1$H-NMR (CDCl₃) δ: 8.59 (1H, d), 8.35 (1H, s), 7.80 (1H, dd), 7.60 (1H, d), 7.38 (1H, d), 7.25 (1H, d), 3.57 (3H, s), 3.40-3.28 (1H, m), 3.06-2.93 (1H, m), 1.35 (3H, t).

Compound of Present Invention 21
$^1$H-NMR (CDCl₃) δ: 8.56 (1H, d), 8.35 (1H, d), 7.84 (1H, dd), 7.56 (1H, dd), 7.25-7.19 (2H, m), 3.57 (3H, s), 3.41-3.28 (1H, m), 3.05-2.92 (1H, m), 1.35 (3H, t).

Compound of Present Invention 43

¹H-NMR (CDCl₃) δ: 8.47 (1H, dd), 7.56 (1H, dd), 7.32 (1H, s), 7.22-7.04 (3H, m), 3.79 (2H, d), 2.83 (2H, q), 1.15 (3H, t), 1.01-0.90 (1H, m), 0.28-0.20 (2H, m), 0.03-0.06 (2H, m).

Compound of Present Invention 44

¹H-NMR (DMSO-D₆, 80° C.) δ: 8.71 (1H, s), 8.12 (1H, dd), 8.08 (1H, d), 7.95 (1H, dd), 7.87 (1H, s), 7.47 (1H, d), 3.45 (2H, q), 3.37 (3H, s), 1.19 (3H, t).

Compound of Present Invention 45

¹H-NMR (CDCl₃) δ: 8.24 (1H, s), 7.52 (1H, s), 7.42-7.19 (4H, m), 3.47 (3H, s), 3.01 (2H, q), 1.34 (3H, t).

Compound of Present Invention 46

¹H-NMR (CDCl₃) δ: 8.44 (1H, d), 7.67 (1H, d), 7.53 (1H, s), 7.42-7.27 (3H, m), 3.46 (3H, s), 3.00 (2H, q), 1.33 (3H, t).

Compound of Present Invention 47

¹H-NMR (CDCl₃) δ: 8.34 (1H, s), 7.53 (2H, s), 7.46-7.18 (3H, m), 3.47 (3H, s), 3.01 (2H, q), 1.33 (3H, t).

Compound of Present Invention 48

¹H-NMR (CDCl₃) δ: 8.38-7.12 (6H, m), 3.72-3.23 (5H, m), 1.40-1.29 (3H, m).

Compound of Present Invention 49

¹H-NMR (CDCl₃) δ: 8.21-8.13 (2H, m), 7.74-7.65 (3H, m), 6.90-6.83 (1H, m), 3.68-3.50 (2H, m), 3.40 (3H, s), 1.35 (3H, t).

Compound of Present Invention 50

¹H-NMR (CDCl₃) δ: 8.35-7.14 (6H, m), 3.75-3.23 (5H, m), 2.41-2.19 (3H, m), 1.40-1.30 (3H, m).

Compound of Present Invention 51

¹H-NMR (CDCl₃) δ: 8.17 (1H, s), 8.06 (1H, s), 7.77 (1H, d), 7.67 (1H, d), 7.52 (1H, d), 6.87 (1H, d), 3.69-3.52 (2H, m), 3.41 (3H, s), 2.23 (3H, s), 1.35 (3H, t).

Compound of Present Invention 52

¹H-NMR (CDCl₃) δ: 8.39 (1H, s), 8.34-7.17 (5H, m), 3.73-3.24 (5H, m), 1.36 (3H, t).

Compound of Present Invention 53

¹H-NMR (CDCl₃) δ: 8.21 (2H, d), 7.75-7.66 (2H, m), 7.63 (1H, d), 7.05 (1H, d), 3.68-3.50 (2H, m), 3.39 (3H, s), 1.35 (3H, t).

Compound of Present Invention 54

¹H-NMR (CDCl₃) δ: 8.56-7.13 (6H, m), 3.72-3.21 (5H, m), 1.41-1.23 (3H, m).

Compound of Present Invention 55

¹H-NMR (CDCl₃) δ: 8.36 (1H, s), 8.19 (1H, s), 7.75-7.66 (2H, m), 7.56 (1H, d), 7.18 (1H, d), 3.67-3.51 (2H, m), 3.39 (3H, s), 1.35 (3H, t).

Compound of Present Invention 56

¹H-NMR (DMSO-D₆) δ: 8.90-8.45 (1H, m), 8.32-7.31 (5H, m), 3.57-3.25 (5H, m), 1.19-1.08 (3H, m).

Compound of Present Invention 57

¹H-NMR (CDCl₃) δ: 8.60 (1H, d), 8.08 (1H, dd), 7.75 (1H, dd), 7.59 (1H, ddd), 7.34-7.29 (1H, m), 7.18 (1H, d), 7.09 (1H, dd), 3.57 (3H, s), 3.34-3.27 (1H, m), 3.00-2.93 (1H, m), 1.34 (3H, t).

Compound of Present Invention 58

¹H-NMR (DMSO-D₆) δ: 8.83-7.29 (6H, m), 3.54-3.16 (7H, m), 1.21-1.01 (6H, m).

Compound of Present Invention 59

¹H-NMR (CDCl₃) δ: 8.38-6.85 (5H, m), 3.73-3.20 (5H, m), 1.35 (3H, t).

Compound of Present Invention 60

¹H-NMR (CDCl₃) δ: 8.73-7.37 (6H, m), 3.59-3.14 (3H, m), 1.44-0.28 (7H, m).

Compound of Present Invention 61

¹H-NMR (CDCl₃) δ: 8.65 (1H, d), 8.22 (1H, s), 7.93 (1H, d), 7.79 (1H, dd), 7.48 (1H, d), 7.34 (1H, dd), 5.10-5.01 (1H, m), 4.60-4.38 (2H, m), 4.09-3.68 (2H, m), 3.28 (2H, q), 1.34 (3H, t).

Compound of Present Invention 62

¹H-NMR (CDCl₃) δ: 8.21 (1H, s), 7.49 (1H, s), 7.39-6.96 (4H, m), 3.50 (3H, s), 3.00 (2H, q), 2.27 (3H, s), 1.33 (3H, t).

Compounds Represented by Formula (M6):

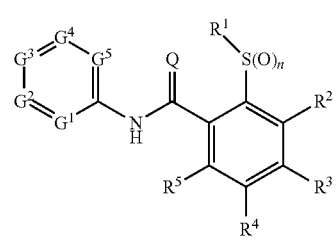

(M6)

wherein $R^1$, $R^2$, $R^3$, $R^4$, $R^5$, $G^1$, $G^2$, $G^3$, $G^4$, $G^5$, n and Q represent the combinations shown in [Table 25] shown below.

TABLE 25

| Intermediate Compound | $R^1$ | $R^2$ | $R^3$ | $R^4$ | $R^5$ | $G^1$ | $G^2$ | $G^3$ | $G^4$ | $G^5$ | n | Q |
|---|---|---|---|---|---|---|---|---|---|---|---|---|
| M6-1 | Et | H | H | H | H | N | CH | CCF₃ | CH | CH | 0 | O |
| M6-2 | Et | H | CF₃ | H | H | cSEt | N | CH | CCF₃ | CH | 0 | S |
| M6-3 | Et | H | H | H | H | N | CH | CCF₃ | CH | CH | 1 | O |
| M6-4 | Et | H | H | H | H | N | CH | CCF₃ | CH | CH | 2 | O |
| M6-5 | Et | H | CF₃ | H | H | N | CH | CCF₃ | CH | CH | 0 | O |
| M6-6 | Et | H | H | H | H | N | CH | CCF₃ | CH | CH | 0 | S |
| M6-7 | Et | H | CF₃ | H | H | N | CH | CCF₃ | CH | CH | 2 | O |
| M6-8 | Et | H | CF₃ | H | H | N | CH | CCF₃ | CH | CH | 1 | O |
| M6-9 | Et | H | CF₃ | H | H | cSEt | N | CH | CCF₃ | CH | 0 | O |
| M6-10 | Et | H | CF₃ | H | H | N | CH | CSCF₃ | CH | CH | 2 | O |
| M6-11 | Et | H | CF₃ | H | H | N | CH | CCF₂CF₃ | CH | CH | 0 | O |
| M6-12* | Et | H | CF₃ | H | H | N | CH | CCF₂CF₃ | CH | CH | 2 | O |

TABLE 25-continued

| Intermediate Compound | R¹ | R² | R³ | R⁴ | R⁵ | G¹ | G² | G³ | G⁴ | G⁵ | n | Q |
|---|---|---|---|---|---|---|---|---|---|---|---|---|
| M6-13 | Et | H | CF₃ | H | H | N | CH | CCF₂CF₃ | CH | CH | 2 | 0 |
| M6-14 | Et | H | CF₃ | H | H | N | CH | CSCF₃ | CH | CH | 0 | 0 |
| M6-15 | Et | H | H | H | SEt | N | CH | CCF2CF3 | CH | CH | 0 | 0 |
| M6-16 | Et | H | H | H | Cl | N | CH | CCF2CF3 | CH | CH | 2 | 0 |
| M6-17 | Et | H | H | H | SO2Et | N | CH | CCF2CF3 | CH | CH | 2 | 0 |
| M6-18* | Et | H | H | H | SO2Et | N | CH | CCF2CF3 | CH | CH | 2 | 0 |
| M6-19 | Et | H | CF3 | H | H | N | CH | CF | CH | CH | 0 | 0 |
| M6-20 | Et | H | CF3 | H | H | N | CH | CCl | CH | CH | 0 | 0 |
| M6-21 | Et | H | CF3 | H | H | N | CH | CBr | CH | CH | 0 | 0 |
| M6-22 | Et | H | CF3 | H | H | N | CH | CCH3 | CH | CH | 0 | 0 |

(In [Table 25] described above, Et represents an ethyl group.)

Here, "*" in the intermediate compound in the table means that the compound is an N-oxide. Specific examples are the following compounds.

Intermediate Compound M6-12

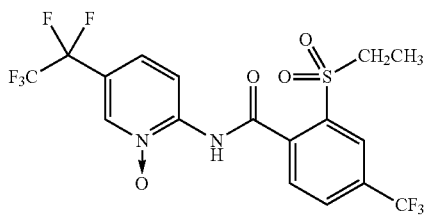 [SMILES: CCS(=O)(=O)c1cc(C(F)(F)F)ccc1C(=O)Nc1ccc(C(F)(F)C(F)(F)F)c[n+]1[O-]]

Intermediate Compound M6-18

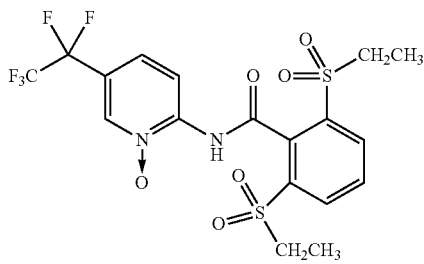 [SMILES: CCS(=O)(=O)c1cccc(S(=O)(=O)CC)c1C(=O)Nc1ccc(C(F)(F)C(F)(F)F)c[n+]1[O-]]

¹H-NMR data of the present intermediate compounds shown in [Table 25] are shown below.

Intermediate Compound M6-2
¹H-NMR (CDCl₃) δ: 8.92 (1H, s), 8.74 (1H, brs), 8.64 (1H, s), 7.66 (1H, d), 7.61 (1H, s), 7.51 (1H, d), 3.32 (2H, q), 3.05 (2H, q), 1.41-1.33 (6H, m).

Intermediate Compound M6-3
¹H-NMR (CDCl₃) δ: 10.47 (1H, s), 8.69 (1H, d), 8.53 (1H, s), 8.11 (1H, dd), 7.82-7.67 (3H, m), 7.60 (1H, d), 3.51 (2H, q), 1.34 (3H, t).

Intermediate Compound M6-4
¹H-NMR (CDCl₃) δ: 9.28 (1H, s), 8.43 (1H, d), 8.25 (1H, s), 8.11-8.05 (1H, m), 7.96 (1H, dd), 7.77-7.64 (3H, m), 3.50 (2H, q), 1.32 (3H, t).

Intermediate Compound M6-6
¹H-NMR (CDCl₃) δ: 10.07 (1H, brs), 9.49-9.34 (1H, m), 8.56 (1H, s), 8.08-7.97 (1H, m), 7.59-7.50 (1H, m), 7.42-7.32 (2H, m), 7.29-7.23 (1H, m), 2.93 (2H, q), 1.27 (3H, t).

Intermediate Compound M6-7
¹H-NMR (CDCl₃) δ: 9.03 (1H, s), 8.44-8.38 (2H, m), 8.34 (1H, s), 8.03-7.96 (2H, m), 7.82 (1H, d), 3.53 (2H, q), 1.35 (3H, t).

Intermediate Compound M6-8
¹H-NMR (CDCl₃) δ: 10.49 (1H, s), 8.66 (1H, d), 8.55 (1H, s), 8.37 (1H, s), 8.05 (1H, d), 7.85 (1H, d), 7.61 (1H, d), 3.53 (2H, q), 1.37 (3H, t).

Intermediate Compound M6-9
¹H-NMR (CDCl₃) δ: 8.82 (1H, s), 8.66 (1H, s), 8.54-8.51 (1H, m), 7.91 (1H, d), 7.70 (1H, s), 7.58 (1H, d), 3.34 (2H, q), 3.05 (2H, q), 1.42-1.35 (6H, m).

Intermediate Compound M6-10
¹H-NMR (CDCl₃) δ: 9.75 (1H, s), 8.35 (1H, d), 8.30 (1H, s), 8.13 (1H, d), 8.01 (1H, dd), 7.97 (1H, dd), 7.81 (1H, d), 3.51 (2H, q), 1.33 (3H, q).

Intermediate Compound M6-11
¹H-NMR (CDCl₃) δ: 9.21 (1H, s), 8.57-8.51 (2H, m), 7.98 (1H, dd), 7.87 (1H, d), 7.68 (1H, s), 7.56 (1H, d), 3.04 (2H, q), 1.36 (3H, t).

Intermediate Compound M6-12
¹H-NMR (CDCl₃) δ: 10.48 (1H, s), 8.67 (1H, d), 8.53 (1H, s), 8.38 (1H, s), 8.06 (1H, d), 7.85 (1H, d), 7.58 (1H, d), 3.54 (2H, q), 1.38 (3H, t).

Intermediate Compound M6-13
¹H-NMR (CDCl₃) δ: 8.74 (1H, s), 8.49 (1H, s), 8.43 (1H, d), 8.36 (1H, s), 8.02 (1H, d), 7.98 (1H, d), 7.83 (1H, d), 3.54 (2H, q), 1.36 (3H, t).

Intermediate Compound M6-14
¹H-NMR (CDCl₃) δ: 10.23 (1H, s), 8.51 (1H, d), 8.01 (1H, dd), 7.88 (1H, s), 7.76 (1H, d), 7.63 (1H, s), 7.51 (1H, dd), 3.00 (2H, q), 1.33 (3H, q).

Intermediate Compound M6-15 ¹H-NMR (DMSO-D₆, 80° C.) δ: 11.09 (1H, s), 8.61 (1H, s), 8.39 (1H, s), 8.18-8.11 (1H, m), 7.48-7.36 (3H, m), 2.93 (4H, q), 1.19 (6H, t).

Intermediate Compound M6-16
¹H-NMR (CDCl₃) δ: 9.48 (1H, s), 8.47 (1H, d), 8.21 (1H, s), 8.00 (1H, d), 7.96 (1H, dd), 7.73 (1H, d), 7.61 (1H, dd), 3.39 (2H, q), 1.30 (3H, t).

Intermediate Compound M6-17
¹H-NMR (CDCl₃) δ: 10.46-9.39 (1H, m), 8.74-7.49 (7H, m), 3.32 (4H, q), 1.27 (6H, t).

Intermediate Compound M6-18
¹H-NMR (CDCl₃) δ: 10.89 (1H, s), 8.64 (1H, d), 8.35 (2H, d), 8.25 (1H, d), 7.91 (1H, t), 7.56 (1H, d), 3.33 (4H, q), 1.28 (6H, t).

Intermediate Compound M6-19
¹H-NMR (CDCl₃) δ: 9.37 (1H, s), 8.41 (1H, dd), 7.91 (1H, d), 7.79 (1H, d), 7.63 (1H, s), 7.55-7.45 (2H, m), 3.00 (2H, q), 1.34 (3H, t).

Intermediate Compound M6-20
¹H-NMR (CDCl₃) δ: 9.39 (1H, s), 8.37 (1H, d), 8.02-7.98 (1H, m), 7.79 (1H, d), 7.72 (1H, dd), 7.64 (1H, s), 7.52 (1H, d), 3.00 (2H, q), 1.34 (3H, t).

Intermediate Compound M6-21

$^1$H-NMR (CDCl$_3$) δ: 9.29 (1H, s), 8.32 (1H, d), 8.17 (1H, s), 7.86 (1H, d), 7.81 (1H, d), 7.65 (1H, s), 7.53 (1H, d), 3.01 (2H, q), 1.34 (3H, t).

Intermediate Compound M6-22

$^1$H-NMR (CDCl$_3$) δ: 9.18 (1H, s), 8.27 (1H, d), 7.95 (1H, s), 7.79 (1H, d), 7.63 (1H, s), 7.57 (1H, d), 7.50 (1H, d), 3.00 (2H, q), 2.28 (3H, s), 1.33 (3H, t).

Next, formulation examples of the compound of the present invention are shown. The part means part by weight.

Formulation Example 1

10 parts of any one of Compounds of Present Invention 1 to 62 and Intermediate Compounds M6-1 to M6-22 are dissolved in a mixture of 35 parts of xylene and 35 parts of N,N-dimethylformamide, 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1 to 62 and Intermediate Compounds M6-1 to M6-22 are further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds of Present Invention 1 to 62 and Intermediate Compounds M6-1 to M6-22 and mixed. Subsequently, an appropriate amount of water is added to this mixture, and the mixture is further stirred, granulated with a granulator, and forced-air dried to obtain each granule.

Formulation Example 4

1 part of any one of Compounds of Present Invention 1 to 62 and Intermediate Compounds M6-1 to M6-22 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate and eliminate acetone to obtain each dust formulation.

Formulation Example 5

35 parts of a mixture of polyoxyethylene alkyl ether sulfate ammonium salt and white carbon (weight ratio 1:1), 10 parts of any one of Compounds of Present Invention 1 to 62 and Intermediate Compounds M6-1 to M6-22 and 55 parts of water are mixed, and finely pulverized by wet grinding method to obtain each flowable.

Formulation Example 6

0.1 parts of any one of Compounds of Present Invention 1 to 62 and Intermediate Compounds M6-1 to M6-22 are dissolved in 5 parts of xylene and 5 parts of trichloroethane, and the mixture is mixed with 89.9 parts of deodorized kerosene to obtain each oil solution.

Formulation Example 7

10 mg of any one of Compounds of Present Invention 1 to 62 and Intermediate Compounds M6-1 to M6-22 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait.

Formulation Example 8

0.1 parts of any one of Compounds of Present Invention 1 to 62 and Intermediate Compounds M6-1 to M6-22 and 49.9 parts of Neothiozol (Chuo Kasei Co., Ltd.) are filled into an aerosol can, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of Compounds of Present Invention 1 to 62 and Intermediate Compounds M6-1 to M6-22, 0.01 parts of BHT (2,6-di-tert-butyl-4-methylphenol), 5 parts of xylene, 3.39 parts of deodorized kerosene and 1 part of emulsifier {Atmos 300 (registered trade name for Atmos Chemical Ltd.)} are mixed and dissolved, and the resulting solution and 50 parts of distilled water are filled into an aerosol container. A valve is attached to the container, and then 40 parts of a propellant (LPG) is filled under pressure through the valve to obtain an aqueous aerosol.

Formulation Example 10

0.1 g of any one of Compounds of Present Invention 1 to 62 and Intermediate Compounds M6-1 to M6-22 are dissolved in 2 ml of propylene glycol, and the solution is impregnated in a porous ceramic plate with a size of 4.0×4.0 cm and 1.2 cm in thickness to obtain a heating type smoking agent.

Formulation Example 11

5 parts of any one of Compounds of Present Invention 1 to 62 and Intermediate Compounds M6-1 to M6-22 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 12

5 parts of any one of Compounds of Present Invention 1 to 62 and Intermediate Compounds M6-1 to M6-22 and 95 parts of a soft vinyl chloride resin are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 13

100 mg of any one of Compounds of Present Invention 1 to 62 and Intermediate Compounds M6-1 to M6-22, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture is compressed to an appropriate size to obtain a tablet.

Formulation Example 14

25 mg of any one of Compounds of Present Invention 1 to 62 and Intermediate Compounds M6-1 to M6-22, 60 mg of lactose, 25 mg of corn starch, 6 mg of carmellose calcium and an appropriate amount of 5% hydroxypropyl methylcellulose are mixed, and the resulting mixture is filled into a hard shell gelatin capsule or a hydroxypropyl methylcellulose capsule to obtain an encapsulated formulation.

Formulation Example 15

Distilled water is added to 1000 mg of anyone of Compounds of Present Invention 1 to 62 and Intermediate Compounds M6-1 to M6-22, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that a final volume is 100 ml, and the mixture is mixed to obtain a suspension for oral administration.

Formulation Example 16

5 parts of any one of Compounds of Present Invention 1 to 62 and Intermediate Compounds M6-1 to M6-22 and 5 parts of polysorbate 85 are dissolved in 3 parts of benzyl alcohol and 30 parts of propylene glycol, a phosphate buffer is added to this solution so as to have a pH of 6.0 to 6.5, and then water is added until a total amount is 100 parts to obtain a liquid formulation for oral administration.

Formulation Example 17

5 parts of aluminum distearate are dispersed in 57 parts of fractionated palm oil and 3 parts of polysorbate 85 by heating. This dispersion is cooled to room temperature, and 25 parts of saccharin are dispersed in an oily vehicle thereof. 10 parts of any one of Compounds of Present Invention 1 to 62 and Intermediate Compounds M6-1 to M6-22 are added thereto to obtain a paste formulation for oral administration.

Formulation Example 18

5 parts of any one of Compounds of Present Invention 1 to 62 and Intermediate Compounds M6-1 to M6-22 and 95 parts of limestone filler are mixed, and a granule for oral administration is obtained using wet granulation method.

Formulation Example 19

5 parts of any one of Compounds of Present Invention 1 to 62 and Intermediate Compounds M6-1 to M6-22 are dissolved in 80 parts of diethylene glycol monoethyl ether, and 15 parts of propylene carbonate are mixed therewith to obtain a spot-on solution.

Formulation Example 20

10 parts of any one of Compounds of Present Invention 1 to 62 and Intermediate Compounds M6-1 to M6-22 are dissolved in 70 parts of diethylene glycol monoethyl ether, and 20 parts of 2-octyl dodecanol are mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds of Present Invention 1 to 62 and Intermediate Compounds M6-1 to M6-22, the mixture is sufficiently stirred and mixed until it becomes a uniform solution, and then 19.5 parts of water are added and further sufficiently stirred and mixed to obtain a shampoo agent as a uniform solution.

Formulation Example 22

0.15 parts of any one of Compounds of Present Invention 1 to 62 and Intermediate Compounds M6-1 to M6-22, 95 parts of an animal feed and 4.85 parts of a mixture of secondary calcium phosphate, diatomaceous earth, Aerosil and carbonate (or chalk) are sufficiently stirred and mixed to obtain a feed premix for animal.

Formulation Example 23

7.2 g of any one of Compounds of Present Invention 1 to 62 and Intermediate Compounds M6-1 to M6-22 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention and the intermediate compound is shown as test examples.

Test Example 1

The formulations of Compounds of Present Invention 1 to 21, 44, 46 to 48, 52, 54, 57 and 60 and Intermediate Compounds M6-1, M6-4, M6-12, M6-13, M6-15 and M6-18 as obtained in Formulation Example 5 were diluted with water, so as to have a concentration of the active ingredient of 500 ppm, to prepare a diluted liquid for test.

On the other hand, on a cucumber seedling (the first true leaf stage) planted in a plastic cup was inoculated with about 30 *Aphis gossypii* (all stages), and leaving it for a day. 20 ml of the diluted liquid for test was sprayed on the seedling.

Six days after spraying, the number of surviving *Aphis gossypii* parasitized on the leaves of the cucumber was examined, and the controlling value was calculated according to the following equation:

Controlling value (%)=$\{1-(Cb \times Tai)/(Cai \times Tb)\} \times 100$ wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the test drug solution prepared by diluting the formulation not containing the compound of the present invention and the intermediate compound as in Formulation Example 5 with the same amount of water as in the treated section was sprayed.

As a result, in the treated section using a diluted liquid for test of each of Compounds of Present Invention 1 to 21, 44, 46 to 48, 52, 54, 57 and 60 and Intermediate Compounds M6-1, M6-4, M6-12, M6-13, M6-15 and M6-18, the controlling value was 90% or more.

Test Example 2

The formulations of Compounds of Present Invention 5 to 7, 10 to 21, 44, 45 and 57 and Intermediate Compounds M6-4 and M6-12 as obtained in Formulation Example 5 were diluted with water, so as to have a concentration of the active ingredient of 500 ppm, to prepare a diluted liquid for test.

On the other hand, a cucumber seedling (the second true leaf stage) planted in a plastic cup was drenched at its foot with 5 ml of the diluted liquid for test, and kept in a greenhouse at 25° C. for 7 days. On the cucumber leaf surface was inoculated about 30 *Aphis gossypii* (all stages), and further kept in the greenhouse for 6 days, then the number of surviving *Aphis gossypii* parasitized on the leaves of the cucumber was examined, and the controlling value was calculated according to the following equation:

Controlling value (%)={1−(Cb×Tai)/(Cai×Tb)}×100 wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the diluted liquid for test prepared by diluting the formulation not containing the compound of the present invention and the intermediate compound as in Formulation Example 5 with the same amount of water as in the treated section was sprayed.

As a result, in the treated section using a diluted liquid for test of each of Compounds of Present Invention 5 to 7, 10 to 21, 44, 45 and 57 and Intermediate Compounds M6-4 and M6-12, the controlling value was 90% or more.

Test Example 3

The formulations of Compounds of Present Invention 1 to 3, 6 to 7, 9 to 10, 13 to 16, 18 to 21, 44 and 57 and Intermediate Compound M6-15 as obtained in Formulation Example 5 were diluted with water, so as to have a concentration of the active ingredient of 500 ppm, to prepare a diluted liquid for test.

On a rice seedling in the second leaf stage planted in a polyethylene cup was sprayed 10 ml of each diluted liquid for test. After air-drying, 20 third-fourth instar larvae of *Nilaparvata lugens* were released, and kept in the greenhouse at 25° C. After 6 days, the number of *Nilaparvata lugens* parasitized on the rice was examined, and the controlling value was calculated according to the following equation:

Controlling value (%)={1−(Cb×Tai)/(Cai×Tb)}×100 wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the diluted liquid for test prepared by diluting the formulation not containing the compound of the present invention as in Formulation Example 5 with the same amount of water as in the treated section was sprayed.

As a result, in the treated section using a diluted liquid for test of each of Compounds of Present Invention 1 to 3, 6 to 7, 9 to 10, 13 to 16, 18 to 21, 44 and 57 and Intermediate Compound M6-15, the controlling value was 90% or more.

Test Example 4

The formulations of Compounds of Present Invention 2 to 3, 6 to 7, 9 to 11, 13 to 21, 44 and 57 as obtained in Formulation Example 5 were diluted with water, so as to have a concentration of the active ingredient of 500 ppm, to prepare a diluted liquid for test.

On the other hand, a rice seedling (2 weeks after sowing, the second leaf stage) planted in a plastic cup was drenched at its foot with 5 ml of each diluted liquid for test, and kept in a greenhouse of 25° C. for 7 days. 20 third-fourth instar larvae of *Nilaparvata lugens* were released, and further kept in the greenhouse for 6 days, then the number of surviving *Nilaparvata lugens* parasitized on the rice was examined, and the controlling value was calculated according to the following equation:

Controlling value (%)={1−(Cb×Tai)/(Cai×Tb)}×100 wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the diluted liquid for test prepared by diluting the formulation not containing the compound of the present invention as in Formulation Example 5 with the same amount of water as in the treated section was sprayed.

As a result, in the treated section using a diluted liquid for test of each of Compounds of Present Invention 2 to 3, 6 to 7, 9 to 11, 13 to 21, 44 and 57, the controlling value was 90% or more.

Test Example 5

The formulations of Compounds of Present Invention 4 to 7, 9 to 21, 44 and 57 as obtained in Formulation Example 5 were diluted with water, so as to have a concentration of the active ingredient of 500 ppm, to prepare a diluted liquid for test.

On the other hand, *Bemisia tabaci* adult was released on a tomato seedling (the third true leaf stage) planted in a polyethylene cup, and made to lay eggs for about 72 hours. The tomato seedling was kept in a greenhouse for 8 days, and when larvae hatched from the eggs, the above diluted liquid for test was sprayed in an amount of 20 ml/cup, and the cup was kept in a greenhouse at 25° C. After 7 days, the number of surviving larvae on the tomato leaves was examined, and the controlling value was calculated according to the following equation:

Controlling value (%)={1−($Cb \times Tai$)/($Cai \times Tb$)}×100 wherein the symbols represent as follows:

Cb: the number of insects in a non-treated section before treatment,

Cai: the number of insects in a non-treated section on observation,

Tb: the number of insects in a treated section before treatment,

Tai: the number of insects in a treated section on observation, wherein the non-treated section refers to a section where the diluted liquid for test prepared by diluting the formulation not containing the compound of the present invention as in Formulation Example 5 with the same amount of water as in the treated section was sprayed.

As a result, in the treated section using a diluted liquid for test containing each of Compounds of Present Invention 4 to 7, 9 to 21, 44 and 57, the controlling value was 90% or more.

Test Example 6

The formulations of Compounds of Present Invention 2 to 3, 7, 9 to 10, 12 to 21, 44 to 48, 52, 54 and 57 and Intermediate Compounds M6-1, M6-2, M6-4, M6-5, M6-11 to M6-13 and M6-15 as obtained in Formulation Example 5 were diluted with water, so as to have a concentration of the active ingredient of 500 ppm, to prepare a diluted liquid for test.

On the other hand, on cabbage at the third leaf stage planted in a polyethylene cup was sprayed in an amount of 20 mL/cup of the diluted liquid for test. After the drug solution was dried, the foliage part was cut off, and then placed in a 50 mL volume cup. Five second instar larvae of *Plutella xylostella* were released into the cup, and the cup was sealed with a lid. After the cup was kept at 25° C. for 5 days, the number of surviving insects was counted. The mortality was calculated according to the following equation:

Mortality (%)=(Number of dead insects/Number of tested insects)×100.

As a result, in the treated section using a diluted liquid for test of each of Compounds of Present Invention 2 to 3, 7, 9 to 10, 12 to 21, 44 to 48, 52, 54 and 57 and Intermediate Compounds M6-1, M6-2, M6-4, M6-5, M6-11 to M6-13 and M6-15, the mortality was 80% or more.

Test Example 7

The formulations of Compounds of Present Invention 3 to 21, 44 to 48, 52, 54 and 56 to 58 and Intermediate Compounds M6-2, M6-5, M6-7 to M6-8, M6-10 to M6-13 and M6-18 as obtained in Formulation Example 5 were diluted with water, so as to have a concentration of the active ingredient of 500 ppm, to prepare a diluted liquid for test.

On the other hand, an apple tree was planted in a plastic cup, and grown until the seventh-eighth true leaf was spread.

To the apple tree was sprayed in an amount of 20 mL/cup of the diluted liquid for test. After the drug solution was dried, 60 first-instar *Adoxophyes orana fasciata* were released, and the plastic cup the bottom of which was cut off and on which a filter paper was put was upside-down and covered. After 7 days, the number of surviving insects was counted, and the mortality was calculated according to the following equation:

Mortality (%)=(Number of dead insects/Number of tested insects)×100.

As a result, in the treated section using a diluted liquid for test of each of Compounds of Present Invention 3 to 21, 44 to 48, 52, 54 and 56 to 58 and Intermediate Compounds M6-2, M6-5, M6-7 to M6-8, M6-10 to M6-13 and M6-18, the mortality was 90% or more.

Test Example 8

The formulations of Compounds of Present Invention 1 to 3, 9, 13 to 16 and 57 as obtained in Formulation Example 5 were diluted with water, so as to have a concentration of the active ingredient of 500 ppm, to prepare a diluted liquid for test.

A filter paper having a diameter of 5.5 cm was spread on the bottom of a polyethylene cup having the same diameter and 0.7 ml of the diluted liquid for test was added dropwise onto the filter paper, and 30 mg of sucrose was uniformly placed as bait. Into the polyethylene cup, 10 female adults of *Musca domestica* were released, and the cup was sealed with a lid. After 24 hours, survived and dead number of *Musca domestica* was examined, and the mortality was calculated.

As a result, in the treated section using a diluted liquid for test containing each of Compounds of Present Invention 1 to 3, 9, 13 to 16 and 57, the mortality was 100%.

Test Example 9

The formulation of Compound of Present Invention 1 as obtained in Formulation Example 5 was diluted with water, so as to have a concentration of the active ingredient of 500 ppm, to prepare a diluted liquid for test.

A filter paper having a diameter of 5.5 cm was spread on the bottom of a polyethylene cup having the same diameter and 0.7 ml of the diluted liquid for test was added dropwise onto the filter paper, and 30 mg of sucrose was uniformly placed as bait. Into the polyethylene cup, 2 male adults of *Blattella germanica* were released, and the cup was sealed with a lid. After 6 days, survived and dead number of *Blattella germanica* was examined, and the mortality was calculated.

As a result, in the treated section using each diluted liquid for test containing Compound of Present Invention 1, the mortality was 100%.

Test Example 10

The formulations of Compounds of Present Invention 1 to 3, 7, 9 to 10, 12 to 14, 17, 20 to 21, 44 and 60 and Intermediate Compounds M6-1, M6-4 and M6-11 to M6-13 as obtained in Formulation Example 5 were diluted with water, so as to have a concentration of the active ingredient of 500 ppm, to prepare a diluted liquid for test.

0.7 ml of the diluted liquid for test was added to 100 ml of ion-exchanged water (active ingredient concentration: 3.5 ppm). 20 last-instar larvae of *Culex pipiens pallens* were released into the solution. One day later, survived and dead number of the *Culex pipiens pallens* was examined, and the mortality of the pest was calculated.

As a result, in the treated section using a diluted liquid for test of each of Compounds of Present Invention 1 to 3, 7, 9 to 10, 12 to 14, 17, 20 to 21, 44 and 60 and Intermediate Compounds M6-1, M6-4 and M6-11 to M6-13, the mortality was 91% or more.

Test Example 11

2 mg of each of Compounds of Present Invention 1, 2, 13, 20, 21, 45 to 47, 52 to 55 and 57 and Intermediate Compound M6-13 was weighed in a screw tube (Maruemu No. 5; 27×55 mm), and 0.2 mL of acetone was added thereto and sealed with a cap to dissolve the compound. The screw tube was rotated and inverted to uniformity coat the drug solution onto the whole inner wall of the tube. After removing the cap, the solution was air-dried for about 2 hours, then non-blood-sucking nymphal ticks, *Haemaphysalis longicornis* (5 ticks/group) were released, and the tube was sealed with the cap. After 2 days, the number of dead ticks was examined, and the mortality was calculated according to the following equation:

Mortality (%)=100×(Number of dead ticks/Number of tested ticks).

As a result, in the treated section using a diluted liquid for test of each of Compounds of Present Invention 1, 2, 13, 20, 21, 45 to 47, 52 to 55 and 57 and Intermediate Compound M6-13, the mortality was 100%.

INDUSTRIAL APPLICABILITY

The compound of the present invention and the present intermediate compound have a controlling effect on pests and are useful as an active ingredient of a pest control agent.

The invention claimed is:

1. An amide compound represented by formula (1) or an N-oxide thereof:

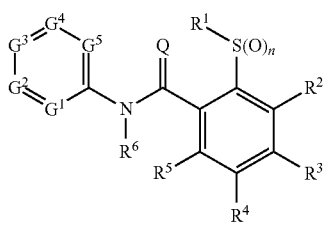

(1)

wherein $R^1$ represents a C1 to C6 chain hydrocarbon group optionally having one or more atoms or groups selected from group X or a C3 to C6 cycloalkyl group optionally having one or more atoms or groups selected from group Y, $R^2$, $R^3$, $R^4$ and $R^5$ are the same or different and represent a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $—OR^{12}$, $—S(O)_mR^{12}$, $—S(O)_2NR^{12}R^{13}$, $—NR^{12}R^{13}$, $—NR^{12}C(O)R^{13}$, $—NR^{12}CO_2R^{13}$, $—NR^{12}S(O)_2R^{14}$, $—C(O)R^{12}$, $—CO_2R^{12}$, $—C(O)NR^{12}R^{13}$, $—SF_5$, a cyano group, a nitro group, a halogen atom, or a hydrogen atom, $R^6$ represents a C1 to C6 chain hydrocarbon group optionally having one or more atoms or groups selected from group W, a C3 to C6 cycloalkyl group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $—C(O)R^{12}$, $—C(O)OR^{12}$, or $—C(O)NR^{12}R^{13}$, $G^1$ represents a nitrogen atom or $=CR^7—$, $G^2$ represents a nitrogen atom or $=CR^8—$, $G^3$ represents $=CR^9—$, $G^4$ represents $=CR^{10}—$, $G^5$ represents a nitrogen atom or $=CR^{11}—$ (wherein one or two of $G^1$, $G^2$, and $G^5$ represents a nitrogen atom), $R^7$ and $R^{11}$ are the same or different and represent a C1 to C6 chain hydrocarbon group optionally having one or more atoms or groups selected from group X, a C3 to C6 cycloalkyl group optionally having one or more atoms or groups selected from group Y, $—OR^{15}$, $—S(O)_mR^{15}$, a fluorine atom, or a hydrogen atom, $R^8$, $R^9$ and $R^{10}$ are the same or different and represent a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $—OR^{12}$, $—S(O)_mR^{12}$, $—S(O)_2NR^{12}R^{13}$, $—NR^{12}R^{13}$, $—NR^{12}C(O)R^{13}$, $—NR^{12}CO_2R^{13}$, $—NR^{12}S(O)_2R^{14}$, $—C(O)R^{12}$, $—CO_2R^{12}$, $—C(O)NR^{12}R^{13}$, $—SF_5$, a cyano group, a nitro group, a halogen atom, or a hydrogen atom (wherein at least one of $R^8$, $R^9$ and $R^{10}$ represents a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $—OR^{12}$, $—S(O)_mR^{12}$, $—S(O)_2NR^{12}R^{13}$, $—NR^{12}R^{13}$, $—NR^{12}C(O)R^{13}$, $—NR^{12}CO_2R^{13}$, $—NR^{12}S(O)_2R^{14}$, $—C(O)R^{12}$, $—CO_2R^{12}$, $—C(O)NR^{12}R^{13}$, $—SF_5$, a cyano group, a nitro group, or a halogen atom), $R^{12}$ and $R^{13}$ are the same or different and represent a C1 to C6 chain hydrocarbon group optionally having one or more halogen atoms, a phenyl group optionally having one or more atoms or groups selected from group Z, a 5- or 6-membered heterocyclic group optionally having one or more atoms or groups selected from group Z, or a hydrogen atom, $R^{14}$ represents a C1 to C6 chain hydrocarbon group optionally having one or more halogen atoms, a phenyl group optionally having one or more atoms or groups selected from group Z, or a 5- or 6-membered heterocyclic group optionally having one or more atoms or groups selected from group Z, $R^{15}$ represents a C1 to C6 alkyl group optionally having one or more halogen atoms, Q represents an oxygen atom or a sulfur atom, m represents 0, 1 or 2, and n represents 0, 1 or 2, wherein, when $R^1$ represents an ethyl group, $R^2$, $R^3$, $R^4$ and $R^5$ represent a hydrogen atom, $G^1$, $G^4$ and $G^5$ represent =CH—, and $G^2$ represents an nitrogen atom, $G^3$ does not represent =C(OCH$_3$)—, and when m is 1 or 2 in —S(O)$_m$R$^{12}$, $R^{12}$ does not represent a hydrogen atom; wherein group X is selected from the group consisting of C3 to C6 cycloalkyl groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms;

group Y is selected from the group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms;

group Z is selected from the group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C1 to C6 alkylamino groups optionally having one or more halogen atoms, C2 to C8 dialkylamino groups optionally having one or more halogen atoms, C2 to C6 alkylcarbonyl groups optionally having one or more halogen atoms, C2 to C6 alkoxycarbonyl groups optionally having one or more halogen atoms, hydroxy groups, thiol groups, amino groups, cyano groups, nitro groups, and halogen atoms; and group W is selected from the group consisting of C3 to C6 cycloalkyl groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkoxycarbonyl groups optionally having one or more halogen atoms, hydroxy groups, nitrile groups, and halogen atoms.

2. The compound according to claim 1, wherein $R^1$ is a C3 to C6 cycloalkyl group optionally having one or more atoms or groups selected from the group consisting of halogen atoms and C1 to C3 alkyl groups, a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms, $R^2$, $R^4$ and $R^5$ are the same or different and are a C1 to C6 alkyl group optionally having one or more halogen atoms, —OR$^{12}$, —S(O)$_m$R$^{12}$, a halogen atom, or a hydrogen atom, $R^3$ represents a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, —OR$^{12}$, —S(O)$_m$R$^{12}$, —NR$^{12}$R$^{13}$, —NR$^{12}$C(O)R$^{13}$, —NR$^{12}$CO$_2$R$^{13}$, —NR$^{12}$S(O)$_2$R$^{14}$, —C(O)R$^{12}$, —CO$_2$R$^{12}$, —C(O)NR$^{12}$R$^{13}$, —SF$_5$, a cyano group, a nitro group, a halogen atom, or a hydrogen atom), $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), a (C1 to C6 alkoxy) C1 to C6 alkyl group optionally having one or more halogen atoms, —C(O)R$^{12}$, or —C(O)OR$^{12}$, one or two of $G^1$, $G^2$, and $G^5$ are a nitrogen atom, $R^7$ and $R^{11}$ are the same or different and are a C1 to C6 alkyl group optionally having one or more halogen atoms, —OR$^{15}$, —S(O)$_m$R$^{15}$, a fluorine atom, or a hydrogen atom, $R^8$, $R^9$ and $R^{10}$ are the same or different and are a C1 to C6 chain hydrocarbon group optionally having one or more atoms or groups selected from group X, —OR$^{12}$, —S(O)$_m$ R$^{12}$, —SF$_5$, a halogen atom, or a hydrogen atom (wherein at least one of $R^8$, $R^9$, and $R^{10}$ is a C1 to C6 chain hydrocarbon group optionally having one or more atoms or groups selected from group X, —OR$^{12}$, —S(O)$_m$R$^{12}$, -SF$_5$, or a halogen atom), $R^{12}$ and $R^{13}$ are the same or different and are a C1 to C6 alkyl group optionally having one or more halogen atoms, a phenyl group (wherein the phenyl group optionally has one or more atoms or groups selected from the group consisting of C1 to C3 alkyl groups optionally having one or more halogen atoms and halogen atoms), a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), or a hydrogen atom, $R^{14}$ is a C1 to C6 alkyl group optionally having one or more halogen atoms, a phenyl group (wherein the phenyl group optionally has a C1 to C3 alkyl group optionally having one or more halogen atoms or one or more halogen atoms), or a 5- or 6-membered heterocyclic group (wherein the 5- or 6-membered heterocyclic group optionally has a C1 to C3 alkyl group optionally having one or more halogen atoms or one or more halogen atoms), and Q is an oxygen atom.

3. The compound according to claim 1, wherein $R^1$ is a C3 to C6 cycloalkyl group optionally having one or more atoms or groups selected from the group consisting of halogen atoms and C1 to C3 alkyl groups, a C2 to C6 alkyl group optionally having one or more halogen atoms, or a (C3 to C6 cycloalkyl)C1 to C3 alkyl group optionally having one or more halogen atoms, $R^2$, $R^4$ and $R^5$ are the same or different and are a halogen atom or a hydrogen atom, $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), —$OR^{12}$, —$S(O)_m R^{12}$, —$NR^{12}R^{13}$, —$NR^{12}C(O)R^{13}$, —$NR^{12}CO_2R^{13}$, —$NR^{12}S(O)_2R^{14}$, —$C(O)R^{12}$, —$CO_2R^{12}$, —$C(O)NR^{12}R^{13}$, a halogen atom, or a hydrogen atom, $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms, or a C2 to C6 alkoxycarbonyl group optionally having one or more halogen atoms, one or two of $G^1$, $G^2$, and $G^5$ are a nitrogen atom, $R^7$ and $R^{11}$ are the same or different and are a fluorine atom or a hydrogen atom, $R^8$, $R^9$ and $R^{10}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, —$OR^{12}$, —$S(O)_m R^{12}$, a halogen atom, or a hydrogen atom (wherein at least one of $R^8$, $R^9$, and $R^{10}$ is a C1 to C6 alkyl group optionally having one or more halogen atoms, a C2 to C6 alkenyl group optionally having one or more halogen atoms, a C2 to C6 alkynyl group optionally having one or more halogen atoms, —$OR^{12}$, —$S(O)_m R^{12}$, a halogen atom), $R^{12}$ and $R^{13}$ are the same or different and are a C1 to C6 alkyl group optionally having one or more halogen atoms or a hydrogen atom, $R^{14}$ is a C1 to C6 alkyl group optionally having one or more halogen atoms, and Q is an oxygen atom.

4. The compound according to claim 1, wherein $R^1$ is a C2 to C6 alkyl group, a cyclopropyl group, or a cyclopropylmethyl group, $R^2$, $R^4$ and $R^5$ are a hydrogen atom, $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C1 to C3 alkylsulfonylamino group optionally having one or more halogen atoms, an amino group, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C8 dialkylaminocarbonyl group optionally having one or more halogen atoms, an aminocarbonyl group, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or groups selected from the group consisting of C1 to C3 alkyl groups optionally having one or more halogen atoms and halogen atoms), a halogen atom, or a hydrogen atom, $R^6$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms, or a C2 to C6 alkoxycarbonyl group optionally having one or more halogen atoms, one or two of $G^1$, $G^2$, and $G^5$ are a nitrogen atom, $R^7$ and $R^{11}$ are the same or different and are a fluorine atom or a hydrogen atom, $R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom, or a hydrogen atom (wherein at least one of $R^8$, $R^9$ and $R^{10}$ is a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, or a halogen atom), and Q is an oxygen atom.

5. The compound as defined in claim 1, wherein two of $G^1$, $G^2$, and $G^5$ are a nitrogen atom.

6. The compound as defined in claim 1, wherein one of $G^1$, $G^2$, and $G^5$ is a nitrogen atom.

7. The compound as defined in claim 1, wherein $G^1$ is a nitrogen atom, $G^2$ is =$CR^8$—, $G^3$ is =$CR^9$—, $G^4$ is =$CR^{10}$—, and $G^5$ is =$CR^{11}$—.

8. The compound as defined in claim 1, wherein $G^1$ is =$CR^7$—,
$G^2$ is a nitrogen atom,
$G^3$ is =$CR^9$—,
$G^4$ is =$CR^{10}$—, and
$G^5$ is =$CR^{11}$—.

9. The compound as defined in claim 1, wherein $G^1$ is a nitrogen atom or =$CR^7$—,
$G^2$ is a nitrogen atom or =$CR^8$—,
$G^3$ is =$CR^9$—,
$G^4$ is =$CR^{10}$—,
$G^5$ is a nitrogen atom or =$CR^{11}$— (wherein one or two of $G^1$, $G^2$ and $G^5$ represent a nitrogen atom),
$R^7$ and $R^{11}$ are the same or different and are a fluorine atom or a hydrogen atom, and
$R^8$, $R^9$ and $R^{10}$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom, or a hydrogen atom (wherein at least one of $R^8$, $R^9$, and $R^{10}$ is a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, or a halogen atom).

10. The compound as defined in claim 1, wherein $G^1$ is a nitrogen atom or =CH—,
$G^2$ is a nitrogen atom or =$CR^8$—,
$G^3$ is =$CR^9$—,
$G^4$ is =$CR^{10}$—,
$G^5$ is a nitrogen atom or =CH— (wherein one or two of $G^1$, $G^2$ and $G^5$ represent a nitrogen atom), and
$R^8$, $R^9$ and $R^{10}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom, or a hydrogen atom (wherein at least one of $R^8$, $R^9$, and $R^{10}$ is a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, or a halogen atom).

11. A pest control composition comprising an amide compound represented by formula (1) or an N-oxide thereof, and an inert carrier:

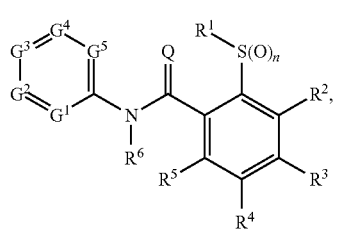

(1)

wherein
$R^1$ represents a C1 to C6 chain hydrocarbon group optionally having one or more atoms or groups selected from group X or a C3 to C6 cycloalkyl group optionally having one or more atoms or groups selected from group Y,
$R^2$, $R^3$, $R^4$ and $R^5$ are the same or different and represent a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, —$OR^{12}$, —$S(O)_m R^{12}$, —$S(O)_2 NR^{12}R^{13}$, —$NR^{12}R^{13}$, —$NR^{12}C(O)R^{13}$, —$NR^{12}CO_2 R^{13}$, —$NR^{12}S(O)_2 R^{14}$, —$C(O)R^{12}$, —$CO_2 R^{12}$, —$C(O)NR^{12}R^{13}$, —$SF_5$, a cyano group, a nitro group, a halogen atom, or a hydrogen atom,
$R^6$ represents a C1 to C6 chain hydrocarbon group optionally having one or more atoms or groups selected from group W, a C3 to C6 cycloalkyl group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), —$C(O)R^{12}$, —$C(O)OR^{12}$, or —$C(O)NR^{12}R^{13}$,
$G^1$ represents a nitrogen atom or =$CR^7$—,
$G^2$ represents a nitrogen atom or =$CR^8$—,
$G^3$ represents a nitrogen atom or =$CR^9$—,
$G^4$ represents a nitrogen atom or =$CR^{10}$—,
$G^5$ represents a nitrogen atom or =$CR^{11}$— (wherein at least one of $G^1$, $G^2$, $G^3$, $G^4$ and $G^5$ represents a nitrogen atom, but not all of $G^2$, $G^3$ and $G^4$ represent a nitrogen atom),
$R^7$ and $R^{11}$ are the same or different and represent a C1 to C6 chain hydrocarbon group optionally having one or more atoms or groups selected from group X, a C3 to C6 cycloalkyl group optionally having one or more atoms or groups selected from group Y, —$OR^{15}$, —$S(O)_m R^{15}$, a fluorine atom, or a hydrogen atom,
$R^8$, $R^9$ and $R^{10}$ are the same or different and represent a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, —$OR^{12}$, —$S(O)_m R^{12}$, $S(O)_2 NR^{12}R^{13}$, —$NR^{12}R^{13}$, —$NR^{12}C(O)R^{13}$, —$NR^{12}CO_2 R^{13}$, —$NR^{12}S(O)_2 R^{14}$, —$C(O)R^{12}$, —$CO_2 R^{12}$, —$C(O)NR^{12}R^{13}$, —$SF_5$, a cyano group, a nitro group, a halogen atom, or a hydrogen atom (wherein at least one of $R^8$, $R^9$ and $R^{10}$ represents a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, —$OR^{12}$, —$S(O)_m R^{12}$, —$S(O)_2 NR^{12}R^{13}$, —$NR^{12}R^{13}$, —$NR^{12}C(O)R^{13}$, —$NR^{12}CO_2 R^{13}$, —$NR^{12}S(O)_2 R^{14}$, —$C(O)R^{12}$, —$CO_2 R^{12}$, —$C(O)NR^{12}R^{13}$, —$SF_5$, a cyano group, a nitro group, or a halogen atom),
$R^{12}$ and $R^{13}$ are the same or different and represent a C1 to C6 chain hydrocarbon group optionally having one or more halogen atoms, a phenyl group optionally having one or more atoms or groups selected from group Z, a 5- or 6-membered heterocyclic group optionally having one or more atoms or groups selected from group Z, or a hydrogen atom, $R^{14}$ represents a C1 to C6 chain hydrocarbon group optionally having one or more halogen atoms, a phenyl group optionally having one or more atoms or groups selected from group Z, or a 5- or 6-membered heterocyclic group optionally having one or more atoms or groups selected from group Z, $R^{15}$ represents a C1 to C6 alkyl group optionally having one or more halogen atoms, Q represents an oxygen atom or a sulfur atom, m represents 0, 1 or 2, and n represents 0, 1 or 2, wherein, when $R^1$ represents an ethyl group, $R^2$, $R^3$, $R^4$ and $R^5$ represent a hydrogen atom, $G^1$, $G^4$ and $G^5$ represent =CH—, and $G^2$ represents an nitrogen atom, $G^3$ does not represent =C(OCH$_3$)—, and when m is 1 or 2 in —S(O)$_m$R$^{12}$, $R^{12}$ does not represent a hydrogen atom; wherein group X is selected from the group consisting of C3 to C6 cycloalkyl groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms;

group Y is selected from the group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms;

group Z is selected from the group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C1 to C6 alkylamino groups optionally having one or more halogen atoms, C2 to C8 dialkylamino groups optionally having one or more halogen atoms, C2 to C6 alkylcarbonyl groups optionally having one or more halogen atoms, C2 to C6 alkoxycarbonyl groups optionally having one or more halogen atoms, hydroxy groups, thiol groups, amino groups, cyano groups, nitro groups, and halogen atoms; and group W is selected from the group consisting of C3 to C6 cycloalkyl groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkoxycarbonyl groups optionally having one or more halogen atoms, hydroxy groups, nitrile groups, and halogen atoms.

12. A method for controlling pests comprising applying an effective amount of the compound as defined in claim 1 to a pest or a pest-infested area.

13. A method for controlling pests comprising applying an effective amount of the compound as defined in claim 7 to a pest or a pest-infested area.

14. A method for controlling pests comprising applying an effective amount of the compound as defined in claim 8 to a pest or a pest-infested area.

* * * * *